(12) United States Patent
Fang et al.

(10) Patent No.: US 8,198,474 B2
(45) Date of Patent: Jun. 12, 2012

(54) COMPOUNDS FOR PREPARING IMMUNOLOGICAL ADJUVANT

(75) Inventors: Francis G. Fang, Andover, MA (US); James E. Foy, Andover, MA (US); Lynn Hawkins, Concord, MA (US); Charles Lemelin, North Chelmsford, MA (US); Andre Lescarbeau, Sommerville, MA (US); Xiang Niu, Malden, MA (US); Kuo-Ming Wu, Acton, MA (US)

(73) Assignee: Eisai R&D Management Co., Ltd. (JP)

( * ) Notice: Subject to any disclaimer, the term of this patent is extended or adjusted under 35 U.S.C. 154(b) by 226 days.

(21) Appl. No.: 12/698,686

(22) Filed: Feb. 2, 2010

(65) Prior Publication Data

US 2010/0197951 A1     Aug. 5, 2010

Related U.S. Application Data

(62) Division of application No. 11/477,936, filed on Jun. 30, 2006, now Pat. No. 7,683,200.

(60) Provisional application No. 60/695,324, filed on Jun. 30, 2005.

(51) Int. Cl.
    *C07F 9/02*          (2006.01)
(52) U.S. Cl. ........................... 558/171; 558/172
(58) Field of Classification Search .................. 558/171, 558/172
See application file for complete search history.

(56) References Cited

U.S. PATENT DOCUMENTS

| | | | |
|---|---|---|---|
| 6,290,973 B1 | 9/2001 | Hawkins et al. | |
| 6,521,776 B2 | 2/2003 | Hawkins et al. | |
| 6,551,600 B2 | 4/2003 | Hawkins et al. | |
| 6,835,721 B2 | 12/2004 | Hawkins et al. | |
| 2004/0006242 A1 * | 1/2004 | Hawkins et al. | 554/78 |

FOREIGN PATENT DOCUMENTS

| | | |
|---|---|---|
| WO | 00/44758 | 8/2000 |
| WO | WO 03/099195 | 12/2003 |

OTHER PUBLICATIONS

European Search Report of European Application No. 10012396.7 dated Apr. 11, 2011, (6 pages).
Brandenburg et al., 2004, CAS: 140:352388.
Hawkins et al., 2002, CAS:137:190.

* cited by examiner

*Primary Examiner* — Rei-tsang Shiao
(74) *Attorney, Agent, or Firm* — Myers Bigel Sibley & Sajovec, PA

(57) ABSTRACT

The present invention provides methods for preparing TLR-4 receptor agonist E6020:

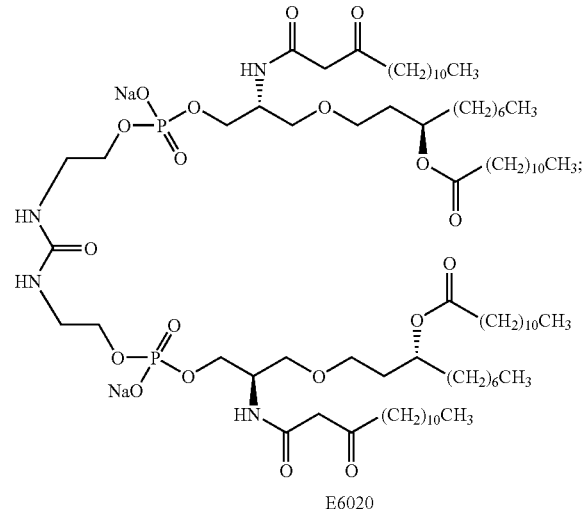

E6020 and stereoisomers thereof, which compounds are useful as an immunological adjuvants when co-administered with antigens such as vaccines for bacterial and viral diseases. Also provided are synthetic intermediates useful for implementing the inventive methods.

20 Claims, 5 Drawing Sheets

COMPOUNDS FOR PREPARING IMMUNOLOGICAL ADJUVANT

CROSS REFERENCE TO RELATED APPLICATIONS

This application is a divisional of U.S. application Ser. No. 11/477,936, filed Jun. 30, 2006, which claims priority under 35 U.S.C. §119 to U.S. Provisional Application No. 60/695,324, filed Jun. 30, 2005, all of which are herein incorporated by reference in their entirety.

BACKGROUND OF THE INVENTION

Generally, vaccines have proven to be successful methods for the prevention of infectious diseases. Generally, they are cost effective, and do not induce antibiotic resistance to the target pathogen or affect normal flora present in the host. In many cases, such as when inducing anti-viral immunity, vaccines can prevent a disease for which there are no viable curative or ameliorative treatments available.

Vaccines function by triggering the immune system to mount a response to an agent, or antigen, typically an infectious organism or a portion thereof that is introduced into the body in a non-infectious or non-pathogenic form. Once the immune system has been "primed" or sensitized to the organism, later exposure of the immune system to this organism as an infectious pathogen results in a rapid and robust immune response that destroys the pathogen before it can multiply and infect enough cells in the host organism to cause disease symptoms.

The agent, or antigen, used to prime the immune system can be the entire organism in a less infectious state, known as an attenuated organism, or in some cases, components of the organism such as carbohydrates, proteins or peptides representing various structural components of the organism.

In many cases, it is necessary to enhance the immune response to the antigens present in a vaccine in order to stimulate the immune system to a sufficient extent to make a vaccine effective, i.e., to confer immunity. Many protein and most peptide and carbohydrate antigens, administered alone, do not elicit a sufficient antibody response to confer immunity. Such antigens need to be presented to the immune system in such a way that they will be recognized as foreign and will elicit an immune response. To this end, additives (adjuvants) have been devised which immobilize antigens and stimulate the immune response.

The best known adjuvant, Freund's complete adjuvant, consists of a mixture of mycobacteria in an oil/water emulsion. Freund's adjuvant works in two ways: first, by enhancing cell and humoral-mediated immunity, and second, by blocking rapid dispersal of the antigen challenge (the "depot effect"). However, due to frequent toxic physiological and immunological reactions to this material, Freund's adjuvant cannot be used in humans.

Another molecule that has been shown to have immunostimulatory or adjuvant activity is endotoxin, also known as lipopolysaccharide (LPS). LPS stimulates the immune system by triggering an "innate" immune response—a response that has evolved to enable an organism to recognize endotoxin (and the invading bacteria of which it is a component) without the need for the organism to have been previously exposed. While LPS is too toxic to be a viable adjuvant, molecules that are structurally related to endotoxin, such as monophosphoryl lipid A ("MPL") are being tested as adjuvants in clinical trials. Both LPS and MPL have been demonstrated to be agonists to the human toll-like receptor-4 (TLR-4). Currently, however, the only FDA-approved adjuvant for use in humans is aluminum salts (Alum) which are used to "depot" antigens by precipitation of the antigens. Alum also stimulates the immune response to antigens.

Accordingly, there is a need to develop synthetic methods for preparing compounds which can be co-administered with antigens in order to stimulate the immune system to generate a more robust antibody response to the antigen than would be seen if the antigen were injected alone or with Alum.

SUMMARY OF THE INVENTION

In one aspect, the present invention provides a method for synthesizing the TLR-4 receptor agonist E6020 having the structure:

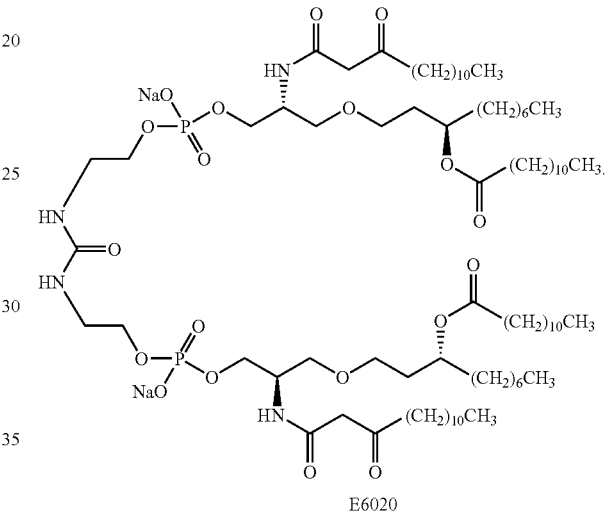

E6020

In another aspect, the invention encompasses methods for synthesizing any stereoisomer of E6020. Thus there is provided herein a method for preparing a compound having the structure:

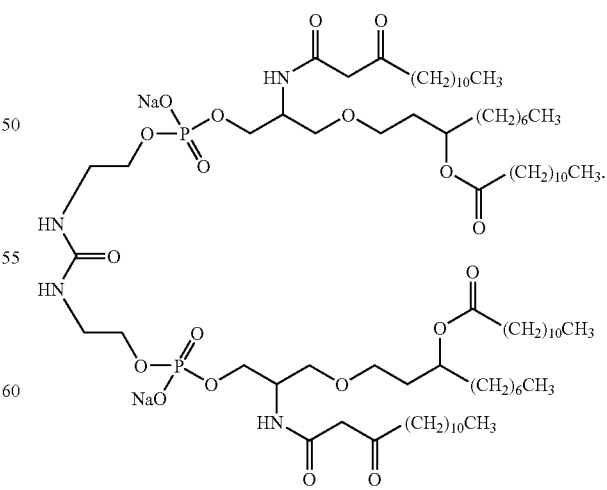

These compounds are useful as immunological adjuvants when co-administered with antigens such as vaccines for bacterial and viral diseases. The present invention also provides synthetic intermediates useful for preparing E6020 and stereoisomers thereof.

BRIEF DESCRIPTIONS OF THE FIGURES

DEFINITIONS

Figure 1:
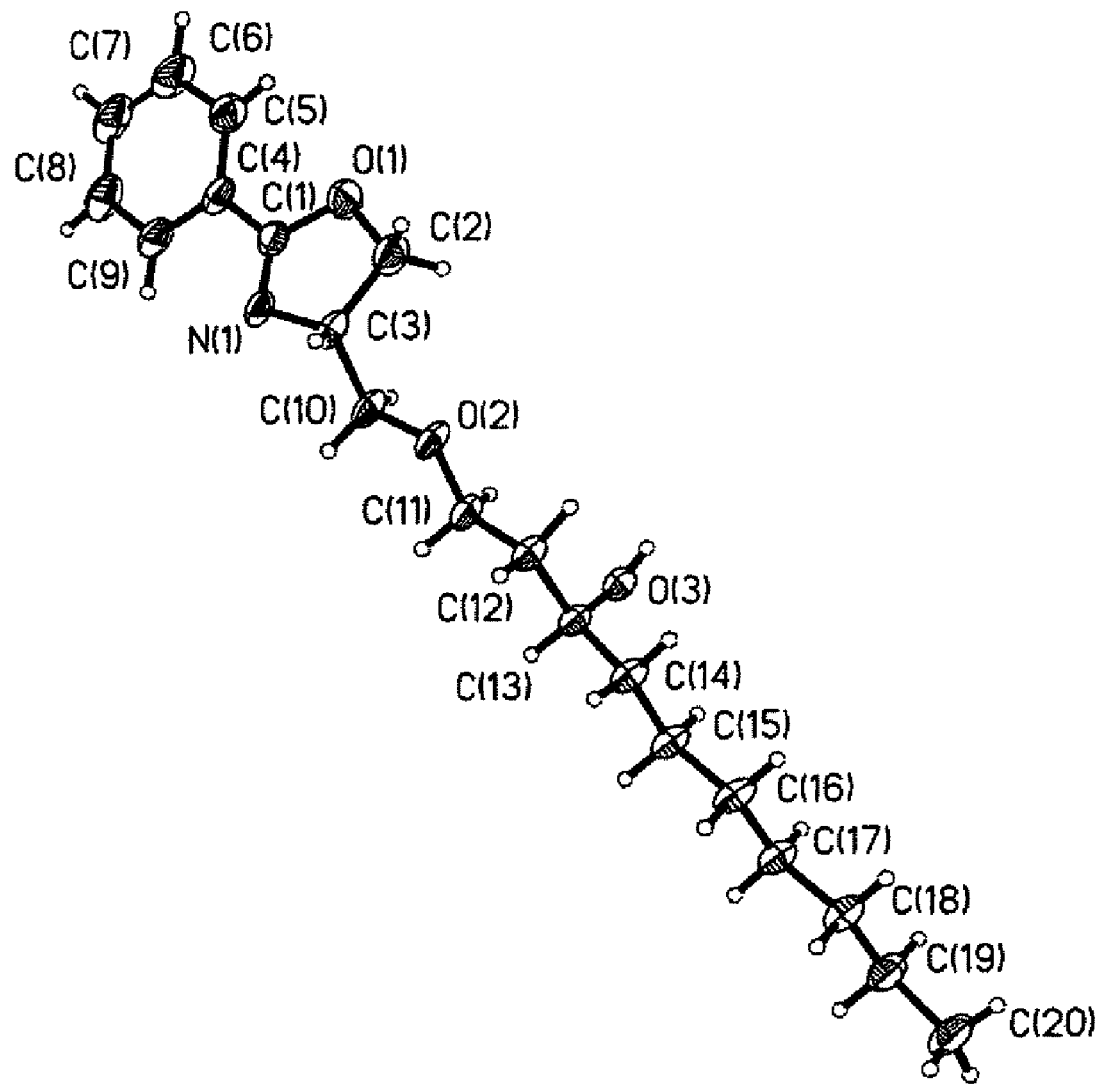
FIG. 1 depicts the structure of crystalline ER-8016158.

In accordance with the present invention and as used herein, the following terms are defined with the following meanings, unless explicitly stated otherwise.

Certain compounds disclosed in the present invention, and definitions of specific functional groups are also described in more detail below. For purposes of this invention, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. By the term "protecting group", has used herein, it is meant that a particular functional moiety, e.g., O, S, P, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, phosphorous, and carbon protecting groups may be utilized.

For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether)), esters (e.g., formate, acetate, benzoate (Bz), trifluoroacetate, dichloroacetate, to name a few), carbonates, cyclic acetals and ketals. Protecting groups for phosphite oxygens and phosphate oxgens include, for example, alkyl phosphates/phosphites such as: methyl, ethyl; isopropyl; t-butyl; cyclohexyl; 1-adamantyl; and 2-trimethylsilylprop-2-enyl; alkenyl phosphates/phospites such as ethenyl and allyl; 2-substituted ethyl phosphates/phosphites such as: 2-cyanoethyl, 2-cyano-1,1-dimethylethyl, 2-(trimethylsilyl)ethyl, 2-(4-nitrophenyl) ethyl, 2-(phenylsulfonyl)ethyl, and 2-(benzylsulfonyl)ethyl; haloethyl phosphates/phosphites such as: 2,2,2-trichloroethyl, 2,2,2-trichloro-1,1-dimethylethyl, 2,2,2-tribromoethyl, 2,3-dibromopropyl, benzyl phosphates/phosphates such as: benzyl; 4-nitrobenzyl, 4-chlorobenzyl; 1-oxido-4-methoxy-2-picolyl, fluorenyl-9-methyl, 5-benzisoxazolylmethylene, $(C_6H_5)_2C=$; and phenyl phosphates/phosphites such as: phenyl; 4-nitrophenyl, and 4-chlorophenyl; and silyl phosphates/phosphites such as: trimethylsilyl.

In certain other exemplary embodiments, nitrogen protecting groups are utilized. These nitrogen protecting groups may be monovalent or divalent protecting groups such as, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Amine protecting groups such as Cbz, Boc, Fmoc, TROC, TMS-ethyloxycarbonyl, cyanoethyloxycarbonyl, allyloxycarbonyl or $(C_6H_5)_2C=$(diphenylmethylene) may also be mentioned. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

It is understood that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic, carbon and heteroatom substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment and prevention, for example of disorders, as described generally above. Examples of substituents include, but are not limited to, halo substituents, e.g. F; Cl; Br; or I; a hydroxyl group; a $C_1$-$C_6$ alkoxy group, e.g, —OCH$_3$, —OCH$_2$CH$_3$, or —OCH(CH$_3$)$_2$; a $C_1$-$C_6$ haloalkyl group, e.g., —CF$_3$; —CH$_2$CF$_3$; or —CHCl$_2$; $C_1$-$C_6$ alkylthio; amino; mono and dialkyl amino groups; —NO$_2$; —CN; a sulfate group, and the like. Additional examples of generally applicable substituents are illustrated by the specific embodiments shown in the Examples that are described herein.

The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

As used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms. In other embodiments, $C_{1-4}$, $C_{2-4}$, $C_{1-3}$ or $C_{3-6}$ alkyl are preferred.

In certain embodiments, the alkyl, alkenyl and alkynyl groups employed in the invention contain 1-20 aliphatic carbon atoms for alkyl groups and 2-20 carbon atoms for alkenyl and alkynyl groups. In certain other embodiments, the alkyl, alkenyl, and alkynyl groups employed in the invention contain 1-15 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —$CH_2$-cyclopropyl, cyclobutyl, —$CH_2$-cyclobutyl, cyclopentyl, —$CH_2$-cyclopentyl-n, cyclohexyl, —$CH_2$-cyclohexyl, cyclohexenylethyl, cyclohexanylethyl, norborbyl moieties and the like, which again, may bear one or more substituents.

The term "alkoxy" (or "alkyloxy"), or "thioalkyl" as used herein refers to an alkyl or cycloalkyl group, as previously defined, attached to the parent molecular moiety through an oxygen atom or through a sulfur atom. In certain embodiments, the alkyl or cycloalkyl group contains 1-20 aliphatic or alicyclic carbon atoms. In certain other embodiments, the alkyl or cycloalkyl group contains 1-10 aliphatic or alicyclic carbon atoms. In yet other embodiments, the alkyl, alkenyl, and alkynyl groups employed in the invention contain 1-8 aliphatic or alicyclic carbon atoms. In still other embodiments, the alkyl group contains 1-6 aliphatic or alicyclic carbon atoms. In yet other embodiments, the alkyl group contains 1-4 aliphatic or alicyclic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl or cycloalkyl, as defined herein. The term "dialkylamino" refers to a group having the structure —N(R')$_2$, wherein each occurrence of R' is independently alkyl or cycloalkyl, as defined herein. The term "aminoalkyl" refers to a group having the structure NH$_2$R'—, wherein R' is alkyl or cycloalkyl, as defined herein. In certain embodiments, the alkyl group contains 1-20 aliphatic or alicyclic carbon atoms. In certain other embodiments, the alkyl or cycloalkyl group contains 1-10 aliphatic or alicyclic carbon atoms. In yet other embodiments, the alkyl, alkenyl, and alkynyl groups employed in the invention contain 1-8 aliphatic or alicyclic carbon atoms. In still other embodiments, the alkyl or cycloalkyl group contains 1-6 aliphatic or alicyclic carbon atoms. In yet other embodiments, the alkyl or cycloalkyl group contains 1-4 aliphatic or alicyclic carbon atoms. Examples of alkylamino include, but are not limited to, methylamino, ethylamino, iso-propylamino and the like.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. It will also be appreciated that aryl and heteroaryl moieties, as defined herein may be attached via an alkyl or heteroalkyl moiety and thus also include -(alkyl)aryl, -(heteroalkyl)aryl, -(heteroalkyl)aryl, and -(heteroalkyl)heteroaryl moieties. Thus, as used herein, the phrases "aryl or heteroaryl" and "aryl, heteroaryl, -(alkyl)aryl, -(heteroalkyl) aryl, -(heteroalkyl)aryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl and the like. In certain embodiments of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the substituents generally described above. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other alicyclic, heteroalicyclic or heterocyclic moieties, may optionally be substituted with one or more of the substituents generally described above. An analogous convention applies to other generic terms such as "cycloalkenyl", "cycloalkynyl" and the like. Additionally, it will be appreciated that any of the alicyclic or heteroalicyclic moieties described above and herein may comprise an aryl or heteroaryl moiety fused thereto. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be branched or linear unbranched. In certain embodiments, heteroaliphatic moieties are substituted by independent replacement of one or more of the hydrogen atoms thereon with one or more of the substituents generally described above. Additional examples of generally applicable substituents are illustrated by the specific embodiments shown in the Examples that are described herein.

The term "heteroalicyclic", as used herein, refers to compounds which combine the properties of heteroaliphatic and cyclic compounds and include but are not limited to saturated and unsaturated mono- or polycyclic heterocycles such as morpholino, pyrrolidinyl, furanyl, thiofuranyl, pyrrolyl etc., which are optionally substituted with one or more functional groups, as defined herein.

Additionally, it will be appreciated that any of the alicyclic or heteroalicyclic moieties described above and herein may comprise an aryl or heteroaryl moiety fused thereto. Additional examples of generally applicable substituents are illustrated by the specific embodiments shown in the Examples that are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a substituted or unsubstituted aryl or heteroaryl ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one or more of the hydrogen atoms thereon with one or more of the substituents generally described above. Additional examples or generally applicable substituents are illustrated by the specific embodiments shown in the Examples that are described herein.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heteroalicyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aryl", "heteroaryl" and the like encompass both substituted and unsubstituted groups.

Further, E6020 contains asymmetric carbon atoms and hence can exist as stereoisomers, both enantiomers and diastereomers. One of ordinary skill in the art will recognize that the inventive method may be adapted to the preparation of any of all possible stereoisomers of E6020. While the examples provided herein disclose the preparation of a particular isomer, methods for preparing other stereoisomers of E6020 are considered to fall within the scope of the present invention.

DETAILED DESCRIPTION

In one aspect, the present invention provides a method for synthesizing TLR-4 receptor agonist E6020 having the structure:

E6020

E6020 is a potent TLR-4 receptor agonist, and thus the compound is useful as an immunological adjuvant when co-administered with antigens such as vaccines for bacterial and viral diseases. For example, E6020 may be used in combination with any suitable antigen or vaccine component, e.g., an antigenic agent selected from the group consisting of antigens from pathogenic and non-pathogenic organisms, viruses, and fungi. As a further example, E6020 may be used in combination with proteins, peptides, antigens and vaccines which are pharmacologically active for disease states and conditions such as smallpox, yellow fever, cancer, distemper, cholera, fowl pox, scarlet fever, diphtheria, tetanus, whooping cough, influenza, rabies, mumps, measles, foot and mouth disease, and poliomyelitis. In certain embodiments, E6020 and the antigen are each present in an amount effective to elicit an immune response when administered to a host animal, embryo, or ovum vaccinated therewith.

In another aspect, the invention encompasses methods for synthesizing any stereoisomer of endotoxin agonist E6020. Thus there is provided herein a method for preparing a compound having the structure:

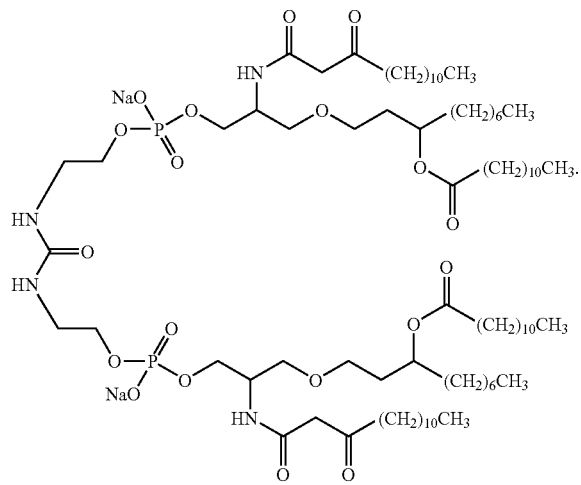

I. Preparation of Phosphoric Acid Ester Ureido Dimer

In certain embodiments, the inventive method comprises steps of:

(a) reacting a compound having the structure:

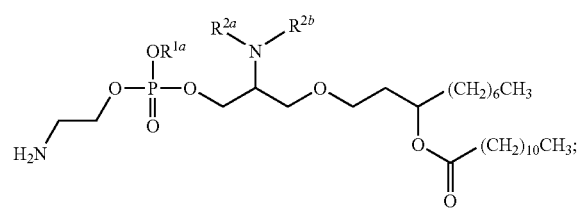

(1)

wherein $R^{1a}$ is alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, aryl, heteroaryl, a phosphite oxygen protecting group, or a phosphate oxygen protecting group; and $R^{2a}$ and $R^{2b}$ are each independently hydrogen or a suitable nitrogen protecting group, or $R^{2a}$ and $R^{2b}$, taken together, form a 5- or 6-membered heterocyclic ring; wherein $R^{2a}$ and $R^{2b}$ are not simultaneously hydrogen;

with phosgene under suitable conditions to effect formation of a ureido dimer having the structure:

(2)

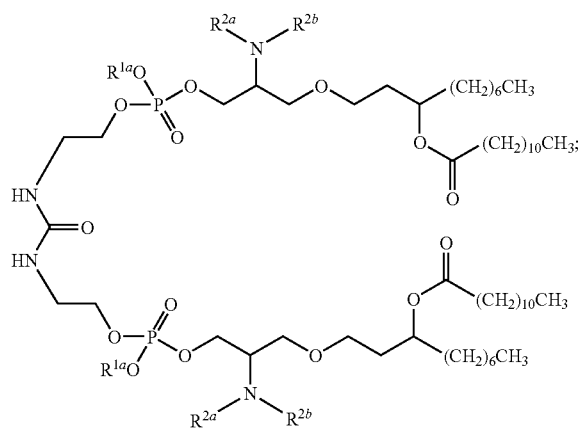

(b) deprotecting ureido dimer (2) formed in step (a) under suitable conditions to effect formation of a partially deprotected dimer (3) having the structure:

(3)

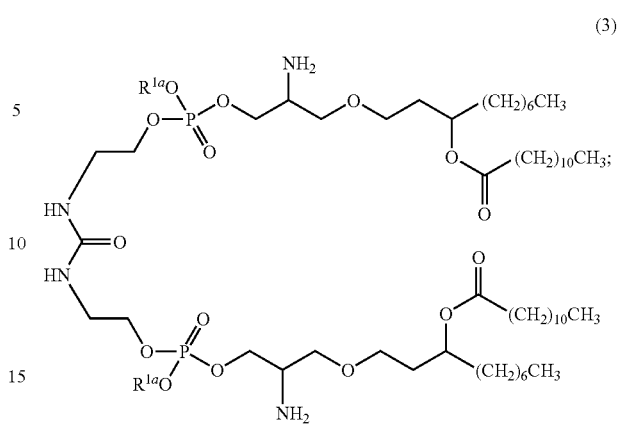

(c) reacting the partially deprotected dimer formed in step (b) with a suitable reagent under suitable conditions to effect formation of a protected dimer (4) having the structure:

(4)

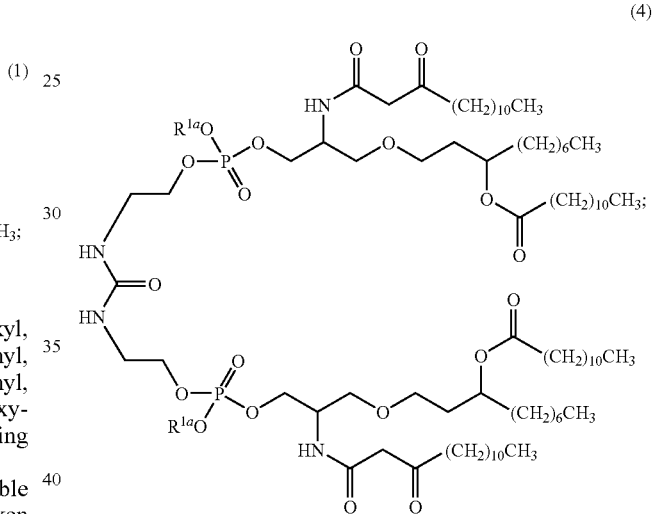

and (d) treating the dimer formed in step (c) with one or more suitable reagents under suitable conditions to effect formation of a sodium salt having the structure:

(5)

In certain embodiments, compounds 1-5 above have the following stereochemistry:
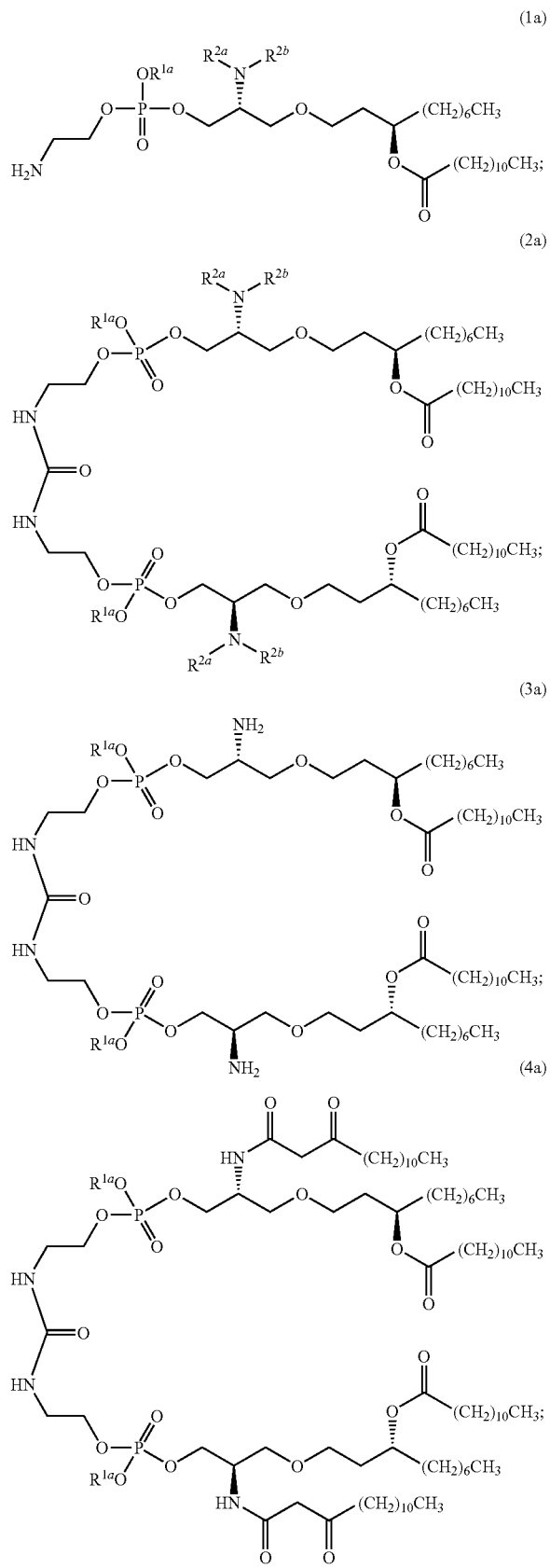
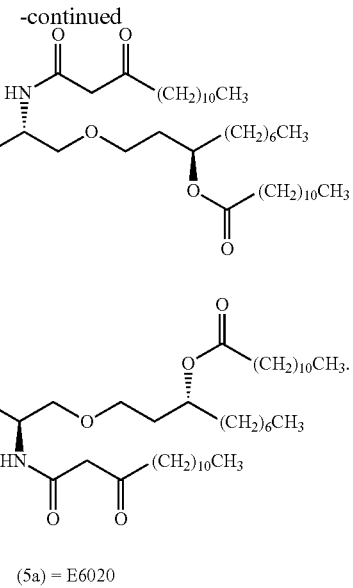
(5a) = E6020
In yet other embodiments, the step of treating the dimer formed in step (c) with one or more suitable reagents under suitable conditions leads to the formation of a compound having the structure:
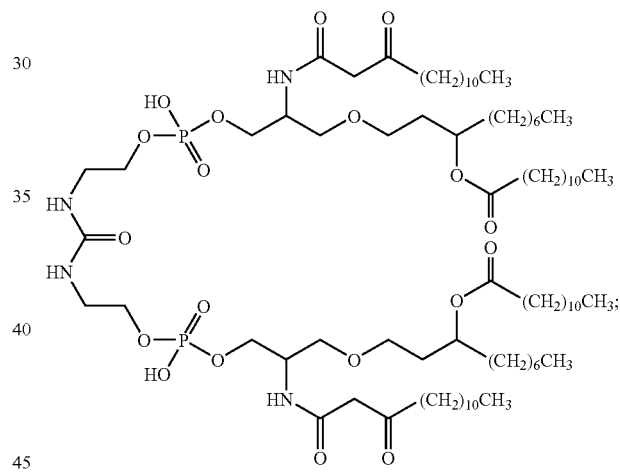
which is then purified to yield the corresponding di-sodium salt:
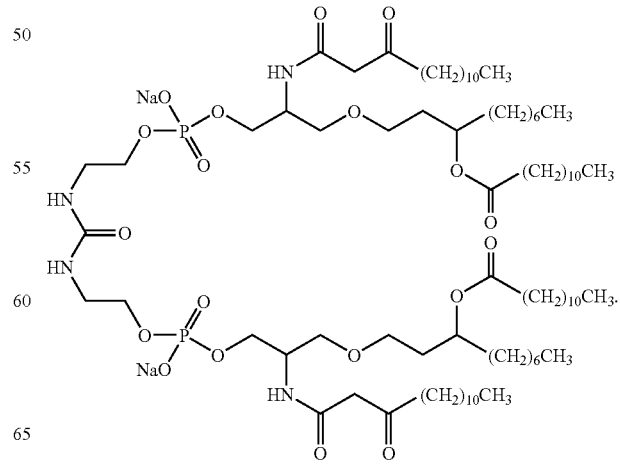

In certain embodiments, each occurrence of $R^{1a}$ is independently hydrogen, a $C_1$-$C_6$ alkyl group, a $C_3$-$C_6$ alkenyl group, a $C_3$-$C_6$ alkynyl group, or a phosphite oxygen protecting group or phosphate oxygen protecting group. In certain exemplary embodiments, each $R^{1a}$ is allyl.

In certain embodiments, $R^{2a}$ and $R^{2b}$ are each independently hydrogen, alkyl, alkenyl, —C(=O)$R^x$, —C(=O)O$R^x$, —S$R^x$, SO$_2R^x$, or $R^{2a}$ and $R^{2b}$, taken together form a moiety having the structure =C$R^xR^y$, wherein $R^{2a}$ and $R^{2b}$ are not simultaneously hydrogen and $R^x$ and $R^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^A$ or —Z$R^A$, wherein Z is —O—, —S—, —N$R^B$, wherein each occurrence of $R^A$ and $R^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, $R^{2a}$ is hydrogen and $R^{2b}$ is —C(=O)O$R^x$, wherein $R^x$ is substituted or unsubstituted lower alkyl. In certain other exemplary embodiments, $R^{2a}$ is hydrogen and $R^{2b}$ is —C(=O)OtBu.

In certain embodiments, the reaction conditions in step (a) comprise phosgene in a suitable solvent. In certain exemplary embodiments, the solvent is CH$_2$Cl$_2$, toluene or combination thereof. In certain embodiments, the reaction conditions in step (a) additionally comprise a weak base. In certain exemplary embodiments, the weak base is aqueous NaHCO$_3$.

In certain embodiments, the deprotection reaction conditions in step (b) comprise a strong acid in a suitable solvent. In certain exemplary embodiments, the solvent is CH$_2$Cl$_2$. In certain other exemplary embodiments, $R^{2a}$ is hydrogen, $R^{2b}$ is —C(=O)OtBu and the strong acid is TFA.

In certain embodiments, the reagent of step (c) is a 3-oxo-tetradecanoic acid derivative. As used herein, "carboxylic acid derivative" (e.g., 3-oxo-tetradecanoic or dodecanoic acid derivative) refers to a compound of structure RC(=O)X where R is the carboxyl radical and X is a chemical group suitable to effect formation of an amide via reaction with a primary amine, or that can be chemically transformed to effect formation of an amide via reaction with a primary amine. In certain embodiments, X is halogen, hydroxyl, —OR, —SH, —SR or —C(halo)$_3$; where R is alkyl or aryl. In certain exemplary embodiments, the reagent is 3-oxo-tetradecanoic acid. In certain embodiments, the reagent of step (c) is 3-oxo-tetradecanoic acid and and the reaction conditions for reacting the deprotected dimer with the reagent comprise a base. In certain embodiments, the base is 1-hydroxybenzotriazole. In certain embodiments, the base is Hunig's base. In certain embodiments, the reaction conditions of step (c) comprise a carboxylic acid activating reagent such as DCC. In certain embodiments, the carboxylic acid activating reagent is 1-[3-(dimethylamino)propyl]-3-ethylcarbodiimide. In certain embodiments, the carboxylic acid activating reagent is HBTU.

In certain other embodiments, each occurrence of $R^{1a}$ is allyl, and the reaction conditions in step (d) comprise Pd(PPH$_3$)$_4$ in a suitable solvent. In certain exemplary embodiments, the treating conditions in step (d) further comprise triphenyl phosphine and phenylsilane. In certain exemplary embodiments, the solvent is THF.

In still other embodiments, purification of the compound having the structure:

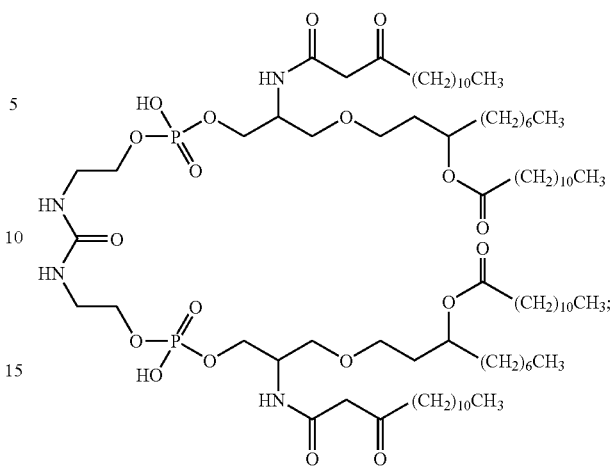

comprises chromatographic separation and treatment with a base. In certain exemplary embodiments, the purification process comprises (i) ion exchange chromatography, (ii) C-4 Kromasil elution and (iii) treatment with aqueous NaOAc. In certain exemplary embodiments, the purification process comprises (i) Biotage KP-silica chromatography, (ii) Biotage KP HS-C18 chromatography and (iii) treatment with aqueous NaOAc.

II. Method for Preparing Intermediate 1

In certain exemplary embodiments, the compound having the structure:

(1)

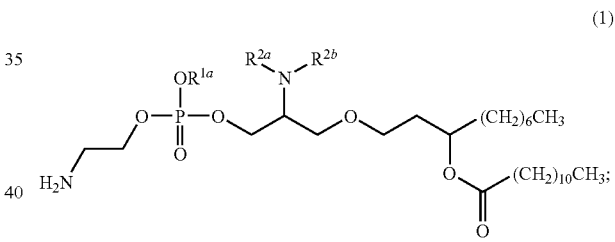

wherein $R^{1a}$ is hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, aryl, heteroaryl or a phosphite oxygen protecting group or phosphate oxygen protecting group; and $R^{2a}$ and $R^{2b}$ are each independently hydrogen or a suitable nitrogen protecting group, or $R^{2a}$ and $R^{2b}$, taken together, form a 5- or 6-membered heterocyclic ring; wherein $R^{2a}$ and $R^{2b}$ are not simultaneously hydrogen;

is prepared by a process comprising steps of:

(a) reacting an alcohol having the structure:

(6)

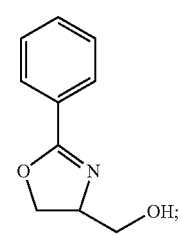

with a suitable partially protected diol having the structure:

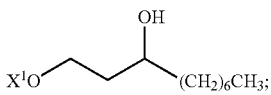
(7)

wherein —OX$^1$ represents a suitable leaving group;
to form an alcohol having the structure:

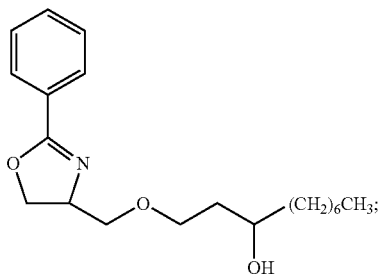
(8)

(b) reacting alcohol 8 with a suitable dodecanoic acid derivative under suitable conditions to form an ester having the structure:

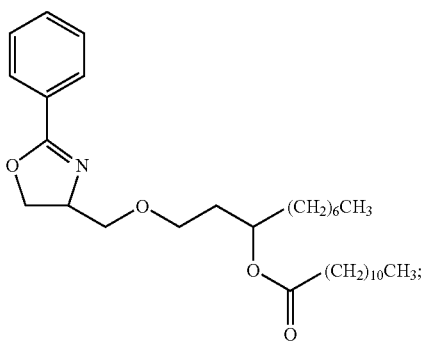
(9)

(c) deprotecting ester 9 under suitable conditions to form a hydroxyl amine having the structure:

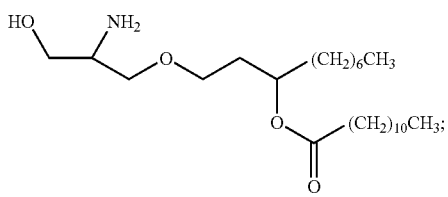
(10)

(d) partially protecting hydroxyl amine 10 suitable conditions to form an alcohol having the structure:

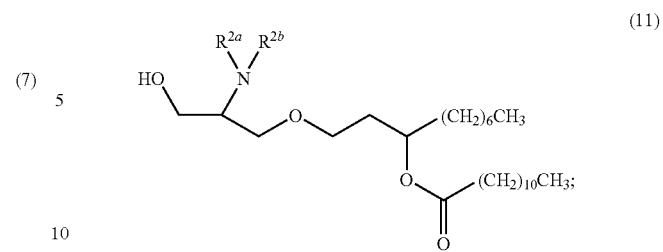
(11)

wherein R$^{2a}$ and R$^{2b}$ are as defined above;

(e) treating alcohol 11 with one or more suitable reagents under suitable conditions to effect formation of a phosphoric acid ester having the structure:

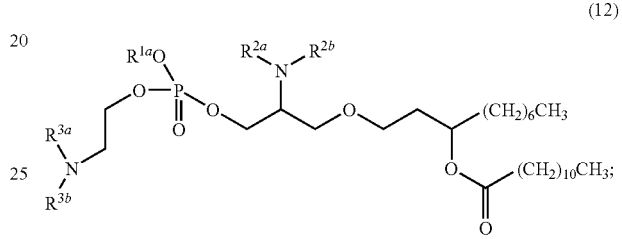
(12)

wherein R$^{1a}$ is hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, aryl or heteroaryl, a phosphite oxygen protecting group or phosphate oxygen protecting group; and R$^{3a}$ and R$^{3b}$ are each independently hydrogen or a suitable nitrogen protecting group, or R$^{3a}$ and R$^{3b}$, taken together, form a 5- or 6-membered heterocyclic ring; wherein R$^{31}$ and R$^{3b}$ are not simultaneously hydrogen; and (f) partially deprotecting 12 under suitable conditions to effect formation of amine 1:

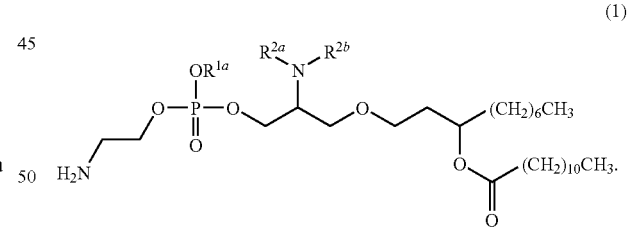
(1)

In certain embodiments, each occurrence of R$^{1a}$ is independently hydrogen, a C$_1$-C$_6$ alkyl group, a C$_3$-C$_6$ alkenyl group, a C$_3$-C$_6$ alkynyl group, or a phosphite oxygen protecting group or phosphate oxygen protecting group. In certain exemplary embodiments, each occurrence of R$^{1a}$ is allyl.

In certain embodiments, R$^{2a}$ and R$^{2b}$ are each independently hydrogen, alkyl, alkenyl, —C(=O)R$^x$, —C(=O)OR$^x$, —SR$^x$, SO$_2$R$^x$, or R$^{2a}$ and R$^{2b}$, taken together form a moiety having the structure =CR$^x$R$^y$, wherein R$^{2a}$ and R$^{2b}$ are not simultaneously hydrogen and R$^x$ and R$^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)R$^A$ or —ZR$^A$, wherein Z is —O—, —S—, —NR$^B$, wherein each occurrence of R$^A$ and R$^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, R$^{2a}$ is hydrogen and R$^{2b}$ is —C(=O)OR$^x$, wherein R$^x$ is substituted or unsubstituted lower alkyl. In certain other exemplary embodiments, R$^{2a}$ is hydrogen and R$^{2b}$ is —C(=O)OtBu.

In certain exemplary embodiments, X$^1$ is tosyl.

In certain embodiments, the dodecanoic acid derivative of step (b) is dodecanoic acid. In certain embodiments, the reagent of step (b) is dodecanoic acid and and the reaction conditions for reacting alcohol 8 comprise a base. In certain embodiments, the base is 4-dimethylaminopyridine (DMAP). In certain embodiments, the reaction conditions of step (b) comprise a carboxylic acid activating reagent such as DCC. In certain embodiments, the carboxylic acid activating reagent is 1-[3-(dimethylamino)propyl]-3-ethylcarbodiimide.

In certain embodiments, the deprotection reaction conditions of step (c) comprise catalytic hydrogenolysis and a suitable solvent. In certain exemplary embodiments, the deprotection reaction conditions of step (c) comprise H$_2$ and Pd/C. In certain exemplary embodiments, the solvent is isopropylalcohol (IPA).

In certain other exemplary embodiments, R$^{2a}$ is hydrogen and R$^{2b}$ is —C(=O)OtBu and the reaction conditions of step (d) comprise di-tert-butyldicarbonate and a suitable solvent. In certain embodiments, the solvent is an alcohol. In certain exemplary embodiments, the solvent is isopropylalcohol (IPA).

In certain embodiments, step (e) comprises:
(i) in situ formation of a phosphoramidous acid ester having the structure:

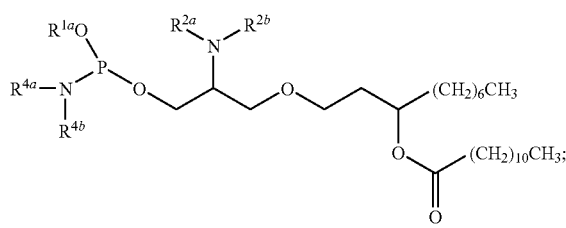

(13)

wherein R$^{4a}$ and R$^{4b}$ are independently lower alkyl; and
(ii) in situ formation of a phosphorous acid ester having the structure:

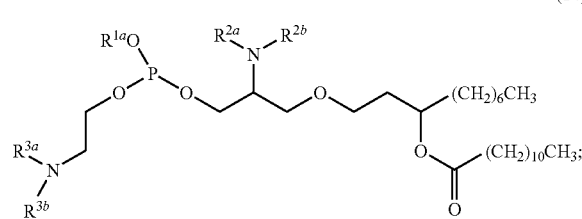

(14)

wherein R$^{1a}$, R$^{2a}$, R$^{2b}$, R$^{3a}$ and R$^{3b}$ are as defined above.

In certain other embodiments, the treating step (e) comprises a phosphorylating agent, and leads to the in situ formation of phosphoramidous acid ester 13. In certain exemplary embodiments, the phosphorylating agent is allyl tetraisopropylphosphorodiamidite in the presence of a dialkyl amine. In certain other embodiments, the treating step (e) comprises pyridinium trifluoroacetate. In certain exemplary embodiments, the dialkyl amine is diidopropylamine and the phosphoramidous acid ester 13 has the structure:

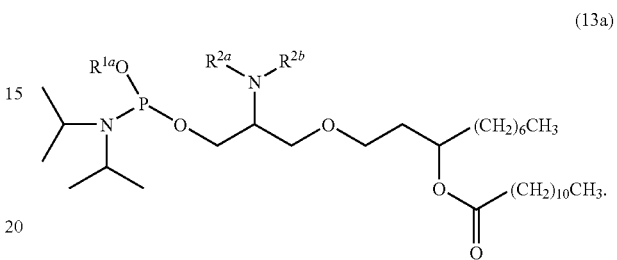

(13a)

In certain embodiments, the treating step (e) comprises in situ formation of phosphoramidous acid ester 13, followed by reaction with a protected ethanolamine having the structure:

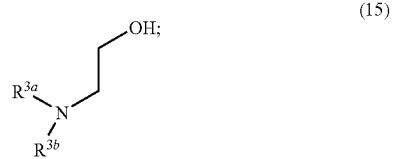

(15)

wherein R$^{3a}$ and R$^{3b}$ are each independently hydrogen or a suitable nitrogen protecting group, or R$^{31}$ and R$^{3b}$, taken together, form a 5- or 6-membered heterocyclic ring; wherein R$^{3a}$ and R$^{3b}$ are not simultaneously hydrogen. In certain exemplary embodiments, R$^{31}$ and R$^{3b}$ are each independently hydrogen, alkyl, alkenyl, —C(=O)R$^x$, —C(=O)OR$^x$, —SR$^x$, SO$_2$R$^x$, or R$^{3a}$ and R$^{3b}$, taken together form a moiety having the structure =CR$^x$R$^y$, wherein R$^{3a}$ and R$^{3b}$ are not simultaneously hydrogen and R$^x$ and R$^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)R$^A$ or —ZR$^A$, wherein Z is —O—, —S—, —NR$^B$, wherein each occurrence of R$^A$ and R$^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, R$^{3a}$ is hydrogen and R$^{3b}$ is —C(=O)OR$^x$, wherein R$^x$ is arylakyl. In certain other exemplary embodiments, R$^{3a}$ is hydrogen and R$^{3b}$ is —C(=O)OR$^x$, wherein R$^x$ is 9-fluorenylmethyl (i.e., R$^{3b}$ is Fmoc).

In certain exemplary embodiments, the treating step (e) comprises in situ reaction of phosphoramidous acid ester 13 with protected ethanolamine 15, where R$^{3a}$ is hydrogen and R$^{3b}$ is Fmoc, and the reaction conditions comprise acetic acid and pyridinium trifluoroacetate.

In certain embodiments, the treating step (e) comprises in situ formation of phosphorous acid ester 14, followed by oxidation to form phosphoric acid ester 12:

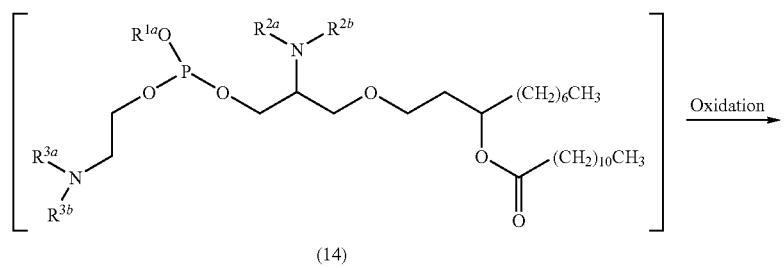

(14)

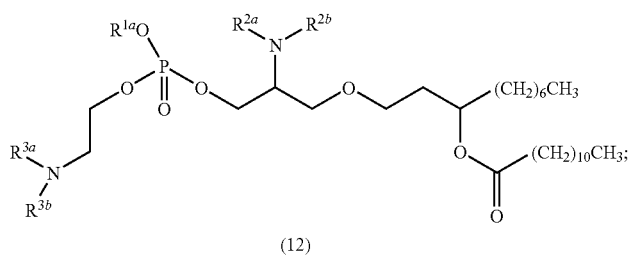

(12)

in the presence of a suitable oxidizing agent. In certain exemplary embodiments, the oxidizing agent is $H_2O_2$.

In certain embodiments, $R^{2a}$ is hydrogen and $R^{2b}$ is —C(=O)OtBu and the reaction conditions of step (f) comprise a dialkylamine and a suitable solvent. In certain exemplary embodiments, the dialkylamine is dimethyl amine. In certain other exemplary embodiments, the solvent is THF.

In certain embodiments, intermediates 6-13, 13a and 14 have the following stereochemistry:

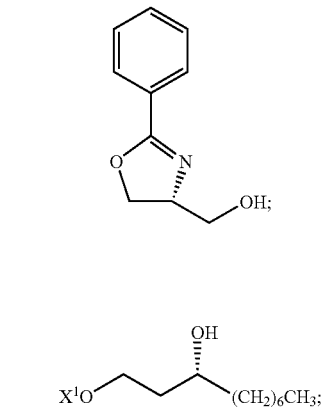

(6a)

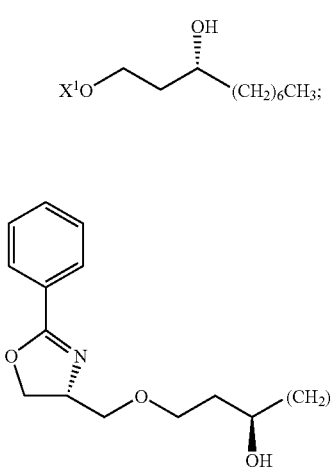

(7a)

(8a)

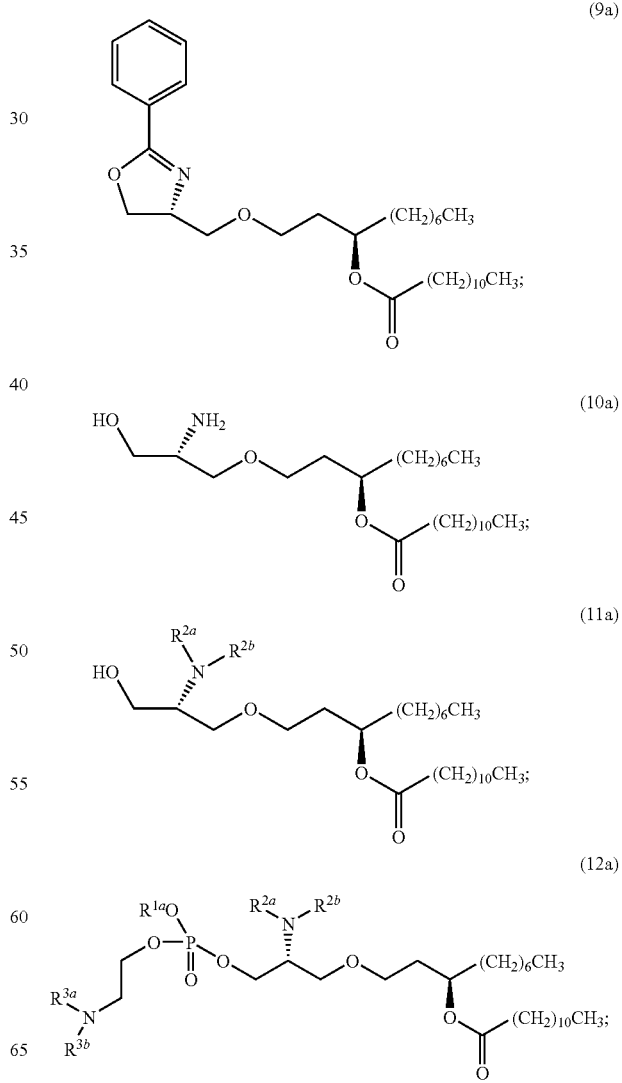

(9a)

(10a)

(11a)

(12a)

-continued

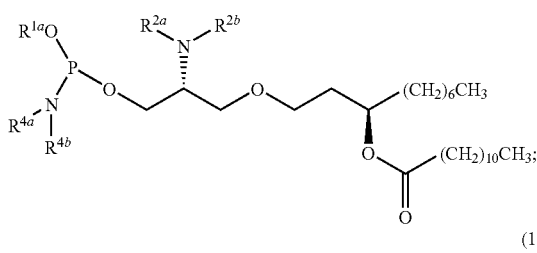

(13a)

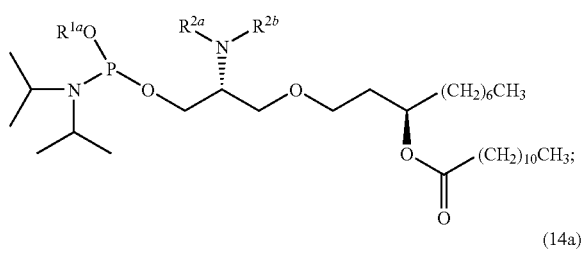

(13b)

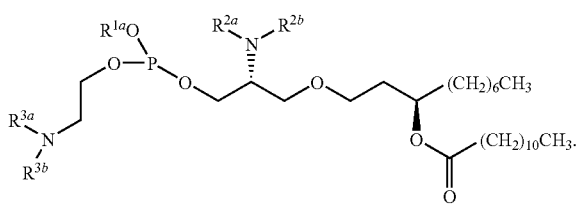

(14a)

Synthetic Overview

The practitioner has a a well-established literature of phospholipid chemistry to draw upon, in combination with the information contained herein, for guidance on synthetic strategies, protecting groups, and other materials and methods useful for the synthesis of E6020 and stereoisomers thereof.

The various patent documents and other references cited herein provide helpful background information on preparing certain monosaccharide starting materials. In particular, certain reagents and starting materials are described in U.S. Pat. Nos. 6,551,600; 6,290,973 and 6,521,776, the entirety of which are herein incorporated by reference.

Moreover, the practitioner is directed to the specific guidance and examples provided in this document relating to exemplary intermediates useful for the synthesis of E6020 and stereoisomers thereof.

The compounds discussed above in the synthesis of E6020 have heptyl and undecyl side chains. These side chains may have varying lengths by using appropriate reagents in the synthesis of E6020 analogs with different alkyl chain lengths. Accordingly, the invention relates to compounds having the following formula (15):

(15)

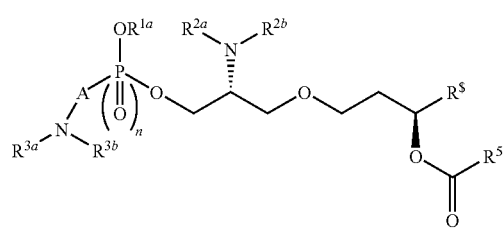

In formula (15), A is —$(CH_2)_x$—O— or a covalent bond, n is 0 or 1, and x ranges from 1 to 6. When A is —$(CH_2)_x$—O—, the methylene group is bonded to the nitrogen atom in $NR^{3a}R^{3b}$ and the oxygen is bound to the phosphorous atom in the phosphite or phosphate group. Preferably x ranges from 2 to 4 and most preferably 2. When n is 0, a compound of formula (15) contains a phosphite group. When n is 1, a compound of formula (15) contains a phosphate group.

$R^{1a}$ is hydrogen, a $C_1$-$C_6$ alkyl group, a $C_3$-$C_6$ alkenyl group, a $C_3$-$C_6$ alkynyl group, or a phosphite oxygen protecting group or phosphate oxygen protecting group. Such protecting groups are known in the art and an exemplary list is described above. A particularly preferred group $R^{1a}$ is an allyl group.

In formula (15), one of $R^{2a}$ and $R^{2b}$ is H and the other is a monovalent nitrogen protecting group; or $R^{2a}$ and $R^{2b}$ taken together are a divalent nitrogen protecting group. For $R^{3a}$ and $R^{3b}$, when A is —$(CH_2)$—O—, one of $R^{3a}$ and $R^{3b}$ is H and the other is a monovalent nitrogen protecting group or $R^{3a}$ and $R^{3b}$ taken together are a divalent nitrogen protecting group. When A is a covalent bond, $R^{3a}$ and $R^{3b}$ are independently selected from $C_1$-$C_6$ alkyl or taken together are —$(CH_2)_4$—, —$(CH_2)_5$—, or —$(CH_2)_2O(CH_2)_2$—. Preferably, when A is a covalent bond, $R^{3a}$ and $R^{3b}$ are $C_2$-$C_6$ alkyl groups such as ethyl, propyl or butyl and more preferably isopropyl groups.

In compounds of formula (15), the protecting group on the nitrogen linked to $R^{2a}$ and $R^{2b}$ can be removed under a first condition selected from acidic, basic, oxidative, and reductive conditions; and the protecting group on the nitrogen linked to $R^{3a}$ and $R^{3b}$ can be removed under a second condition selected from the remaining three conditions that are different from the first condition. Preferred nitrogen protecting group selected from the group consisting of Boc, Fmoc, TROC, TMS-ethyloxycarbonyl, cyanoethyloxycarbonyl, allyloxycarbonyl, $(C_6H_5)_2C=$, tetrachlorophthalimide, and azide. Generally speaking, there are four types of conditions which may be used to remove nitrogen protecting groups, acidic, basic, oxidation or reductive conditions. In a preferred embodiment, one nitrogen protective group is selectively removed under one of these four conditions and the other are removed using one of the remaining three conditions. In one embodiment the nitrogen protecting groups are respectively removed with mild acidic or mild basic conditions.

The nitrogen linked to $R^{2a}$ and $R^{2b}$ could be protected with a Boc group and the nitrogen linked to $R^{3a}$ and $R^{3b}$ could be protected with an Fmoc group or vice versa. The Boc group can be selectively removed under acidic conditions (methanesulfonic acid, trifluoroacetic acid, or formic acid in a solvent such as methylene chloride at room temperature). The Fmoc group could be selectively removed while using secondary amines like piperidine or dimethylamine in a solvent such as THF at room temperature.

Alternatively, the nitrogen linked to $R^{2a}$ and $R^{2b}$ could be protected with a Troc group and the nitrogen linked to with $R^{3a}$ and $R^{3b}$ could be protected with an Fmoc group or vice versa. The Fmoc group could be selectively removed under conditions described above and the Troc group could be cleaved under reducing conditions such as zinc in THF, water.

In another example, the nitrogen linked to $R^{2a}$ and $R^{2b}$ could be protected with a Troc group and the nitrogen linked to $R^{3a}$ and $R^{3b}$ could be protected with a Boc group or vice versa. The Troc group could be cleaved under reducing conditions such as zinc in THF, water and the Boc group could be selectively removed under conditions as described above.

$R^4$ is a $C_5$-$C_{12}$ alkyl group or a $C_5$-$C_{12}$ alkenyl group. $R^4$ is a $C_5$-$C_{12}$ alkyl group; preferably a $C_5$-$C_9$ alkyl group, more preferably a $C_7$ alkyl group, and most preferably an n-heptyl group.

$R^5$ is a $C_5$-$C_{15}$ alkyl group or a $C_5$-$C_{15}$ alkenyl group. $R^5$ is a $C_5$-$C_{15}$ alkyl group, preferably a $C_7$ to $C_{13}$, more preferably a $C_{11}$ alkyl group, and most preferably, n-undecyl.

Salts of the compounds of formula (15) may occur during synthesis or may also be made by reacting a compound of formula (I) with an acid or a base. Acid addition salts are preferred.

Preferred compounds of formula (15) are those (a) wherein A is —($CH_2$)$_2$—O—; n is 0; $R^4$ is a $C_7$ alkyl; and $R^5$ is a $C_{11}$ alkyl; (b) wherein A is —($CH_2$)$_2$—O—; n is 1; $R^4$ is a $C_7$ alkyl; and $R^5$ is a $C_{11}$ alkyl; (c) wherein A is a covalent bond, n is 0; $R^4$ is a $C_7$ alkyl; and $R^5$ is a $C_{11}$ alkyl; and (d) wherein A is a covalent bond, n is 0; $R^{3a}$ and $R^{3b}$ are each isopropyl; $R^4$ is a $C_7$ alkyl; and $R^5$ is a $C_{11}$ alkyl.

Such intermediates are useful in preparing E6020 analogs and precursors having the following formula (16):

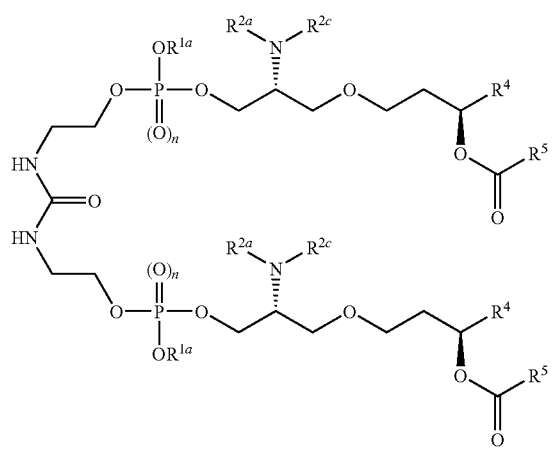

(16)

In formula (16), n is 0 or 1 as discussed above for formula (I). $R^{1a}$ is hydrogen, a $C_1$-$C_6$ alkyl group, a $C_2$-$C_6$ alkenyl group, a $C_2$-$C_6$ alkynyl group, a phosphite oxygen protecting group, or a phosphate oxygen protecting group. Preferred substituents for group $R^{1a}$ are the same as those discussed above. For example, one of $R^{2a}$ and $R^{2c}$ is H and the other is a monovalent nitrogen protecting group or —C(O)CH$_2$C(O)R$^6$; or $R^{2a}$ and $R^{2c}$ taken together are a divalent nitrogen protecting group. Preferable groups for $R^{2a}$ and $R^{2c}$ are the same as those described above for $R^{2a}$ and $R^{2b}$, except that one of $R^{2a}$ or $R^{2c}$ may also preferably be —C(O)CH$_2$C(O)R$^6$. $R^4$ is a $C_5$-$C_{12}$ alkyl group or a $C_5$-$C_{12}$ alkenyl group with the same preferred groups as in formula (15). $R^5$ and $R^6$ are independently a $C_5$-$C_{15}$ alkyl group or a $C_5$-$C_{15}$ alkenyl group with the preferred substituents being the same as those described above for $R^5$.

Preferred compounds of formula (16) are those (a) wherein n is 1, $R^4$ is a $C_7$ alkyl, and $R^5$ is a $C_{11}$ alkyl, wherein n is 1, $R^{1a}$ is allyl, $R^{2a}$ is hydrogen, $R^{2c}$ is Boc, $R^4$ is a $C_7$ alkyl, and $R^7$ is a $C_{11}$ alkyl; (c) wherein n is 1, $R^{2a}$ is hydrogen, $R^{2c}$ is —C(O)CH$_2$C(O)R$^6$, $R^4$ is a $C_7$ alkyl, $R^5$ is a $C_{11}$ alkyl, and $R^6$ is a $C_{11}$ alkyl; (d) wherein n is 0, $R^{1a}$ is allyl, $R^{2a}$ is hydrogen, $R^{2c}$ is Boc, $R^4$ is a $C_7$ alkyl, and $R^5$ is a $C_{11}$ alkyl; (e) wherein n is 1, $R^{1a}$ is allyl, $R^{2a}$ is hydrogen, $R^{2c}$ is hydrogen, $R^4$ is a $C_7$ alkyl, and $R^5$ is a $C_{11}$ alkyl; and (f) wherein n is 0, $R^{1a}$ is allyl, $R^{2a}$ is hydrogen, $R^{2c}$ is —C(O)CH$_2$C(O)R$^6$, $R^4$ is a $C_7$ alkyl, $R^5$ is a $C_{11}$ alkyl, and $R^6$ is a $C_{11}$ alkyl.

Salts of the compounds of formula (16) may occur during synthesis or may also be made by reacting a compound of formula (I) with an acid or a base. Acid addition salts are preferred.

The invention also includes compounds of formula (17):

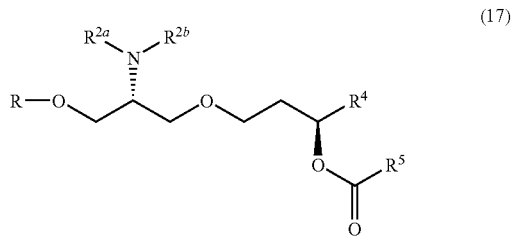

(17)

In formula (17), R is hydrogen or a $C_1$-$C_6$ alkyl group and preferably hydrogen. One $R^{2a}$ and $R^{2b}$ in formula (17) is H and the other is a monovalent nitrogen protecting group; or $R^{2a}$ and $R^{2b}$ taken together are a divalent nitrogen protecting group. The preferred groups for $R^{2a}$ and $R^{2b}$ are those discussed above for formula (15). $R^4$ is a $C_5$-$C_{12}$ alkyl group or a $C_5$-$C_{12}$ alkenyl group and $R^5$ is a $C_5$-$C_{15}$ alkyl group or a $C_5$-$C_{15}$ alkenyl group. The preferred groups for $R^4$ and $R^5$ are also those discussed above for formula (15).

Preferred compounds of formula (17) include those (a) wherein R is hydrogen, $R^{2a}$ and $R^{2b}$ are hydrogen, $R^4$ is a $C_7$ alkyl, and $R^5$ is a $C_{11}$ alkyl; and (b) wherein R is hydrogen, $R^{2a}$ is hydrogen, $R^{2b}$ is a nitrogen protecting group, $R^4$ is a $C_7$ alkyl, and $R^5$ is a $C_{11}$ alkyl.

The invention also includes compounds of formula (18):

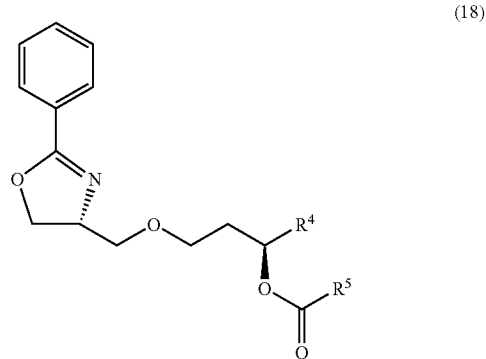

(18)

In formula (18), $R^4$ is a $C_5$-$C_{12}$ alkyl group or a $C_5$-$C_{12}$ alkenyl group; and $R^5$ is a $C_5$-$C_{15}$ alkyl group or a $C_5$-$C_{15}$ alkenyl group. Preferred groups for $R^6$ and $R^7$ are those discussed above. A preferred compound of formula (18) is ER-819509.

Examples of synthetic methods for practicing the invention are provided below, as detailed in Schemes 1-5, and in the Exemplification herein. It will be appreciated that the methods as described herein can be applied to each of the compounds as disclosed herein and equivalents thereof. Additionally, the reagents and starting materials are well known to those skilled in the art. Although the following schemes describe certain exemplary intermediates and protecting groups, it will be appreciated that the use of alternate starting materials, protecting groups and/or reagents will yield other intermediates, which are considered to fall within the scope of the present invention.

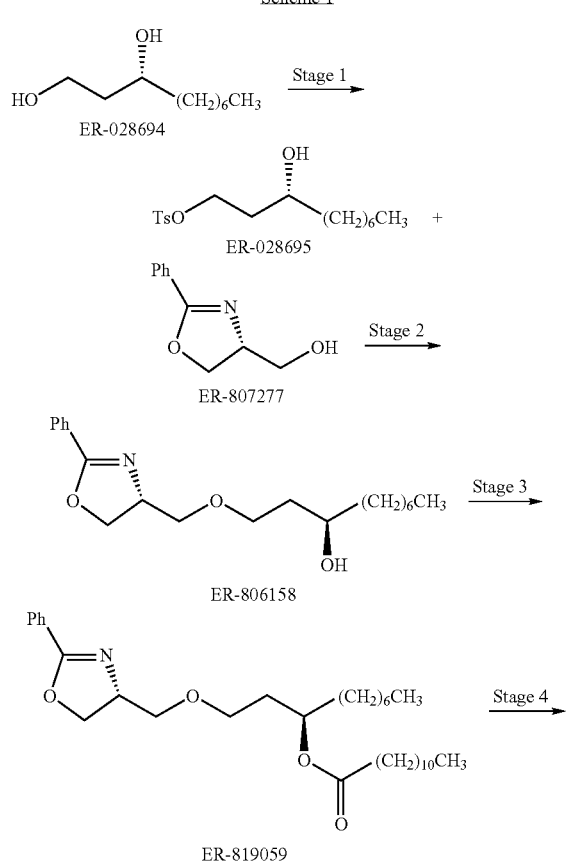

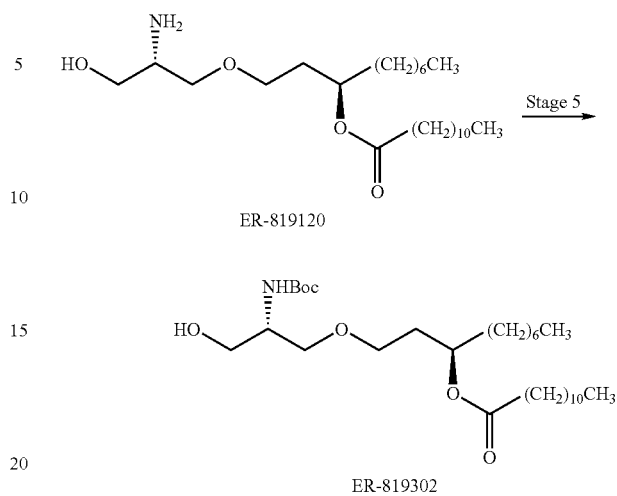

Stage 1: TsCl, Et₃N. Stage 2: NaHMDS, chromatography, crystalization.
Stage 3: Lauric acid, EDC, DMAP, CH₂Cl₂, chromatography.
Stage 4: H₂, 10% Pd/C, EtOH. Stage 5: Boc₂O, chromatography.

In certain exemplary embodiments of the present invention, preparation of the ester ER-819059 is achieved in three steps selectively functionalizing diol ER-028694 with a suitable group, thereby transforming the primary hydroxyl into a leaving group. For example, the primary hydroxyl of diol ER-028694 is tosylated to give the corresponding adduct ER-028695. Tosyl ester ER-028695 is then coupled with alcohol ER-807277 in the presence of a base, such as NaHMDS to give the corresponding ether ER-806158. Esterification of alcohol ER-806158 with lauric acid, followed by hydrogenolysis of the phenyl dihydrooxazole group leads to hydroxylamine ER-819120. Boc protection of the amino group gives ER-819302.

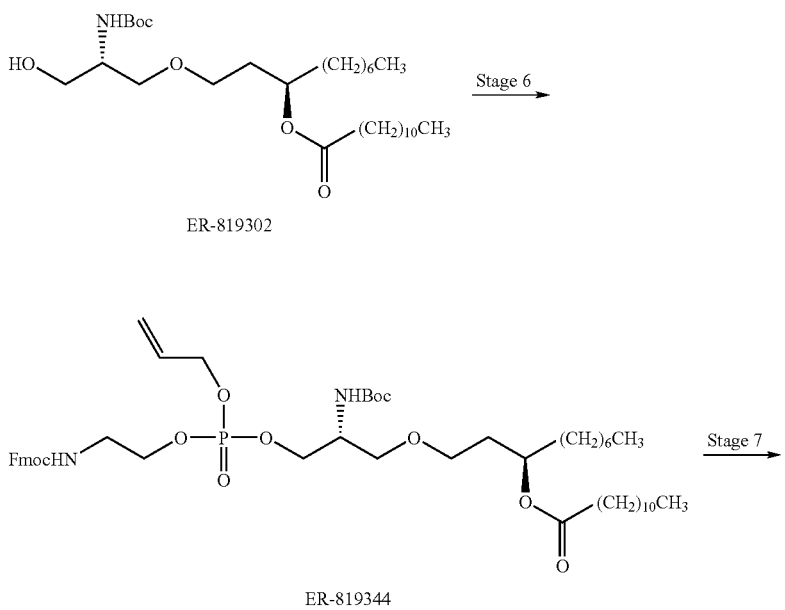

-continued
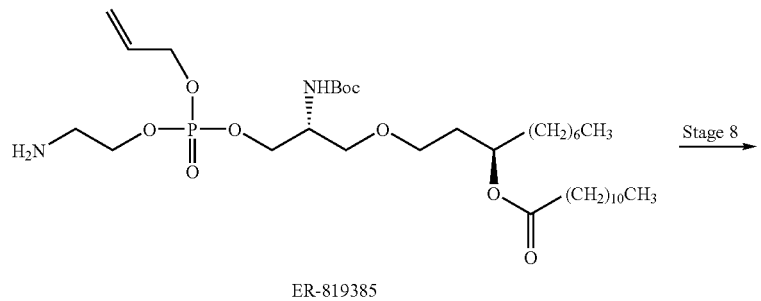
ER-819385
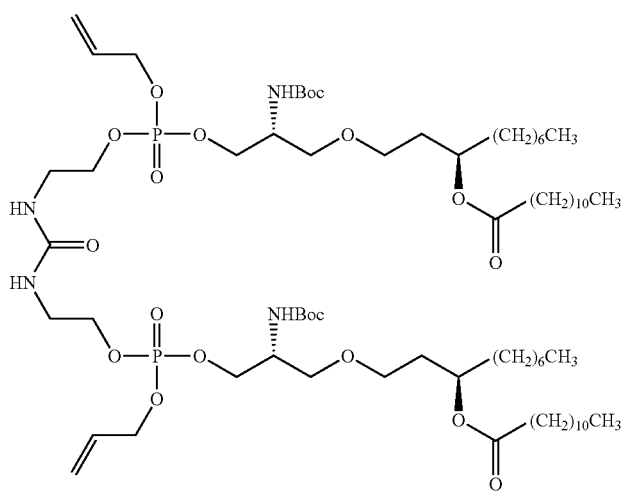
ER-819409
Stage 6: a. ((iPr)₂N)₂P(OAllyl), Py•TFA; b. HOAc; Py•TFA; FmocNH(CH₂)₂OH; c. H₂O₂, chromatography.
Stage 7: Me₂NH. Stage 8: 20% Phosgene in Toluene, NaHCO₃, chromatography.
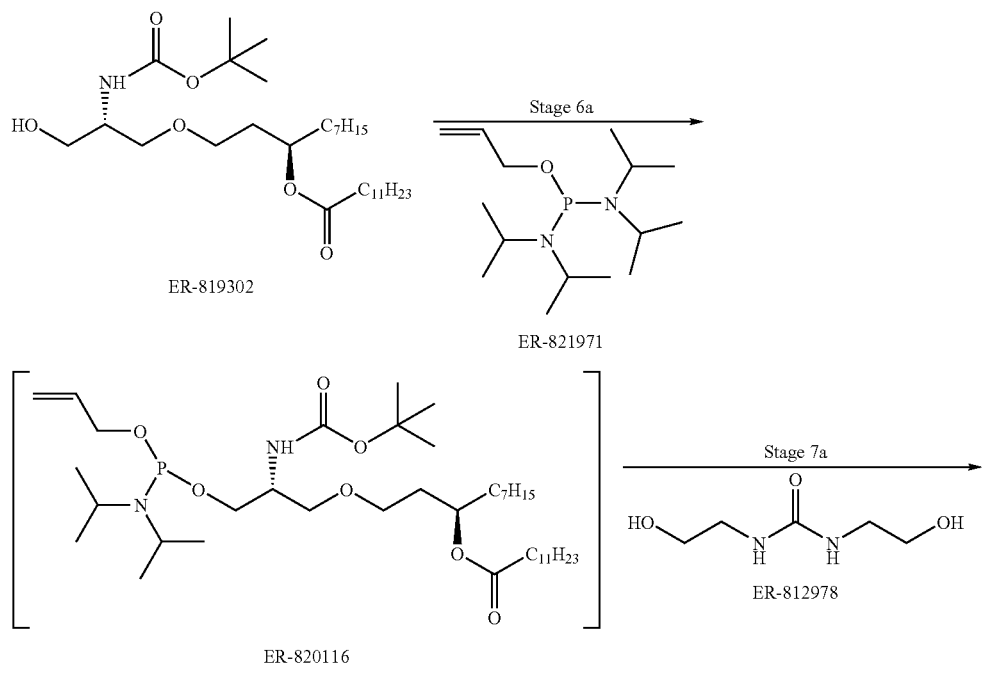

-continued
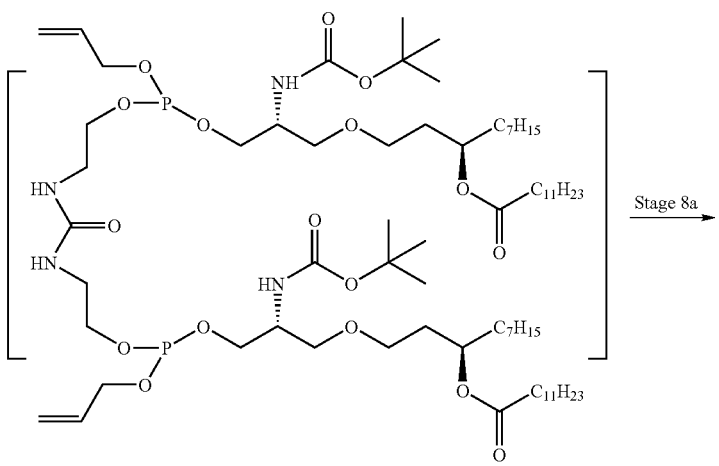
ER-821843 → Stage 8a
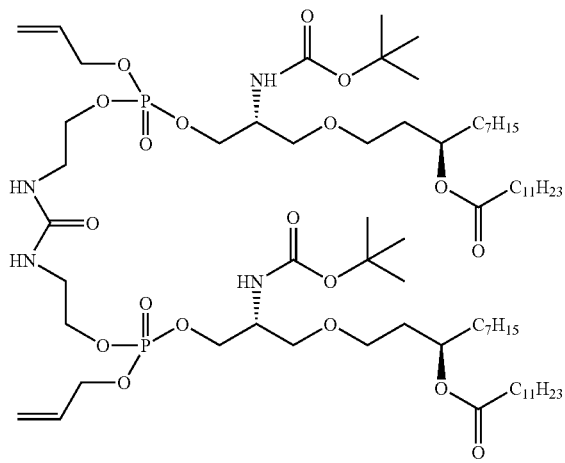
ER-819409
Stage 6a: pyrdinium trifluoroacetate, diisopropyl amine, Acetonitrile
Stage 7a: 2 eq. HOAc, 1.0 eq. Pyr-TFA
Stage 8a: -5-0° C., 30% aq. H$_2$O$_2$ followed by quench with NaHSO$_3$
Scheme 3
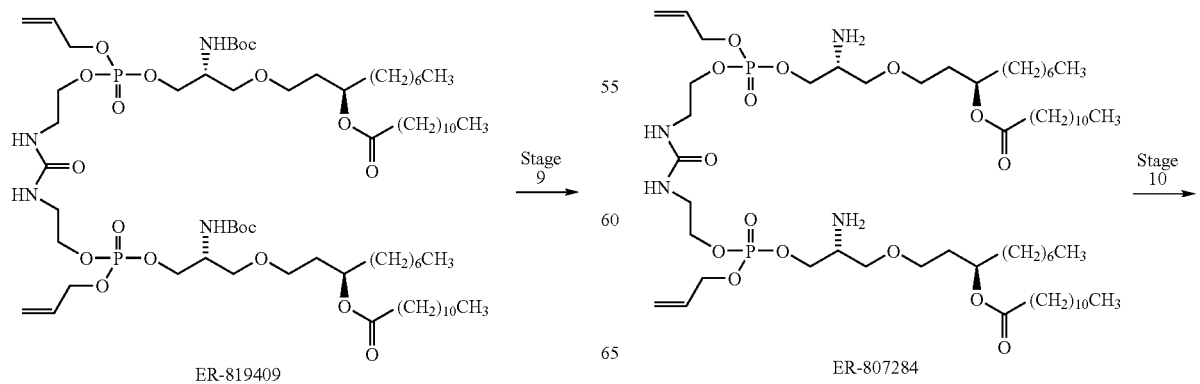
ER-819409 → Stage 9 → ER-807284 → Stage 10

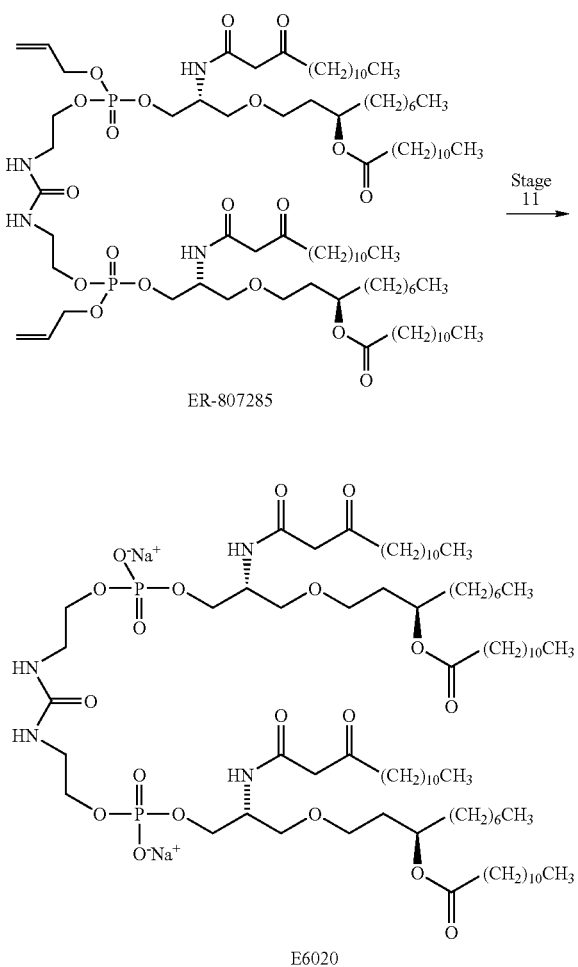

ER-807285

E6020

Stage 9: TFA. Stage 10: 3-Oxo-tetradecanoic acid, EDC, DMF.
Stage 11: Pd(PPh₃)₄, PhSiH₃.

Boc-protected ER-819302 may then be converted to E6020 in 6 steps, as outlined in Schemes 2 and 3. For example, phosphorylation of ER-819302 in the presence of bis(allyloxy)diisopropyl aminophosphine and diisopropylamine, followed by reaction in situ with FmocNH(CH$_2$)$_2$OH, and oxidation (e.g., hydrogen peroxide) leads to the formation of phosphorylated intermediate ER-819344, which, upon deprotection in suitable conditions (e.g., Me$_2$NH) leads to the formation of deprotected intermediate ER-819385. Reaction of ER-819385 with phosgene in suitable conditions (e.g., 20% phosgene in toluene in the presence of aqueous NaHCO$_3$) leads to the formation of diphosphoric acid ester ER-819409. Deprotection of the Boc-protected secondary amines on ER-819409 using an appropriate acid such as TFA provides the diamine intermediate ER-807284. Amidation of the free amines using 3-oxo-1-tetradecanoic acid in the presence of a coupling reagent such as EDC and DMAP provides the penultimate product ER-807285. Deprotection of the allyl-phosphate esters using a palladium (0) reagent such as palladium (0) tetrakistriphenylphosphine in the presence of excess triphenylphosphine and a proton source (phenylsilane) provides the desired, crude product that can be purified (e.g., suitable ion exchange chromatographic conditions, followed by treatment with aqueous NaOAc) to give the desired compound E6020.

It will be appreciated that each of the reactions described in Schemes 1, 2 and 3 above can be carried out using reagents and conditions as described for the synthesis of various types of exemplary intermediates described above, or they may be modified using other available reagents, protecting groups or starting materials. For example, a variety of urea formation conditions, phosphorylation and amine protecting/deprotecting conditions are well-known in the art and can be utilized in the method of the invention. See, generally, March, Advanced Organic Chemistry, 5$^{th}$ ed., John Wiley & Sons, 2001; and "Comprehensive Organic Transformations, a guide to functional group preparations", Richard C. Larock, VCH publishers, 1999; the entire contents of which are incorporated herein by reference and "Protective Groups in Organic Synthesis" Third Ed. Greene, T. W. and Wuts, P. G., Eds., John Wiley & Sons, New York: 1999, the entire contents of which are hereby incorporated by reference.

In summary, the present invention provides a synthesis of E6020 in significantly fewer and higher yielding steps than previously reported methods. The instant method affords the title compound in high overall yields and through a highly efficient route.

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXEMPLIFICATION

The compounds of this invention and their preparation can be understood further by the examples that illustrate some of the processes by which these compounds are prepared or used. It will be appreciated, however, that these examples do not limit the invention. Variations of the invention are considered to fall within the scope of the present invention as described herein and as hereinafter claimed.

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

Using the preparation of immunological adjuvant E6020 to exemplify, the following Examples encompass the synthesis of synthetic precursors of immunological adjuvant compounds using the methods and compounds of the present invention.

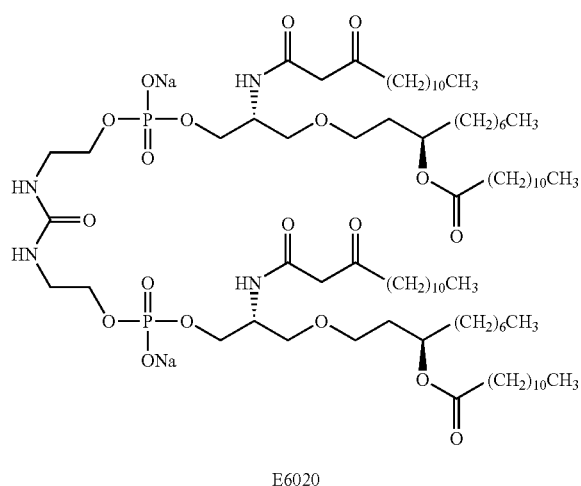

E6020

One of ordinary skill in the art would recognize that many analogs of E6020 are prepared by the methods and from the compounds of the present invention including, but not limited to, those analogs of E6020 described in U.S. Pat. Nos. 6,551,600; 6,290,973 and 6,521,776, the entirety of which are herein incorporated by reference. Accordingly, it will be appreciated that the synthetic methods described below, by way of example, do not limit the scope of the invention which is defined by the appended claims.

General Reaction Procedures

Unless mentioned specifically, reaction mixtures were stirred using a magnetically driven stirrer bar. An inert atmosphere refers to either dry argon or dry nitrogen. Reactions were monitored either by thin layer chromatography, by proton nuclear magnetic resonance or by high-pressure liquid chromatography (HPLC), of a suitably worked up sample of the reaction mixture.

Listed below are abbreviations used for some common organic reagents referred to herein:

ATP: Allyl tetraisopropylphosphorodiamidite
DMF: Dimethyl formamide
EA: Ethyl Acetate
EDC: 1-(3-Dimethylaminopropyl)-3-ethylcarbodiimide hydrochloride
HBTU: O-Benzotriazole-N,N,N',N'-tetramethyluronium-hexafluoro-phosphate
HOBT: 1-Hydroxybenzotriazole
IPA: Iso-propyl alcohol
MTBE: Methyl tent-butyl ether
NaHMDS: Sodium hexamethyldisilazane
Pyr.TFA: Pyridinium trifluoroacetate
TBME: Tert-butyl methyl ether
TFA: Trifluoro acetic acid
THF: Tetrahydrofuran
TsCl: Tosyl chloride Example 1

Preparation of ER-028695

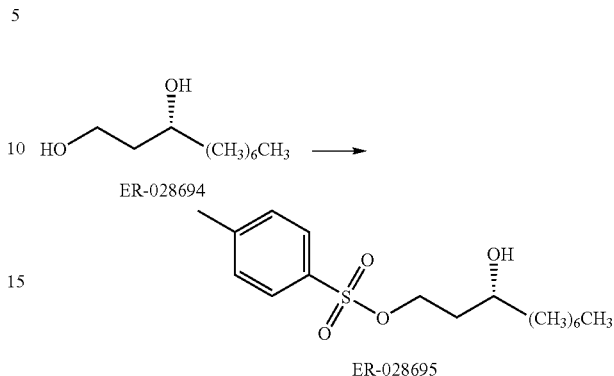

Preparation 1: To a stirred solution of p-toluenesulfonyl chloride (1704 g, 8.938 mol) in dry tetrahydrofuran (THF) (2408 g) in a dry 22-L reactor under a nitrogen atmosphere at 0° C. was added ER-028694 (952 g, 5.46 mol) in dry THF (1041 g) over a 9-minute period. The residual ER-028694 was rinsed with anhydrous THF (364 g) into the reactor. Triethylamine (1.35 Kg, 13.4 mol) was added drop wise to the clear yellow reaction solution over a 19-minute period during which time the solution turned cloudy. The residual triethylamine was rinsed with dry THF (30 g) into the reaction mixture.

After stirring for an additional 15 hours 17 minutes at 0° C., the reaction was quenched with a slow addition of 1.0 M of hydrochloric acid (2120 g) over a 36-minute period with a temperature change from 0.1 to 5.9° C. Brine (785 mL) was added over a 3-minute period, stirring continued for an additional 5 minutes followed by transferring the reaction mixture (~22 L) to a 50-L work-up reactor with THF (0.57 Kg). The organic layer was separated from the aqueous layer (pH=6). The organic layer was washed with a mixture of 1.0 M hydrochloric acid (2120 g) and brine (785 mL). The organic layer was then washed with a mixture of water (2120 mL) and brine (980 mL).

The organic layer was transferred to a clean 22-L reactor followed by the addition of THF (1.6 Kg) under a nitrogen atmosphere. The solution was cooled to 0° C. (ice-water bath) with stirring followed by the addition of 10% aqueous NaOH solution (2.04 Kg) over a 7-minute period with a temperature change from −0.4 to 2.3° C. After the addition of 28% aqueous $NH_4OH$ solution (935 g) over a 6-minute period with a temperature change from 1.9 to 12.5° C., the mixture was stirred for 25 minutes followed by the addition of heptane (1.1 Kg). The reaction mixture was transferred to a 50-L work-up reactor with heptane (0.532 Kg), mixed well, allowed to settle, and the aqueous layer (pH 14) was discarded. The organic layer was washed with 10% aqueous NaOH (2.04 Kg) followed by water (2.04 Kg). Evaporation of the organic layer solvent (house vacuum) and azeotroping the residue with heptane (1.1 Kg) provided a clear, orange oil. The isolated material (1.839 Kg) was used in the next step without further purification. Analytical Data for ER-028695: $^1$H-NMR ($CDCl_3$, 400 MHz) δ0.88 (t, J=7.1 Hz, 3H), 1.2-1.5 (m, 12H), 1.57 (bs, 1H), 1.6-1.7 (m, 1H), 1.8-1.9 (m, 1H), 2.45 (s, 3H), 3.7-3.8 (m, 1H), 4.1-4.2 (m, 1H), 4.2-4.3 (m, 1H), 7.35, (d, J=7.8 Hz, 2H), 7.80 (d, J=7.8 Hz, 2H). MS-APESI (M+Na)

Calcd for $C_{17}H_{28}NaO_4S$: 351.16 Found: 351.23. HPLC: ER-028695:ER-817864 ratio of 87.11%:11.71%.

Preparation 2: Anhydrous THF (250 mL) was added to a stirred solution of p-toluenesulfonyl chloride (161.1 g, 0.845 mol) under a nitrogen atmosphere. ER-028694 (90.0 g, 0.516 mol) was then added followed by triethylamine (176 mL, 1.26 mol) at a reactor temperature of 22° C. to give clear yellow solution. The solution turned cloudy after a few minutes. After stirring for 15 h 33 min, a 100-µL sample was taken. GC analysis showed 100% conversion. Another 100-µL sample was taken, and extracted with 2.0 mL process water and 3.0 mL heptane. The organic layer was washed with process water (2.0 mL) twice, and then with brine (2.0 mL). The resulting organic layer was evaporated under reduced pressure to give a colorless oil. $^1$H-NMR analysis of the colorless oil showed an ER-028694/ER-028695/ER-817864 ratio of 1.00/91.93/7.07.

After the reaction was determined to be complete, 1.0 M of hydrochloric acid solution was added with a temperature change from 21.4° C. to 26.8° C., followed by an addition of brine (74.2 mL). The organic layer (~0.6 L) was separated from the aqueous layer (~0.4 L, pH=10) and washed with a mixture of 1.0 M hydrochloric acid (201 mL) and brine (74.2 mL) followed by a mixture of process water (201 mL) and brine (92.7 mL). The organic layer was then transfer to a clean reactor followed by the addition of THF (200 mL) under a nitrogen atmosphere. The solution was cooled to 10° C. with stirring followed by the addition of 10% aqueous NaOH solution (193 g) over 2 min while keeping the reaction temperature below 25° C. (temperature changed from 15.3° C. to 21.3° C.). An aqueous $NH_4OH$ solution (88.4 g) was then added over a 5-min period (delayed exotherm was observed) while still keeping the reaction temperature below 25° C. (temperature changed from 15.5° C. to 22.7° C.). The reaction mixture was warmed to 20° C. under stirring for 15 min. The reaction mixture was extracted from the aqueous layer with heptane (200 mL), with the aqueous layer having a pH of 14. The organic layer was washed with 10% aqueous NaOH (193 g) followed with process water (193 mL). Evaporating the solvent (at 29-32° C., 20 ton) and chasing the residue with heptane (200 mL, 29-32° C., 4.4 torr) produced a clear, orange oil. The isolated material was used in the next step (assuming 100% yield) and without further purification. $^1$H-NMR analysis of the colorless oil gave an ER-028694/ER-028695/ER-817864 ratio of 0.9/90.9/8.2. KF was 13.0 ppm.

Example 2

Preparation of ER-806158

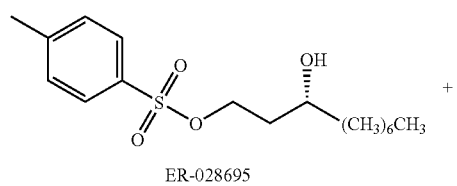

ER-028695

+

-continued

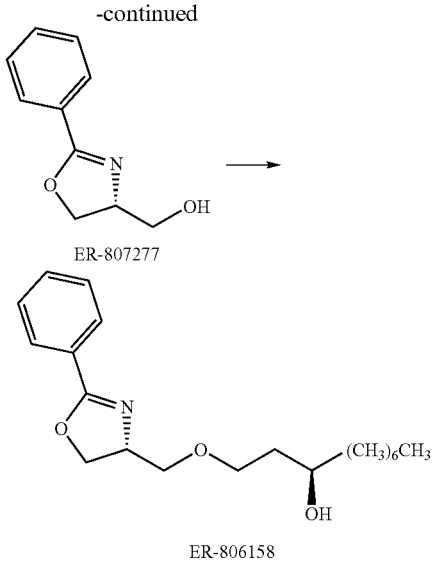

Preparation 1: To a stirred solution of ER-807277 (1.177 Kg, 6.642 mol) in dry THF (10.580 Kg) in a dry 22-L reactor under a nitrogen atmosphere at −1° C. was added 1.0 M sodium bis(trimethyldisilyl)amide in THF (3.300 Kg) over a 33-minute period while keeping the reaction temperature between −0.8-4.1° C. After stirring the solution for an additional 17 minutes at −0.1° C., crude ER-028695 (1.089 Kg, 3.316 mol) in dry THF (0.968 Kg) was added to the reaction solution over a 5-minute period maintaining the temperature between −0.1-3.9° C. The residual ER-028695 was rinsed into the reactor with dry THF (0.253 Kg). The final reaction mixture was warmed to room temperature during which time the orange clear reaction solution turned into a suspension (approx. at 19° C.). After stirring for 3 hours 31 minutes at room temperature, the completed reaction mixture was cooled to 0.1° C. and poured into a mixture of cold saturated aqueous $NH_4Cl$ (4.7 Kg) and brine (1.65 L) in a 50-L work-up reactor (exothermic, Tmax=16.2° C.). Water (2×1.0 L) followed by toluene (3.769 Kg) was used to rinse the residual reaction mixture to the work-up reactor. After stirring the mixture for 5 minutes, the reaction mixture was allowed to settle for 5 minutes and the resultant bottom aqueous layer (pH=9) was discarded. The solvent of the organic layer was partially evaporated under house vacuum at 30-34° C. The container was rinsed with minimum THF (0.4 Kg) and the rinse was combined with the product. Toluene (0.4 Kg) was added with heating (bath temperature=30-34° C.) to break up the solid into a slurry for ease of transfer.

The crude slurry was transferred to a clean, dry 22-L reactor under nitrogen followed by heptane (7.503 Kg) with fast stirring at ~19° C. After additional stirring for 6 hours 22 minutes, the mixture was subjected to vacuum filtration (Fisher P5 filter paper, catalog #09-801G), and the cake (~5.4 L) washed with heptane three times: 0.99 Kg, 1.02 Kg and 1.01 Kg, respectively. The combined filtrate and washes were evaporated at 30-34° C. under house vacuum to give a cloudy orange oil (1.207 Kg). The white solid cake in the filter funnel is ER-807277.

The crude product (1.206 Kg) was dissolved in methyl tert-butyl ether (MTBE)/heptane=1/4 (700 mL), filtered through a medium fritted filter funnel followed by rinsing the filter cake with MTBE/heptane=1/4 (300 mL) to give a clear yellow filtrate. The crude ER-806158 solution was loaded onto a pre-conditioned silica gel cartridge [Biotage 150 L (5.62 Kg, void volume=7.07 L) cartridge conditioned with MTBE (10.46 Kg) followed by MTBE/heptane=1/4 (3.140 Kg/11.606 Kg)] using an adjusted the flow rate to ~840 mL/min (~25 psi solvent pressure). After loading, the cartridge was rinsed with MTBE/heptane=1/4 (0.148 Kg/0.547 Kg) followed by elution with MTBE/heptane=1/4 (2.09 Kg/7.740 Kg), with MTBE/heptane=2/3 (2.094 Kg/2.904 Kg, with MTBE/heptane=7/3 (3.661 Kg/1.448 Kg), and finally with MTBE (40.298 Kg). Approximately 350-mL fractions were collected during the entire chromatography process. The combined, product containing fractions were concentrated and azeotroped to dry using heptane (0.540 Kg) followed by drying under house vacuum at 33° C. for 1 hour 13 minutes to give a clear orange oil (0.793 Kg, 71%) at 98.32 area % purity.

Crystallization of ER-806158

2.376 Kg of purified ER-806158 was dissolved in heptane (8.121 Kg) and transferred to a clean dry 22-L reactor under a nitrogen atmosphere followed by stirring. The clear yellow solution was cooled to −15° C. stepwise at ~4° C. every 0.5 h. The resulting white suspension was stirred for an additional 1 hour at −15° C. followed by filtration over a chilled filter funnel and filter paper using vacuum with a nitrogen blanket over the filter cake. The desired solid was washed with cold heptane (−12.3° C., 1.387 Kg) filtered as above and the filter cake was kept under vacuum for 14 hours 13 minutes (T=14.9-18.8° C.) while applying a nitrogen blanket on top of the solid. The mother liquor, washes, and the solvent to dissolve residual ER-806158 in the reactor were combined for recycles.

Obtained: 2.068 Kg, 87.0% yield

Analytical Data for ER-806158

Purity: 99.84 wt/wt %
Chiral purity: 99.72% e.e.
KF: 0.21%
Heptane: 268 ppm
$^1$H-NMR (CDCl$_3$) 0.88 (t, J=6.9 Hz, 3H), 1.2-1.6 (m, 12H), 1.6-1.7 (m, 1H), 1.7-1.8 (m, 1H), 3.21 (bs, 1H), 3.6-3.7 (m, 3H), 3.7-3.8 (m, 2H), 3.5-3.6 (m, 2H), 4.2-4.3 (m, 1H), 4.5 (m, 2H), 7.42, (t, J=7.6 Hz, 2H), 7.49, (dd, J=6.9, 7.8 Hz, 1H), 7.95 (d, J=7.3 Hz, 2H).

Elemental Analysis (EA): Calcd for $C_{30}H_{59}NO_6$: C, 72.04; H, 9.37; N; 4.20 Found: C, 71.83; H, 9.30; N, 4.08.

m.p. (DSC) Onset, 26.7° C.; Maximum, 29.5° C.

XRD and X-ray structure (Only one solid form is identified).

Preparation 2: The quantity (mol) of ER-028695 used in the reaction was calculated based on the amount of starting ER-028694 used in Example 1, procedure 2, assuming 100% yield. ER-807277 (178.3 g, 1006 mmol) was added to a clean dry 5-L reactor under a nitrogen atmosphere. Dry THF (1.8 L) was added with stirring to produce a clear, yellow solution, and the solution was cooled to 0° C. NaHMDS/THF (1.0 M, 553 mL) was added over a 20 minute-period and the reaction temperature was kept at less than or equal to 5° C. (3.8-1.3° C.). The solution was stirred for 10 minutes and then cooled to −5° C. Crude ER-028694 (calculated to be 165 g, 503 mmol) was transferred with dry THF (165 mL, 1 vol.) to a dry clean flask under a nitrogen atmosphere with stirring, which produced a clear, orange solution. The ER-028695/THF solution was then added to the reaction solution over a 6-minute period, with the temperature changing from −3.2° C. to 0.4° C. Residual ER-028695 was rinsed into the reactor with dry THF (40 mL) and the reaction mixture was warmed to room temperature in a warm water bath (23° C.). During the warm-up process, the clear, orange reaction solution turned into a suspension. After 1.75 h of stirring at 18.7-21.3° C., a sample (10 μL) was taken, added to 1.0 mL MeCN, and filtered through 0.2 μm syringe filter to give a colorless clear filtrate. HPLC analysis (TM-779) detected 98.2% conversion. After 3 h total stirring at room temperature, HPLC analysis showed 99.5% conversion. Saturated aqueous NH$_4$Cl (0.66 L) was added in one portion (exothermic, 18.9-26.0° C.), followed by additions of process water (0.30 L), brine (0.25 L), and toluene (0.66 L). Stirring was continued for 5 minutes after the additions. The solvent of the top organic layer (~2.6 L) was partially evaporated under reduced pressure at 29-32° C. to give a slurry (481.7 g), and the bottom aqueous layer (~1.4 L, pH=11) was discarded.

The slurry was transferred to a dry clean 5-L reactor under nitrogen. Heptane (1.65 L) was added at room temperature with fast stirring that continued for 14 h. The mixture was subjected to vacuum filtration (medium filter paper), the resulting cake (~0.52 L) was washed with heptane (0.33 L), and the yellow filtrate (~2.8 L) was collected. Solvent evaporation (29-32° C.) under reduced pressure produced an orange oil (177.9 g).

The crude product (177.9 g) was dissolved in TBME/heptane=1/4 (178 mL) and loaded onto a Biotage 75L silica gel (834 g, void volume=1.05 L) cartridge conditioned with TBME (2.1 L) followed by TBME/heptane=1/4 (3.15 L) using an adjusted flow rate of ~170 mL/min (~18 psi solvent pressure). Fractions 1-2 (~350 mL each fraction were collected. After loading, the cartridge was rinsed with TBME/heptane=1/4 (178 mL) and eluted with TBME/heptane=1/4 (2.1 L), collecting fractions 2-8; eluted with TBME/heptane=2/3 (1.05 L), collecting fractions 8-11; eluted with TBME/heptane=7/3 (1.05 L), collecting fractions 11-14; and eluted with TBME (8.4 L), collecting fractions 15-39. The collected fractions were analyzed (TLC, silica gel F254; mobile phase, TBME; visualization, UV and anisaldehyde solution), and the product containing fractions (14-35) without ER-807277 contamination were combined. Solvent evaporation (29-32° C., 80 torr) chased with heptane (29-32° C., 10.3 torr) produced a clear, orange oil (114.4 g), which solidified upon cooling to room temperature. HPLC analysis (TM-779) detected 96 area %.

The orange solid (114.4 g, 1 wt) was warmed (29-32° C.) and transferred with heptane (572 mL) to a 1-L dry clean reactor under a nitrogen atmosphere with stirring. The solution was cooled 14° C., stirred for 0.5 h, and seeded with ER-806158 crystals (0.112 g). Stiffing was continued for 0.5 h, at which time solid particles were visible. The reaction mixture was cooled stepwise to −10° C. (4° C. every 0.5 h), further cooled to −15° C., while stirring continued for 1 h. A chilled a medium filter funnel was prepared with cold (~−20° C.) heptane (~200 mL), and the reaction mixture was filtered through the funnel by vacuum, followed by a wash with cold heptane (~−20--15° C.). The vacuum was continued for 1.5 h and a nitrogen blanket was applied on top of the cake. The resulting white coarse, granular solid was then transferred to a bottle (98.4 g, 0.295 mol). Analytical results showed: wt/wt %, 99.95; purity, 99.68; residual heptane, 19.1 ppm; KF, 1.04%. DSC showed melt on-set was 27° C. Chiral HPLC analysis (TM-573) detected 99.8 area %.

Example 3

Preparation of ER-819059

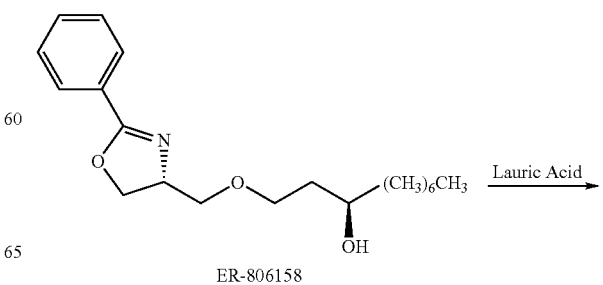

ER-806158

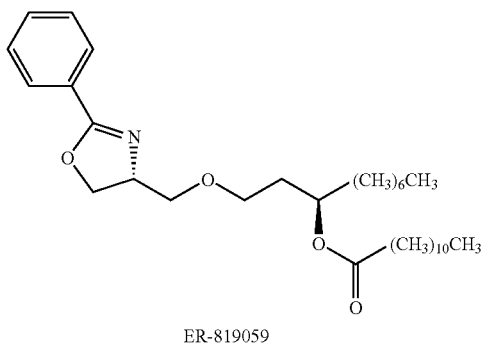

ER-819059

Preparation 1: To a stirred solution of N-(3-dimethylaminopropyl)-N'-ethylcarbodiimide hydrochloride (904 g, 4.176 mol), lauric acid (purified, 881 g, 4.398 mol), and ER-806158 (1400 g, 4.198 mol) in dry dichloromethane ($CH_2Cl_2$) (3710 g) in a clean dry 22-L flask under a nitrogen atmosphere was added 4-dimethylaminopyridine (51 g, 0.417 mol). After stirring for 1 hour 13 minutes, the reaction mixture turned into a slightly cloudy yellow solution and the reaction temperature reached a maximum of 26.7° C. After 6 h 34 minutes the reaction was found to be 98.9% complete time at which time additional N-(3-dimethylaminopropyl)-N'-ethylcarbodiimide hydrochloride (303 g, 1.581 mol) was added in one portion. After stirring for a total of 20 hours 50 minutes at room temperature, MeOH (5566 g) was added in one portion to the yellow reaction suspension (slightly endothermic, $T_{min}$=17.1° C.). Partial solvent evaporation (house vacuum, 29-32° C.) to remove the $CH_2Cl_2$ (3.71 Kg) was followed by extraction with equal portions of heptane (2×2.86 kg ea.) The heptane extracts were evaporated (house vacuum, 30-35° C.) and azeotroped to dry using heptane (0.75 Kg).

The product (2.192 Kg) was dissolved in heptane (3.00 Kg) and loaded onto a silica gel cartridge [Biotage 150L silica gel (5.62 Kg) pre-conditioned with MTBE/heptane=1/1 (15.0 Kg)]. The product was eluted at an adjusted flow rate of ~0.84 L/min (solvent pressure=22 psi) with MTBE/heptane=1/1 (31.3 Kg.) collecting approx. 350 mL eluant/fraction. The product containing fractions were combined and concentrated to dryness and vacuum dried (16° C., house vacuum, 16 hours 13 minutes) to give ER-819059 (2.102 Kg, 86.4% yield) as a clear, pale yellow oil.

Analytical Data for ER-819059
HPLC analysis: 99.76 area %.
KF: 0.36%
Heptane: 725 ppm
$^1$H-NMR ($CDCl_3$) 0.881 (t, J=7.1 Hz, 3H), 0.884 (t, J=6.9 Hz, 3H), 1.2-1.3 (m, 26H), 1.5-1.6 (m, 2H), 1.6-1.7 (m, 2H), 1.8-1.9 (m, 2H), 2.28 (t, J=7.6 Hz, 2H), 3.4-3.6 (m, 3H), 3.69 (dd, J=3.7, 9.6 Hz, 1H), 4.3-4.6 (m, 3H), 5.0 (m, 1H), 7.43, (t, J=7.6 Hz, 2H), 7.51, (dd, J=6.0, 7.3 Hz, 1H), 7.95 (d, J=6.0 Hz, 2H).
MS-APESI (M+H) Calcd for $C_{32}H_{54}NO_4$: 516.41 Found: 516.48
TLC: (silica gel F254): MTBE/heptane=1/1; $R_f$ of ER-819059=0.51

Preparation 2: N-(3-Dimethylaminopropyl)-N'-ethylcarbodiimide hydrochloride (1.49 g, 7.77 mmol), ER-806158 (2.00 g, 6.00 mmol), DMAP (0.07 g, 0.59 mmol) and dodecanoic acid (1.44 g, 7.19 mmol) were added to a dry 50-mL flask under a nitrogen atmosphere. Dry dichloromethane (6.0 mL) was then added with stirring. The stirring was continued at room temperature until a slightly cloudy solution resulted. After stirring for 16 h, a sample (10 μL) was taken and added to 1.5 mL MeCN. HPLC analysis (TM-780) detected 95.1% conversion. An additional amount of N-(3-dimethylaminopropyl)-N'-ethylcarbodiimide hydrochloride (0.307 g, 1.60 mmol) was then added. After another 8 h of stirring (24 h total), a second sample (10 μL) was taken, and analyzed as before. HPLC analysis (TM-780) detected 99.6% conversion. The stirring was continued for another 15 h (39 h total), at which time a third sample was taken and analyzed. HPLC (TM-780) analysis detected 99.96% conversion. Saturated aqueous $NaHCO_3$ (10 mL), brine (10 mL), and heptane (10 mL) were then added while stirring continued for 0.5 h. A poor emulsion was observed. Heptane (10 mL) was then added, and mixed well, but did not substantially improve the emulsion. Next, MeOH (3.0 mL) was added, and mixed well, but it also did not substantially improve the emulsion. The composition was allowed to settle for 0.5 h, and the milky aqueous layer that formed on the bottom was drained. The aqueous layer was extracted with TBME (20 mL), and the bottom aqueous layer was drained after it was allowed to settle for about 15 min. TLC analysis (TLC, silica gel F254; mobile phase, TBME; visualization, UV and anisaldehyde solution) of the aqueous layer detected a significant amount of product. The aqueous layer was again extracted with TBME (20 mL) and the organic layers were combined. Solvent evaporation (29-32° C., 7.5 torr) produced a clear, yellow oil (3.35 g).

The crude product (3.35 g) was dissolved in TBME/heptane=1/1 (12 mL) and loaded onto Biotage 12M silica gel (8.99 g, void volume=11.3 mL) cartridge conditioned with TBME/heptane=1/1 (36 mL). The product was eluted at an adjusted flow rate of ~12 mL/min, collecting 15 fractions (~6 mL each). The collected fractions were analyzed (TLC, silica gel F254; mobile phase, TBME/heptane=1/1; visualization, UV and anisaldehyde solution), and fractions containing product (3-15) were combined. Solvent evaporation (29-32° C., 8.3 torr) produced a clear, colorless oil (3.03 g). HPLC analysis (TM-780) detected 99.18 area %. The aqueous workup was not performed because of the poor emulsion.

Example 4

Preparation of ER-819120

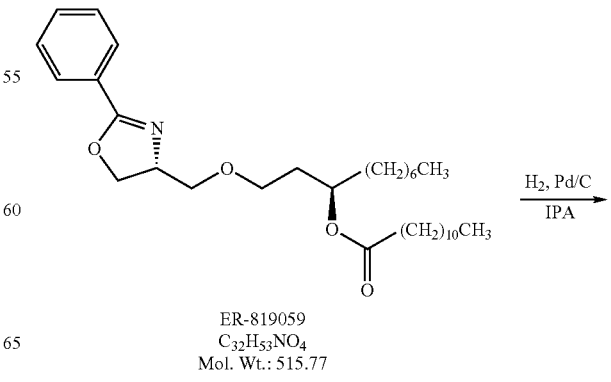

ER-819059
$C_{32}H_{53}NO_4$
Mol. Wt.: 515.77

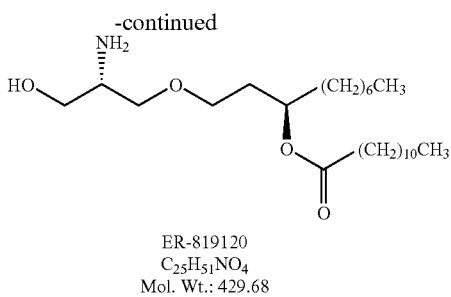

ER-819059 (3.03 g, 5.87 mmol, 1 wt) and 10% Pd/C (0.303 g, 0.28 mmol) were added to a clean 50-mL flask with IPA (20.2 mL, 6.67 vol.) under a nitrogen atmosphere. The flask was evacuated with fast stirring at room temperature and purged with hydrogen (hydrogen pressure maintained at 0.04 bar). This evacuation-and-purging process was repeated two additional times. The reaction was monitored through HPLC analysis of various samples After the reaction was complete, about 3.5 days, the flask was evacuated and purged with nitrogen three times. The resulting mixture was filtered through 0.2-μm syringe filter and rinsed with IPA (2×4.0 mL). The colorless clear filtrate was then combined and the crude product/IPA solution was used for the next reaction (assuming 100% yield without purification).

Example 5

Preparation of ER-819302

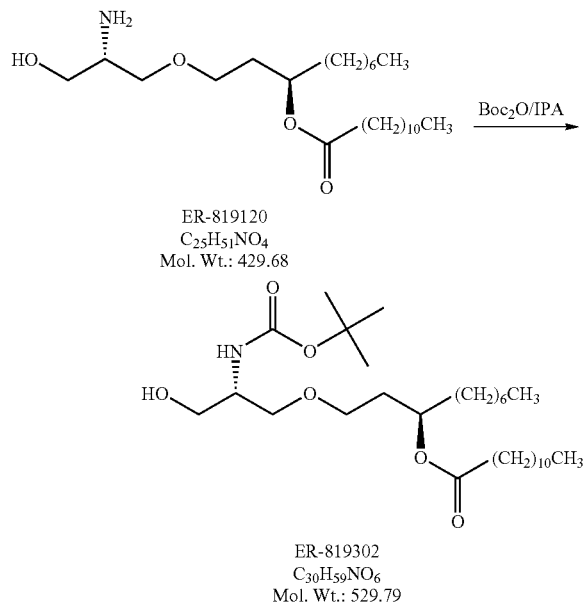

The quantity of ER-819120 (mol) was calculated based on the starting ER-819059 of the previous step.

To the 50-mL flask containing ER-819120 in IPA (2.52 g equivalent of ER-8189120, 5.87 mmol, ~31.5 mL) was added di-tert-butyldicarbonate (1.30 g, 5.96 mmol) in one portion under a nitrogen atmosphere with stirring. The reaction was monitored by HPLC (Sample preparation: Sample 15 μL, and add to 1.0 mL MeCN) and TLC (TLC, silica gel F254; mobile phase, MeOH/CH$_2$Cl$_2$/NH$_4$OH=10/89/1; visualization, anis- aldehyde solution or ninhydrin solution). TLC detected only minor ER-819120 spot. More di-tert-butyldicarbonate (0.20 g, 0.92 mmol) was added. No improvement was noticed by TLC analysis. Solvent evaporation (29-32° C., 10 torr) gave a colorless clear oil (3.21 g).

A Biotage 12M silica gel (8.99 g, void volume=11.3 mL) cartridge was conditioned with TBME/heptane=1/1 (36 mL, 3 v.v.). The flow rate was adjusted to ~12 mL/min. After dissolving the crude product (3.35 g) in TBME/heptane=1/1 (12 mL), it was loaded onto the cartridge, and eluted with TBME/heptane=1/1 (70 mL). Fifteen fractions (~6 mL each) were collected and analyzed (TLC, silica gel F254; mobile phase, TBME/heptane=1/1; visualization, UV and anisalde- hyde solution). Product from fractions (3-15) were combined. Solvent evaporation (29-32° C., 8.3 torr) gave a colorless clear oil (3.03 g).

Example 6

Alternative Preparation of ER-819302

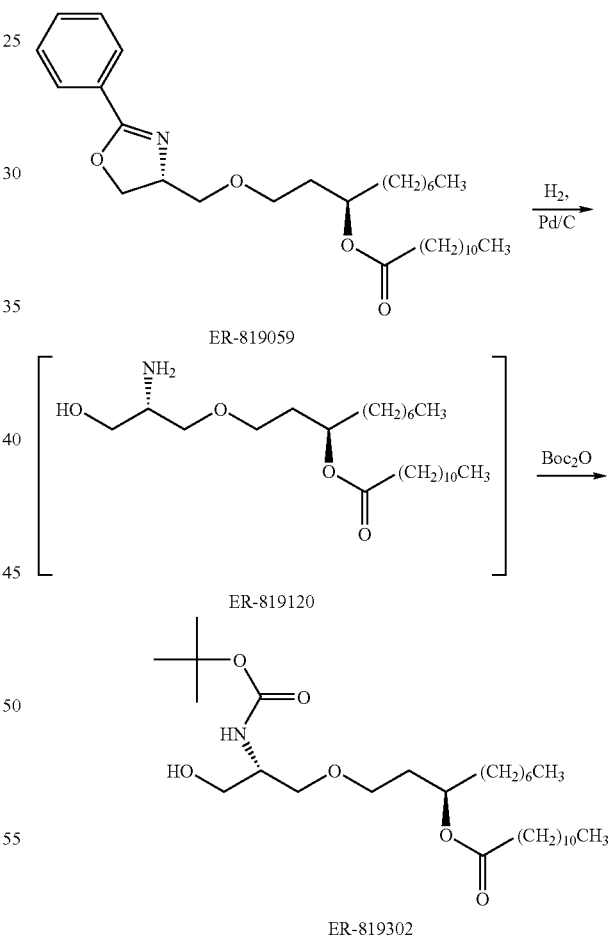

To ER-819059 (1.970 Kg, 3.82 mol) divided equally into two clean 12-L reactors with isopropanol (IPA) (4.647 Kg each) was added 10% Pd/C (99 g=flask 1, 102 g=flask 2). The flasks were evacuated (−0.79 bar) then purged with hydrogen (0.05 bar) three times while stirring. The reactions were main- tained under a hydrogen atmosphere (0.04 bar) of room tem- perature for 7 days and 16 hours after which time the reactions were evacuated (house vacuum) and purged with nitrogen three times to remove all traces of excess hydrogen followed by cooling to 0° C. under a nitrogen atmosphere.

In two separate flasks, di-tert-butyldicarbonate (434 g, 1.99 mol; and 438 g, 2.01 mol, respectively) was dissolved in anhydrous THF (203 g each) under nitrogen atmosphere. In to each of the flasks, was added cooled ER-819120 reaction mixtures over a 5-minute period. Anhydrous THF (40 g each) was used to rinse the residual reagents into the reaction mixture. The reactions were found to be exothermic (4.5 to 10.1° C.) and gassing was observed. The reactions were warmed to room temperature and continued to stir overnight. The completed reactions were combined and filtered over Celite 545 (1.143 Kg, packed on a Fisher P5 24 cm filter) and rinsed with IPA (3.091 Kg) under a nitrogen blanket, The residue in the reactors was rinsed and filtered with IPA (1.417 Kg) followed by rinsing the filter pad with IPA (13.46 Kg). The filter bed was rinsed two additional times with IPA (4.573 Kg and 6.360 Kg, respectively).

Concentration of the combined filtrates followed by azeotroping with heptane (7.529 Kg) gave a clear, colorless oil (2.452 Kg; 70.57 area % purity). The crude product was divided evenly into four portions purification.

The crude ER-819302 (611 g, 1 wt) was dissolved in heptane (613 g, 1 wt), and loaded onto a Biotage 150L silica gel cartridge [(5.620 Kg) conditioned with MTBE (10.48 Kg), and then with heptane (15.51 Kg) using a flow rate of 700 mL/min]. Heptane (340 g, 0.56 wt) was used to rinse the residual ER-819302 onto the column. The column was eluted with 15% MTBE/heptane (7.102 Kg/36.994 Kg), and then MTBE (15.72 Kg) where fractions of approximately 3 L/each were collected. The remaining crude ER-819302 was separately chromatographed in three equal portions using the same method. The combined desired fractions from four purifications were concentrated and azeotroped with heptane (0.5 Kg) to dryness, to provide ER-819302 as a clear colorless oil (1.9135 Kg; 94.6% yield in 97.86 area % purity).

Analytical Data for ER-819302-00

$^1$H-NMR (CDCl$_3$) □ 0.89 (t, J=6.9 Hz, 6H), 1.2-1.3 (m, 26H), 1.46 (s, 9H), 1.5-1.7 (m, 4H), 1.7-1.8 (m, 1H), 1.8-1.9 (m, 1H), 2.30 (t, J=7.6 Hz, 6H), 3.3-3.4 (m, 1H), 3.48 (td, J=6.9, 9.6 Hz, 1H), 3.5-3.6 (m, 2H), 3.69 (td, J=6.1, 7.1 Hz, 1H), 3.76 (d, J=8.2 Hz, 2H), 5.0-5.1 (m, 1H), 5.2 (bs, 1H).

MS-APESI (M+Na) Calcd for C$_{30}$H$_{59}$NNaO$_6$: 552.42 Found: 552.52

KF=0.30%

Heptane=6034 ppm; MTBE=not detected.

Example 7

Preparation of ER-819344

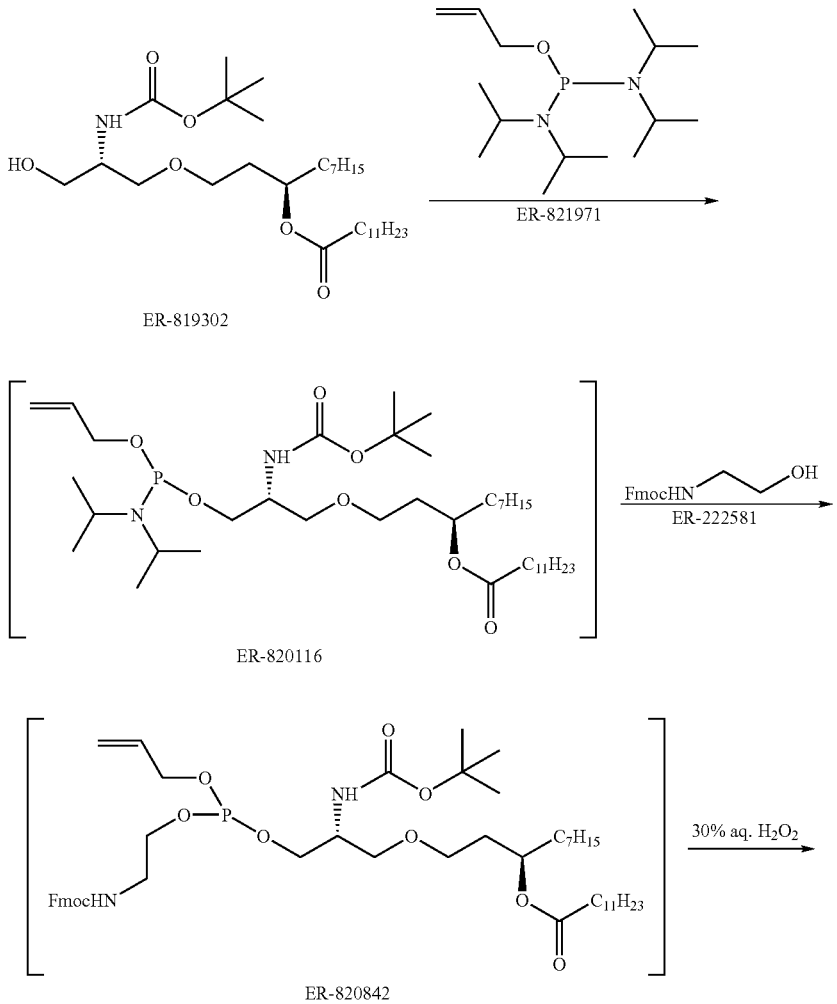

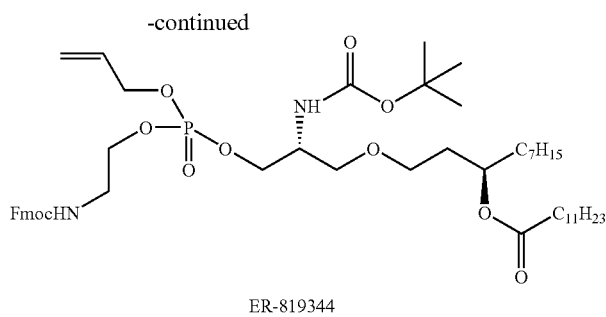

ER-819344

Preparation 1: To a stirred solution of diisopropylamine (22.4 mL, 0.160 mol) in anhydrous $CH_2Cl_2$ (200 mL) under a nitrogen atmosphere at room temperature was added pyridinium trifluoroacetate (30.9 g, 0.160 mol) in one portion providing a slight exotherm. Once the reaction mixture returned to room temperature allyl tetraisopropylphosphorodiamidite (51.1 mL, 0.160 mol) was added followed by stirring for 10 minutes. ER-819302 (84.4 g, 0.159 mol), was azeotroped to dryness several times using anhydrous $CH_2Cl_2$ (300 mL) until the water content was determined to be less than 60 ppm. After dissolving ER-819302 in dichloromethane (300 mL), the solution was slowly added to the above pyridinium reaction mixture maintaining the reaction temperature between 20 to 30° C. followed by rinsing the residue from the reagent vessel with additional dichloromethane (100 mL).

When the formation of the reaction intermediate ER-820116 was complete (2 hours), the reaction mixture was cooled to 0° C. and followed by a dropwise addition of acetic acid (18.2 mL, 0.320 mol) maintaining the reaction temperature between 0 to 15° C. Pyridinium trifluoroacetate (11 g, 0.056 mol) was added to the reaction mixture and the resulting reaction was stirred for 10 minutes immediately after which time ER-222581 (46.5 g, 0.164 mol) was added in one portion. The reaction mixture was stirred at room temperature for 2 hours, then the mixture was cooled 0° C. and 30-wt. % hydrogen peroxide in water (49 mL, 0.480 mol) was added dropwise maintaining the final reaction temperature between 0 to 10° C. (strong initial exothermic). The reaction mixture was warmed up to room temperature and stirred for an additional 30 minutes after which time the reaction mixture was cooled to 0° C. The final reaction mixture was quenched with a slow addition of 10 wt. % aqueous sodium bisulfite (3.5 L) at an addition rate maintaining reaction temperature between 0 to 10° C. The quenched reaction was allowed to warm to room temperature and stirred for until a negative peroxide test for both ensuing layers (30 minutes).

The resultant mixture was diluted with MTBE (2.0 L), stirred for 10 minutes and then transferred into a workup vessel. The layers were separated and the organic layer was washed one time each with 5% aqueous $NaHCO_3$ (2.0 L) and a 1:1 mixture of brine in water. The combined aqueous layers were back extracted with MTBE (1 L). The combined organic layers were dried over anhydrous sodium sulfate (100 g), filtered and concentrated, and azeotroped to dryness with MTBE to provide ER-819344 (146.6 g, 97% yield, 97% pure by HPLC).

Analytical Data for ER-819344

$^1$H-NMR ($CDCl_3$) 0.85-0.90 (m, 6H), 1.20-1.36 (m, 26H), 1.40-1.65 (m, 4H), 1.44 (s, 9H), 1.70-1.83 (m, 2H), 2.27 (t, J=7.6 Hz, 2H), 3.37-3.57 (m, 6H), 3.90-4.00 (m, 1H), 4.03-4.10 (m, 1H), 4.11-4.24 (m, 3H), 4.35-4.40 (m, 2H), 4.50-4.60 (m, 2H), 4.94-5.0 (m, 1H), 5.05-5.15 (m, 1H), 5.22-5.27 (m, 1H), 5.30-5.40 (m, 1H), 5.85-6.0 (m, 2H), 6.01-6.05 (m, 1H), 7.30 (dd, J=7.3, 7.8 Hz, 2H), 7.40 (dd, J=7.3, 7.8 Hz, 2H), 7.61 (d, J=7.8 Hz, 2H), 7.76 (d, J=7.3 Hz, 2H).

$^{31}$P-NMR ($CDCl_3$, not calibrated) 0.172, 0.564 (two diastereomers)

MS-APESI (M+Na) Calcd for $C_{50}H_{79}N_2NaO_{11}P$: 937.53 Found: 937.65.

Preparation 2:

ER-819302 (1 wt.) was dissolved in anhydrous dichloromethane (3 vol.). If the total amount of water is greater than or equal to 0.7 mol. % of ER-819302, as determined by $K_f$, then the water content is lowered to a satisfactory level by chasing the water with an evaporating solvent.

Anhydrous dichloromethane (2 vol.) was charged to a dry reactor, followed by diisopropyl amine and pyridinium trifluoroacetate (1 eq.) (in bath before added to control exotherm). The solution was stirred and the temperature adjusted in a bath to 20 to 25° C. Allyl tetraisopropylphosphorodiamidite (1 eq.) was then charged to the solution followed by stirring for five minutes. The dichloromethane solution of ER-819302 was then added to the solution at controlled addition rate while maintaining reaction temperature below 30° C. (rinse with 1 vol. dichloromethane). The reaction progress was monitored by TLC (MTBE/Heptane/Et3N=40/60/1) and HPLC (TM, samples were prepared by withdrawing a 30-ul reaction mixture and diluting it with 1 ml acetonitrile). The reaction is complete when the ER-819302:ER-820116 ratio is greater than 95:5, which usually occurs in 2 hours. After formation of the intermediate ER-820116, the reaction mixture was cooled to 0-10° C. and charged with acetic acid at an addition rate that maintains the reaction temperature below 15° C.

Pyridinium trifluoroacetate (0.4 eq.) was charged into reaction mixture, followed by ER-222581 (1 eq.). The mixture was stirred at room temperature for approximately 20-30 minutes until the white suspension became a clear solution. The reaction progress was monitored by TLC (MTBE/Heptane/Et3N=40/60/1) and HPLC (TM, samples were prepared by withdrawing a 30-ul reaction mixture and diluting it with 1 ml acetonitrile). After the reaction was complete, about 1.5 or 2 h, the reaction mixture was cooled to −5 to 0° C.

30 wt. % Hydrogen peroxide (3 eq.) in water was then charged into the reaction mixture while maintaining reaction temperature below 5° C. The reaction mixture was allowed to warm up to room temperature, and then stirred for 30 minutes. It was cooled back to −5 to 0° C., and 10 wt. % aqueous sodium bisulfite solution was charged while maintaining a reaction temperature below 5° C. After charging the bisulfite solution, the reaction mixture was again allowed to warm up to room temperature, and then stirred for 30 minutes. Stirring was continued until the reaction mixture indicated a negative result on a peroxide testing strip.

Methyl t-butyl ether was charged into the reaction and stirred for 10 minutes. The reaction mixture was then transferred into a workup vessel and the layers allowed to separate. If the aqueous layer was shown to contain product, it was back extracted with methyl t-butyl ether. The organic layers were washed with 5% aqueous sodium bicarbonate followed by a solution of half brine (if the aqueous layer is hazy, back extraction with methyl t-butyl ether may be necessary), and the organic was concentrated (if it became a milky oil, it was charged with MTBE and vacuum filtered). The crude ER-819344 was analyzed by HPLC and HNMR. The largest scale run produced 84.4 g ER-819302 with a 97% yield, as indicated by HPLC.

Example 8

Preparation of ER-819385-00

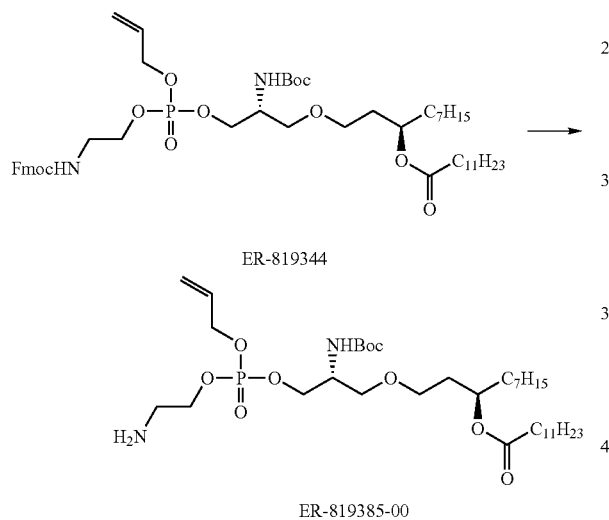

To a stirred solution of ER-819344 (1.56 g, 1.70 mmol) in THF (1.5 mL) at room temperature was added 2.0 M dimethylamine in THF (8.5 mL, 17.0 mmol) and the reaction mixture was stirred for 2 h. The completed reaction mixture was concentrated and the crude product was azeotroped to dryness two times with MTBE (15 mL). The resultant product was dissolved in MTBE (30 mL), and washed with brine (7.5 mL). The final organic layer was concentrated down to dryness, azeotroped with one time with MTBE (15 mL) to provide the desired, somewhat unstable ER-819385 that was used in the next step without further purification.

Preparation 2: ER-819344-00 (1.56 g, 1.70 mmol) was dissolved in THF (1.5 mL), and added to a commercial solution of dimethylamine in THF (2.0 M, 8.5 mL) at room temperature and stirred for 2 h. A TLC analysis was conducted which showed complete consumption of ER-819344. U.V. lamp and p-anisaldehyde stain were used as visualization techniques. The volatiles were then removed through rotary evaporation techniques. The crude product was azeotroped with MTBE (2×15 mL), after which it was dissolved in MTBE (30 mL) and washed with brine (7.5 mL to remove any residual low MW amines (for example, dimethylamine, ethanolamine). No emulsions were obtained, as the layers separated easily. The pH of the aqueous layer after this wash was ~10. The organic layer was concentrated down to dryness and azeotroped with MTBE (1×15 mL) to provide desired amine monomer ER-819385-00.

Example 9

Preparation of ER-819409-00

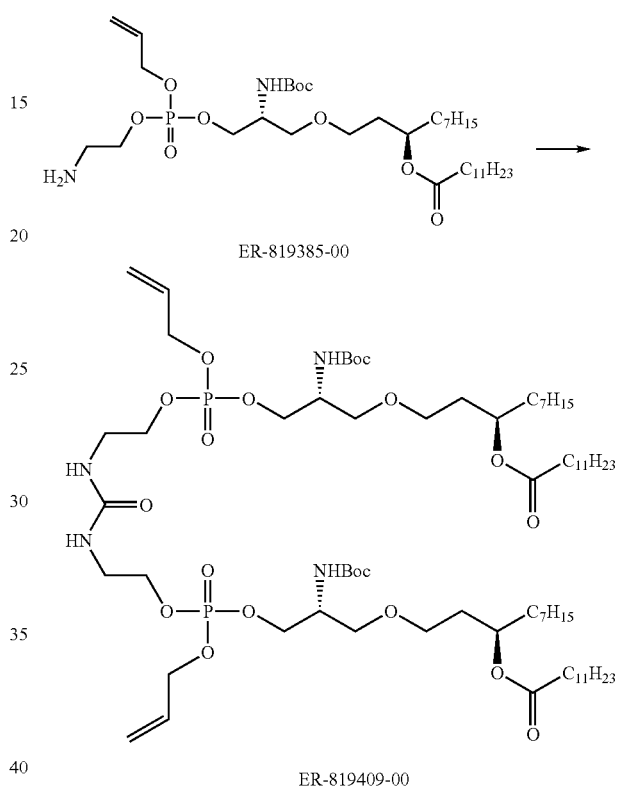

Preparation 1: To a stirred solution of crude ER-819385 (calc. 1.18 g, 1.70 mmol) in CH$_2$Cl$_2$ (15 mL) was added a saturated solution of NaHCO$_3$ (12 mL). The resulting mixture was cooled to 0° C. followed by a dropwise addition of 20% phosgene in toluene (465 μL, 0.935 mmol). The reaction was allowed to warm up to room temperature, stirred for 1 hour, then was cooled to 0° C. before the addition of a second portion of 20% phosgene solution (210 μL, 0.425 mmol). The final reaction mixture was warmed to room temperature, stirred overnight. Water (15 mL) was added. After stirring for an additional 30 minutes the quenched reaction was transferred into a separatory funnel and the layers allowed to separate for 45 min. The aqueous layer was extracted with CH$_2$Cl$_2$ (30 mL) and the combined organic layers were concentrated to dryness. The crude oil was azeotroped to dryness with MTBE/ethyl acetate (EtOAc) (1:1, 50 mL) dissolved in EtOAc/heptane (1:1, 50 mL) and filtered on a fritted funnel to remove salts. The crude product was purified over silica gel (12 g) eluted with 2.5% MeOH/Ethyl acetate (50 mL), with 3.8% MeOH/Ethyl acetate (50 mL), and finally with 5.6% MeOH/Ethyl acetate (100 mL) to provide ER-819409 (984 mg, 82% yield) as a clear, colorless oil.

Preparation 2: ER-819385-00 (1.70 mmol, crude material) was dissolved in CH$_2$Cl$_2$ (15 mL) and added to a saturated solution of NaHCO$_3$ (12 mL). The resulting mixture was cooled to 0 C and added dropwise to a commercial solution of phosgene in toluene (465 uL, 0.55 equiv.). The reaction was allowed to warm up to room temperature under stirring for 1 h. TLC (10% MeOH/CH$_2$Cl$_2$) and p-anisaldehyde analyses were used to visualize reaction products and revealed that a large amount of starting material was still present. The reaction was therefore cooled to 0° C. for a second addition of a 20% phosgene solution (210 uL, 0.25 equiv.). After the addition, the temperature of the reaction was allowed to slowly warm up to room temperature. TLC analysis 1 h later still showed starting material but indicated no signs of decomposition. The reaction was then allowed to sit overnight while being stirred. TLC analysis the next day still indicated presence of starting material, but also revealed the occurrence of base-line decomposition. Water was added (15 mL) to the reaction product at room temperature and stirred for 30 min. The mixture was transferred to a separatory funnel and the layers were allowed to stand for 45 min before they were separated. The aqueous phase was extracted with CH$_2$Cl$_2$ (30 mL) and the organic layers were combined and concentrated to dryness. TLC analyses of the aqueous and the combined organic layers did not indicate the presence of amine starting material, indicating that the reaction went to completion during the work up.

The crude oil was azeotroped with MTBE/EA, re-dissolved in ~50 ml EA/heptane at a 1:1 ratio, and filtered on a fritted funnel to remove salts. This material was purified on a SiO$_2$ column (50% EA/n-heptane, 100% EA, then 5-10% MeOH/EA) to provide 984 mg of the desired urea ER-819409-00, present as a colorless oil. This represents an 82% combined yield since the Fmoc deprotection. The mass balance was base-line material that formed during the overnight stirring of the urea-formation stage.

Example 10

Dihydroxy Urea Synthesis of ER-819409-00

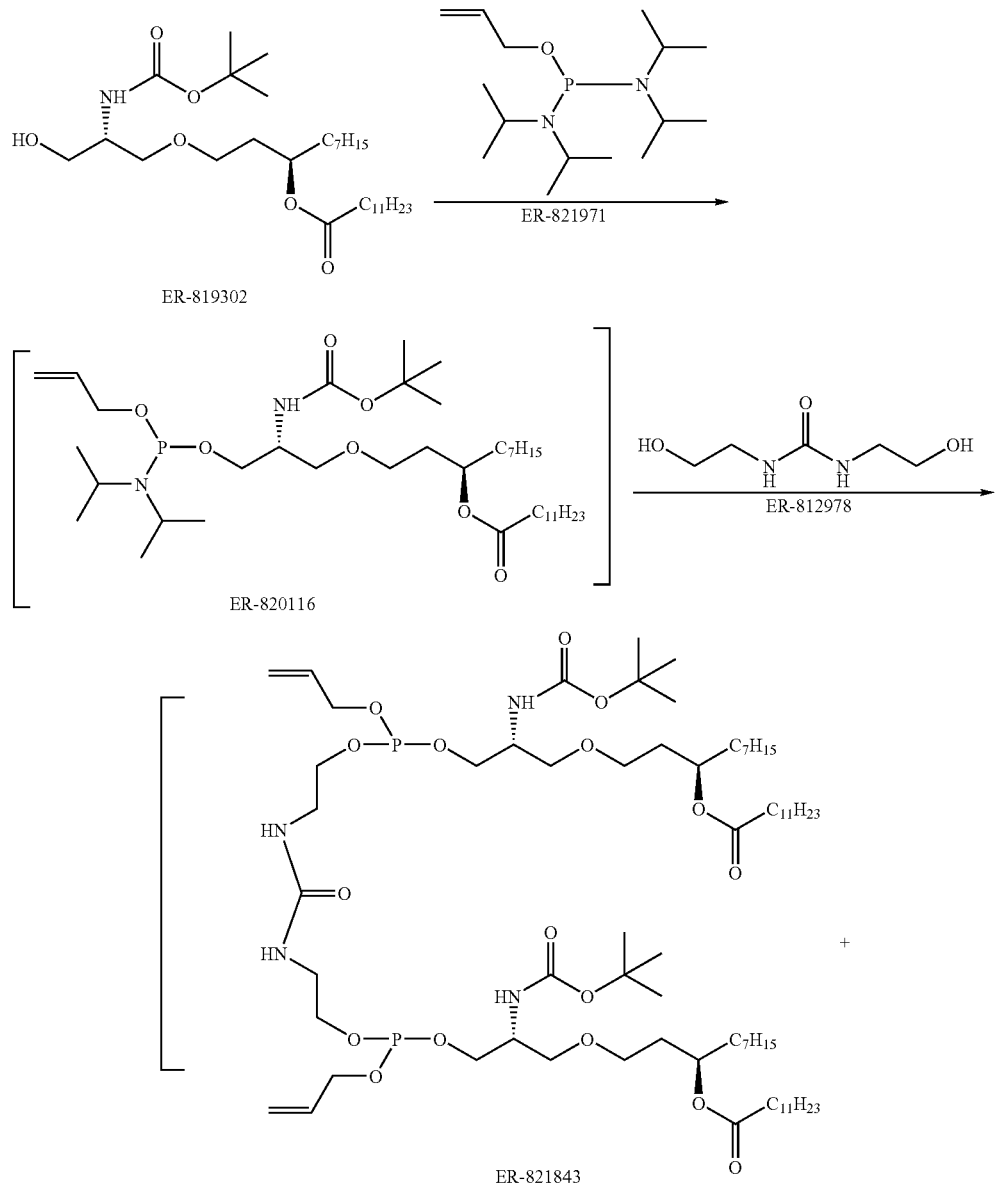

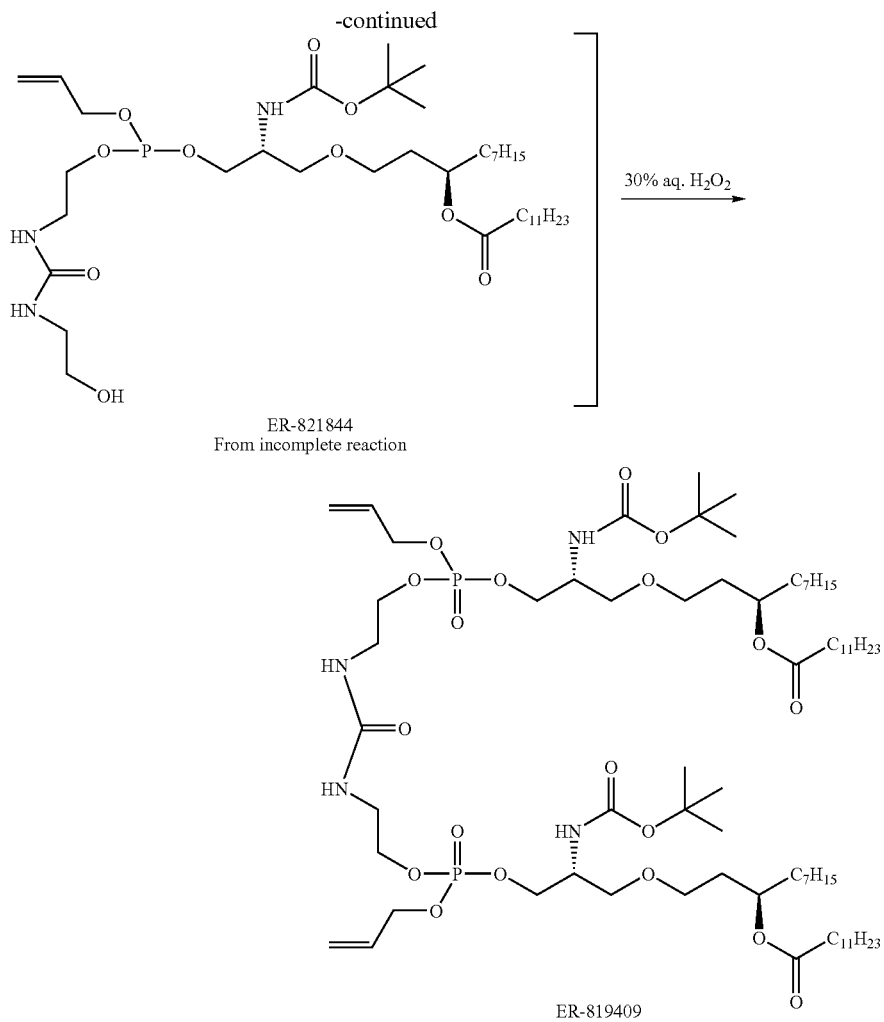

ER-821844
From incomplete reaction

ER-819409

To a stirred solution of pyridinium trifluoroacetate (108 g, 0.533 mol) in anhydrous acetonitrile (348 g) was added diisopropylamine (78.7 mL, 0.561 mol) at a rate to maintain the reaction temperature below 30° C. After allowing the reaction to cool to room temperature, allyl tetraisopropylphosphorodiamidite (179 mL, 0.561 mol) was added (slight endotherm then exotherm was observed) followed by stirring for an additional 10 minutes. Subsequently ER-819302 (283.2 g, 0.5345 mol; pre-chased with 800 mL of Heptane) in anhydrous acetonitrile (453 mL) was added at an addition rate to maintain reaction temperature between 20 and 30° C. After stirring for an additional 30 minutes the reaction mixture was cooled to 0° C. followed by the slow addition of acetic acid (64 mL, 1.1 mol) while maintaining reaction temperature below 25° C. The reaction mixture was allowed to equilibrate at room temperature. Pyridinium trifluoroacetate (103 g, 0.533 mol) in acetonitrile (200 mL) was added to the reaction mixture. Immediately after the addition of pyridinium trifluoroacetate was added ER-812978 (40 g, 0.27 mol) followed by an acetonitrile rinse (50 mL). The reaction mixture was stirred for 18 h at room temperature after which time it was cooled to 0° C. followed by the slow addition of 30 wt. % hydrogen peroxide in water (140 mL, 1.37 mol) maintaining reaction temperature between 0 to 24° C. (initially a strong exotherm). The final reaction mixture was stirred for an additional 30 minutes followed by addition of 20-wt % aqueous sodium bisulfite solution (3000 g) at a rate maintaining reaction temperature between 0 and 18° C. The reaction mixture was warmed up to room temperature and stirred until peroxide testing provided a negative result.

The resultant reaction mixture was diluted with MTBE (3000 mL) in a workup vessel and stirred for 15 minutes. After separation of the layers, the organic layer was washed with 10% aqueous sodium bicarbonate (NaHCO$_3$) (3500 mL) and then with 30% aqueous NaCl solution (2000 mL). The brine layer was back-extracted with MTBE (3000 mL) three times. The combined organic layers were concentrated, and chased with TBME/Heptane=1/1 (1.4 L) twice. The residue was dissolved in MTBE (735 g), and the suspension filtered through a Celite pad (150 g) followed by subsequent three MTBE (300 mL) washings of the vessel and filter pad. The filtrate was concentrated to dryness to give 363.4 g of slightly cloudy oil. The crude ER-819302 was dissolved loaded onto a pre-conditioned silica gel cartridge [Biotage 150L (5.62 Kg, void volume=7.07 L) cartridge conditioned with MTBE/Heptane=7/3 (15 Kg)] with TBME/Heptane=7/3 (400 mL) using an adjusted flow rate of ~800 mL/min. After loading, TBME/Heptane=7/3 (500 mL) was used to rinse residual ER-819302 and the rinse loaded onto the cartridge. The cartridge was eluted with MTBE/Heptane=7/3 (26 Kg), and then with MTBE/Heptane/MeOH=70/25/5 (21.8 Kg/7.18 Kg/1.7 Kg).

A total of 36 fractions were collected during this process. The combined, product containing fractions were concentrated and azeotroped to dry using heptane (8 L) followed by drying under house vacuum to give an oil (281 g, 79%) at 92.69 area % purity.

Analytical Data for ER-820116

$^1$H-NMR (CDCl$_3$) δ 0.870 (m, 6H), 1.176 (d, J=8.0 Hz, 12H), 1.254-1.282 (b, 28H), 1.428 (b, 9H), 1.528 (b, 2H), 1.603 (b, 2H), 1.790 (m, 2H), 2.265 (t, J=7.0 Hz, 2H), 3.431 (m, 2H), 3.481 (m, 2H), 3.600 (m, 2H), 3.751 (b, 2H), 3.847 (b, 1H), 3.847-4.208 (m, 2H), 4.950 (b, 1H), 5.126 (d, J=10 Hz, 1H), 5.286 (dd, J=17 Hz, J'=1.5 Hz, 1H), 5.898-5.989 (m, 1H)

$^{31}$P-NMR (CDCl$_3$, calibrated) 148.449 and 148.347 (two diastereomers)

MS-APESI (M+H) Calcd for C$_{39}$H$_{78}$N$_2$O$_7$P: 717.55. Found: 717.66.

Analytical Data for ER-821843

$^{31}$P-NMR (CDCl$_3$, calibrated) □ 139.832, 139.868, 140.170, 140.327 (4 diastereomers)

MS-APESI (M+Na) Calcd for C$_{30}$H$_{59}$NNaO$_6$: 552.42 Found: No Mass data

Analytical Data for ER-819409

MeOH: not detected

MTBE: not detected

MeCN: 185 ppm

Heptane: 1718 ppm $^1$H-NMR (CDCl$_3$) δ0.88 (t, J=6.9 Hz, 12H), 1.20-1.37 (m, 52H), 1.44 (s, 18H), 1.45-1.72 (m, 8H), 1.76-1.85 (m, 4H), 2.28 (t, J=7.6 Hz, 4H), 3.38-3.58 (m, 12H), 3.85-3.97 (m, 2H), 3.98-4.20 (m, 8H), 4.53-4.58 (m, 4H), 4.95-5.0 (m, 2H), 5.18-5.28 (m, 2H), 5.26 (dd, J=1.4, 10.5 Hz, 2H), 5.37 (dd, J=0.9, 16.9 Hz, 2H), 5.62-5.85 (m, 2H), 5.87-5.99 (m, 2H).

MS-APESI (M+Na) Calcd for C$_{71}$H$_{136}$N$_4$NaO$_{19}$P$_2$: 1433.92 Found: 1433.98.

Example 11

Preparation of ER-807284-00

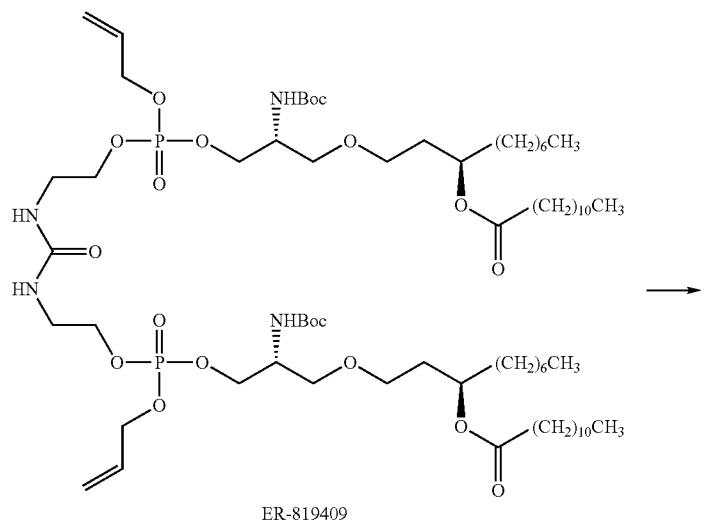

ER-819409

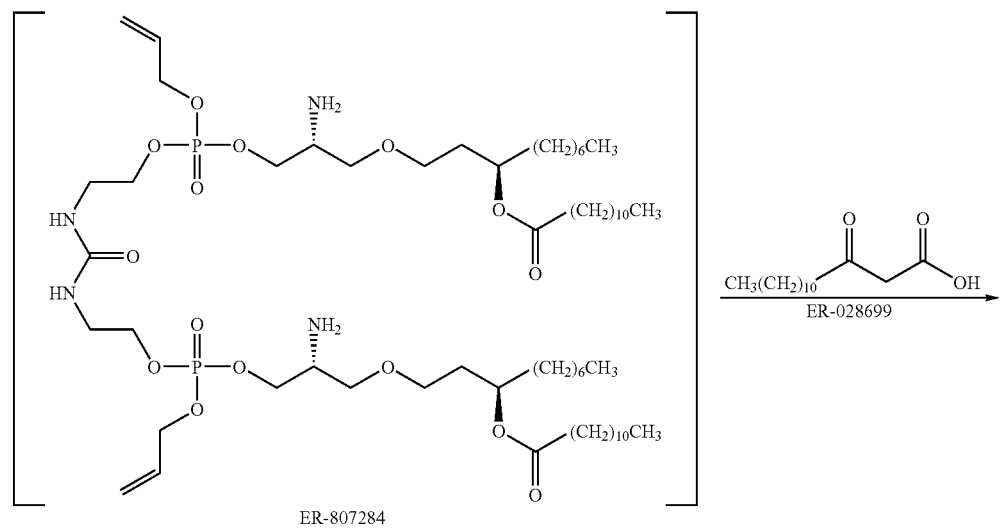

ER-807284

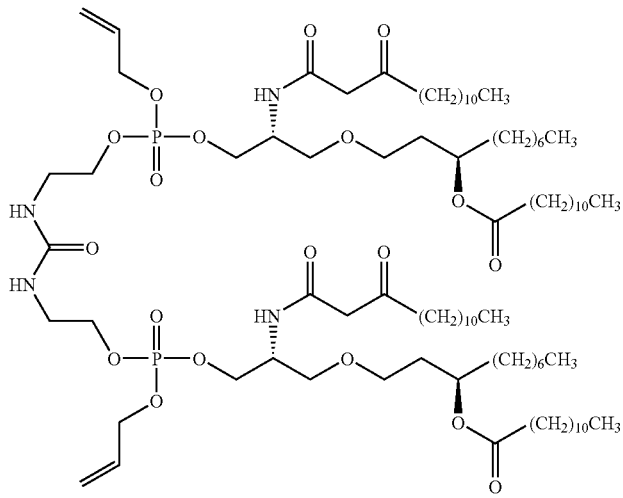

ER-807285

Preparation 1: To a stirred solution of ER-819409 (40.25 g, 28.51 mmol) in dry CH$_2$Cl$_2$ (120 mL) under a nitrogen atmosphere was added slowly over a 10-minute period a solution of methanesulfonic acid (13.8 g, 144 mmol) in CH$_2$Cl$_2$ (140 mL) while maintaining the reaction temperature below 20° C. The reaction mixture was warmed to 20° C. followed by stirring 15 hours when the intermediate reaction was determined to be complete. The resulting reaction mixture was cooled to 0° C. and diisopropylethylamine (27.5 mL, 158 mmol) was added over a 5-minute period. After 5 minutes of additional stirring at 0° C., 1-(3-dimethylaminoproply)-3-ehylcarbodiimide hydrochloride (32.55 g, 170 mmol) was added in one portion. The reaction mixture was stirred at 0° C. for 12 minutes followed by the addition of ER-028699 (20.6 g, 85.0 mmol) in one portion. The resulting reaction mixture was stirred for 2 hours at 0° C. followed by warming to room temperature for 30 minutes at which time the reaction was determined complete.

One fourth of the completed reaction mixture (105 g) was eluted onto a pre-condition Biotage 75M silica gel cartridge [(351 g silica gel, conditioned with MTBE (1 L) and then with CH$_2$Cl$_2$ (2 L)] with a flow rate adjusted to 150-200 mL/min. The column was eluted sequentially with 1% ethanol (EtOH)/CH$_2$Cl$_2$ (900 mL), with 3% EtOH/CH$_2$Cl$_2$ (900 mL) and finally with 6% EtOH/CH$_2$Cl$_2$ (2250 mL) while collecting ~150 mL/fractions. The desired product containing fractions were combined concentrated (house vacuum, 30-35° C.) and azeotroped three times with heptane (100 mL) to provide 8.8 g of ER-807285. The remainder of the completed reactions was purified in a similar manner to provide a total of 35.2 g (74.5% yield).

Two additional experimental procedures are described below. They differ at the work-up stage. The first one involves a standard quench and the other one uses a reverse quench. TLC analyses were performed with NH$_4$OH/MeOH/CH$_2$Cl$_2$ 1:9:90. TLC plates were charred with p-anisaldehyde stain to visualized starting material and reaction products.

Preparation 2: ER-819409-00 (995 mg, 0.705 mmol) was dissolved in CH$_2$Cl$_2$ (7.8 mL). TFA (1.4 mL) was added to this mixture at room temperature over 1-2 min. The reaction mixture was then stirred 4 h at room temperature.

After stirring, the reaction mixture was cooled with an ice bath and a saturated aqueous solution of NaHCO$_3$ (16.0 mL) was added over 25 min. The highest temperature recorded during the neutralization was ~8° C., with an average temperature of 4° C. The resulting mixture was stirred an additional 45 min during which time the internal temperature was allowed to slowly warm up from 4° C. to room temperature. The mixture was transferred to a separation funnel and CH$_2$Cl$_2$ was added (11.0 mL). The layers were allowed to stand for 35 min before being separated. The aqueous layer, which had a pH of 8-8.5, was extracted with CH$_2$Cl$_2$ (5.0 mL). The organic layers were combined and washed with 10 mL of a saline solution that was prepared by mixing a saturated brine solution with water in a 3:1 ratio. The layers were allowed to stand for 20 min before being separated. The organic layer was then stored in the freezer (−20° C.) overnight.

The next morning, the organic layer was removed from the freezer and allowed to warm up to room temperature. It was dried using Na$_2$SO$_4$, filtered on a fritted-funnel, and concentrated down to dryness. The resulting oil was re-dissolved in CH$_2$Cl$_2$ (8.0 mL) and filtered on a cotton plug in order to remove any salt residues. The resulting material was concentrated to dryness to produce the colorless oil ER-807284-00 (727 mg, 85% mass recovery). An additional CH$_2$Cl$_2$ extraction provided an extra 99.0 mg of desired material bringing the mass recovery to 96.8%. No purification was necessary.

Analytical Data for ER-807284

$^1$H-NMR (CDCl$_3$) δ0.85-0.95 (m, 12H), 1.20-1.35 (m, 52H), 1.45-1.65 (m, 8H), 1.70-1.85 (m, 4H), 2.25-2.65 (bs, 4H), 2.28 (t, J=7.6 Hz, 4H), 3.20-3.27 (m, 2H), 3.30-3.60 (m, 12H), 3.98-4.22 (m, 10H), 4.50-4.60 (m, 4H), 4.95-5.05 (m, 2H), 5.27 (dd, J=0.9, 10.5 Hz, 2H), 5.38 (dd, J=0.9, 16.9 Hz, 2H), 5.90-6.0 (m, 2H).

MS-APESI (M+H) Calcd for C$_{61}$H$_{121}$N$_4$O$_{15}$P$_2$: 1211.83 Found: 1211.97.

Preparation 3: An appropriate sized reactor was charged with containing containing CH$_2$Cl$_2$ (22.3 mL). ER-819409-00 (2.85 g, 2.01 mmol) was added and dissolved in the $CH_2Cl_2$. TFA (4.0 mL) was added over 1 min at r.t. The reaction mixture was stirred 4.5 h at room temperature.

Work-Up: (Reverse quench): The reaction mixture was transferred via a Teflon canula over 1-2 min to a saturated solution of $NaHCO_3$ cooled to 0° C. Slight warming was observed, max exotherm ~4° C. The reaction flask was rinsed with $CH_2Cl_2$ (4×2.5 mL) and the washings added to the solution. The cooling device was removed and the temperature was allowed to warm up to room temperature over 45 min. Additional $CH_2Cl_2$ (22 mL) was added and the mixture was transferred to a separatory funnel. The mixture was allowed to stand for 20 min before separation. The aqueous layer was extracted with $CH_2Cl_2$ (22 mL) and the organic layers combined. The combined organic layers were washed with a saline solution, saturated brine/$H_2O$ (3:1 ratio) (40 mL). The resulting mixture was allowed to stand for 30 min while the layers slowly separated. The layers were separated. The organic layer remained cloudy. The organic layer was stored in a −20° C. freezer overnight. It was then allowed to warm up to room temperature, dried with $Na_2SO_4$, filtered on a fritted funnel and concentrated to dryness. The aqueous brine solution was also back-extracted with $CH_2Cl_2$ (22 mL) to recover additional material. Proton and fluorine NMR spectra revealed that these two crops of material were contaminated by TFA salt forms. pH analysis of the $NaHCO_3$ layer revealed that its pH was ~7 (not sufficiently high (8-8.5) to cleanly give the free base ER-807284-00). The two crops obtained above were combined and the work up was repeated by dissolving the organic material in $CH_2Cl_2$ (50 mL). The combined solution was transferred to a 250 mL three-neck-round bottom flask equipped with a mechanical stirring device. A saturated aqueous solution of $NaHCO_3$ (50 mL) was added and the resulting mixture was stirred 45 min at room temperature. The content of the reactor was transferred to a 250 mL separatory funnel. The reactor was rinsed with $CH_2Cl_2$ (total 25 mL). The mixture was allowed to stand for ~1 h and emulsions were observed. The organic and aqueous layers were separated and the aqueous layer was back-extracted with $CH_2Cl_2$ (30 mL). The resulting organic layers were combined, washed with saturated brine (25 mL). Even after standing for 1 h, the organic layer remained cloudy after which time the organic and aqueous layers were separated. The organic layer was dried with $Na_2SO_4$, filtered on a fritted-funnel. The filtrate was cloudy. The brine solution was back-extracted with $CH_2Cl_2$ (25 mL). The material from the $CH_2Cl_2$ layer was combined with the other material after a similar drying procedure. The resulting combined organic filtrates were concentrated down to dryness, azeotroped with MTBE (2×25 mL), re-dissolved in $CH_2Cl_2$ (10 mL) and filtered on a Celite (3 mL) plug located in 10 mL syringe. The tip of that syringe was also equipped with a filtration device to catch small particles. The filtrate was concentrated to dryness and NMR spectroscopy revealed that the diamine ER-807284-00 was obtained and was free of TFA salts. The mass recovery was over 95%. The reaction was clean by TLC. The work up had to be repeated to cleanly generate the free-base and some degradation became apparent by TLC. pH control may improve this procedure.

Example 12

Preparation of ER-807285-00

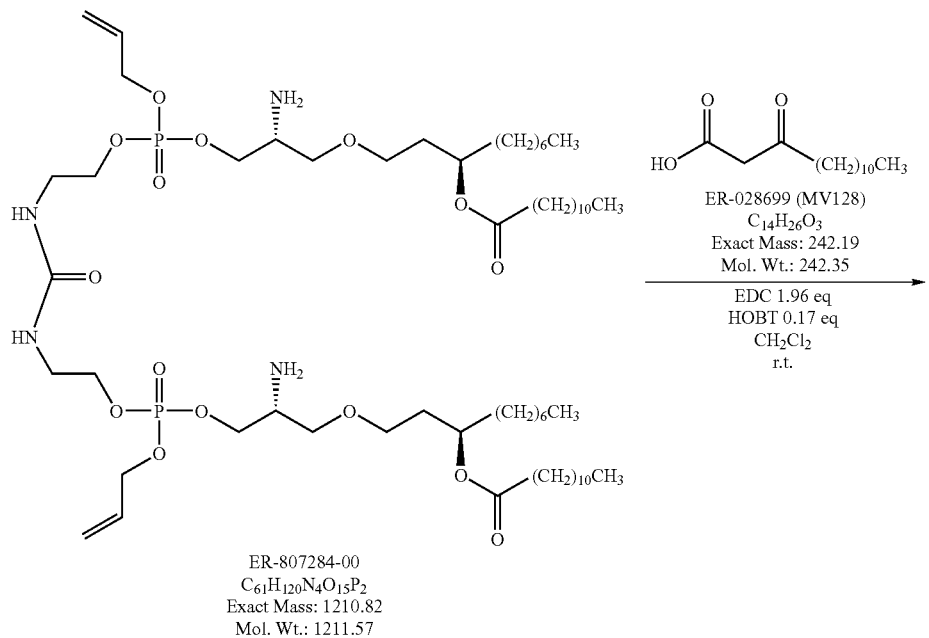

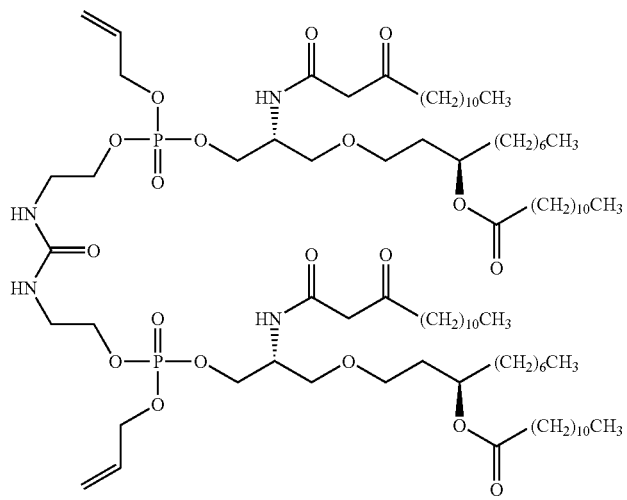

ER-807285-00
C89H168N4O19P2
Exact Mass: 1659.18
Mol. Wt.: 1660.25

Preparation 1—EDC/HOBT: An appropriately sized inert reactor was charged with ER-807284-00 (1.0 equivalent) and anhydrous methylene chloride (8.41 weights). The reactor was then charged with 1-[3-(dimethylamino)propyl]-3-ethyl-carbodiimide (2 equivalents) followed by 1-hydroxybenzotriazole (0.18 equivalent). The reactor was then charged with 3-oxo-tetradecanoic acid (2.2 equivalents) in three equal portions, letting the reaction mixture stir for 10 min between each charge keeping $T_{internal}$ at 15-20° C. The reaction was monitored by TLC for complete consumption of ER-807284. When the reaction was determined to be complete (typically after 1 h), process water (5 weights) was charged to the reactor. The mixture was allowed to stir for 20 minutes and then allowed to separate for 20 minutes. The organic layer was set aside. The aqueous layer was back extracted in the above manner with ethyl acetate two times (2×6 weights). All organic layers were then combined, charged with sodium sulfate (8 weights) and allowed to stand 15 min to absorb moisture. The organics were filtered and the cake was washed with ethyl acetate until a negative result for ER-807285 was obtained. The filtrates were concentrated in vacuo (~50 torr at 28-35° C.) affording ER-807285. That material was purified by silica gel chromatography using 3%-6% EtOH/CH$_2$Cl$_2$. Fractions rich in desired material were combined and concentrated down by rotoevaporation and dried with IVAC pump (0.2 torr) for 2 h. The yield was 50% of a colorless oil ER-807285.

Preparation 2—EDC/DMF: ER-807284-00 (208 mg, 0.172 mmol.) was dissolved in DMF (2.1 mL) in an appropriate sized reactor and EDC (263 mg, 1.37 mmol) added. The mixture was cooled to 0° C. and 3-oxotetradecanoic acid (166 mg, 0.686 mmole) dissolved in DMF (1.4 mL) was added dropwise over 30 sec. The resulting reaction mixture was stirred at 0° C. for 10 min while warming to room temperature. The reaction was monitored by TLC (7.5% MeOH/CH$_2$Cl$_2$: p-anisaldehyde stain for the starting materials and products. The reaction was quenched ~3 h later at 0° C. by the addition of a saturated solution of NaHCO$_3$ (8.0 mL), H$_2$O (4.0 mL) and MTBE/n-heptane 1:1 (10 mL). The reaction mixture was transferred to a separatory funnel. A small amount of MTBE/n-heptane 1:1 was used to rinse the reactor and then combined with the reaction mixture. The reaction mixture was allowed to for 20-30 min after which time the organic and aqueous layers were separated. The total volume of the organic layer was ~35 mL. Analysis of the aqueous layer by TLC showed a small amount of DMF. A second extraction of aqueous layer was not needed. The organic layer was washed with brine (4.0 mL) and then was allowed to stand 15 min. A fast separation was observed with no emulsions. The organic and aqueous layers were separated and the organic layer was evaporated to dryness to produce crude ER-807285-00. The crude ER-807285 was purified on a SiO$_2$ column using a: 3-6% EtOH/CH$_2$Cl$_2$ solvent system. The yield was 53%, (151 mg of ER807285), 88% pure by HPLC.

Preparation 3—HBTU/Hunig's base/DMF: ER-807284-00 (232 mg, 0.191 mmol,) was dissolved in DMF (2.5 mL). The reactor was cooled to 0 C. HBTU (218 mg, 0.574 mmol,) and 3-oxotetradecanoic acid (139 mg, 0.574 mmole) were added. This was followed by Hunig's base (106 uL, 0.612 mmol) dropwise over 30 sec. The reaction mixture was stirred 20 min at 0 C and became milky after ~10 min. The reaction mixture was allowed to warm up to room temperature. Stirring was continued over 4 h. TLC monitoring is difficult due to DMF. Accordingly the reaction time might be shorter. The reaction mixture was diluted with MTBE/n-heptane 1:1 (10 mL), transferred to a 60 mL separatory funnel, and treated with an aqueous solution prepared by mixing citric acid 1.0 M (50 uL) and saturated sodium chloride (9.5 mL) at pH 3). Significant amounts of salts were formed and crashed out, clogging the funnel. Water (5.0 mL) was added to dissolve the salts but after that, no phase separation was possible even after progressively adding MTBE (up to 15 mL). Ethyl acetate was then added taking up to 10 mL to start restoring phase separation. The layers were allowed to stand ~30 min to achieve separation. The pH of the aqueous phase was adjusted to pH 5. The organic layer was washed again with 10 mL of dilute citric acid prepared as described above, resulting in a pH of 3. The layers were separated. The organic layer was washed with a saturated solution of NaHCO$_3$ (2×5 mL). The resulting aqueous and organic layers were separated and the organic layer was evaporated to dryness. The yield of ER-807285 was 45% (143 mg) with 91% purity by HPLC.

Example 13

Preparation of E6020

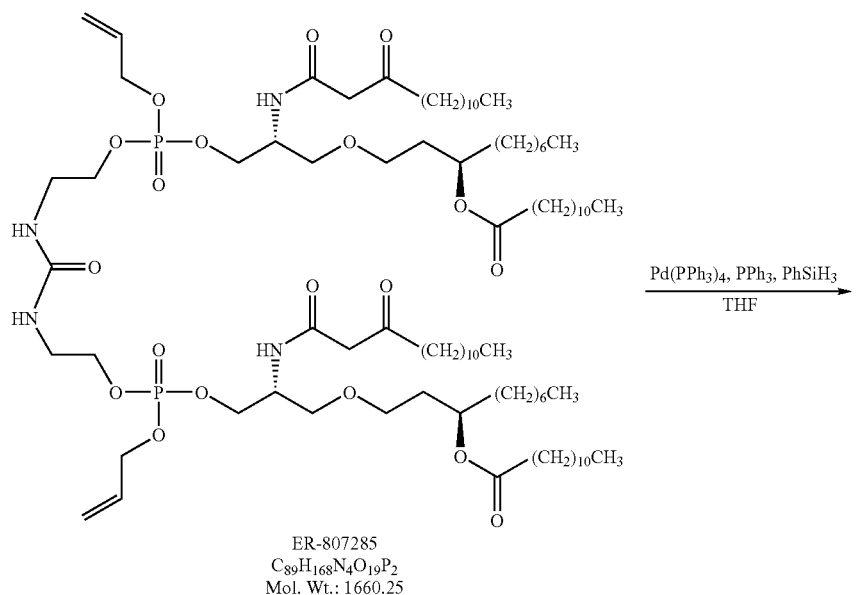

ER-807285
C$_{89}$H$_{168}$N$_4$O$_{19}$P$_2$
Mol. Wt.: 1660.25

Pd(PPh$_3$)$_4$, PPh$_3$, PhSiH$_3$
THF

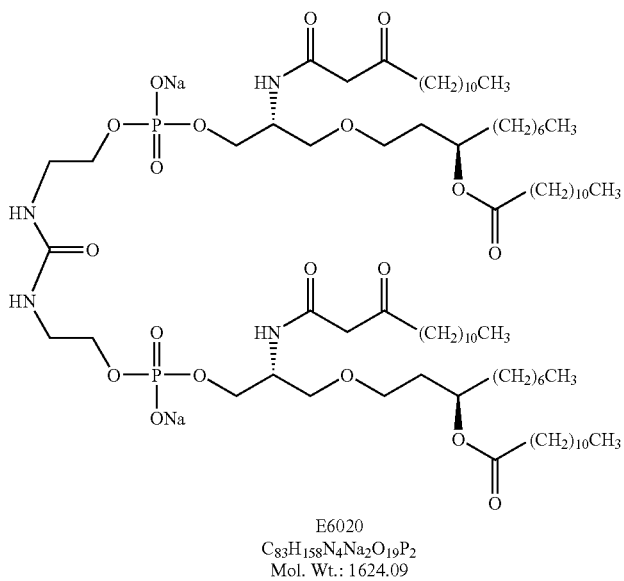

E6020
C$_{83}$H$_{158}$N$_4$Na$_2$O$_{19}$P$_2$
Mol. Wt.: 1624.09

An appropriately sized inerted vessel was charged with ER807285 (1 equivalent) in degassed THF (1.57 weight) under an argon stream. A solution of tetrakis(triphenylphosphine)palladium (0) (0.03 weight), triphenylphosphine (0.03 weight) and phenylsilane (0.07 weight) in tetrahydrofuran (2 weights) was charged in the reactor over 40 min (T$_{internal}$ typically raise to ~40-45° C.). The reaction was monitored by TLC and HPLC for complete consumption of ER-804057. When the reaction was determined to be complete (typically after <10 minutes), the reaction mix was purified by ion exchange chromatography. For more details about this purification, see example 14.

Example 14

Purification of E6020

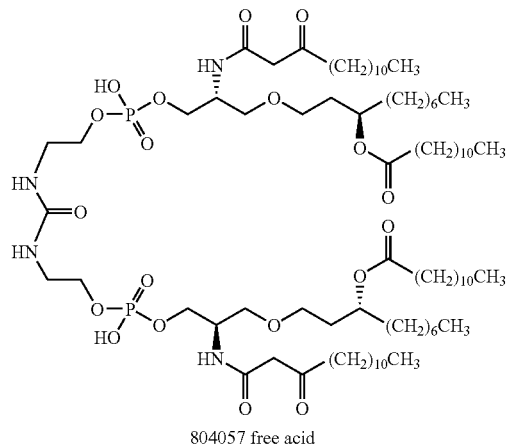

804057 free acid

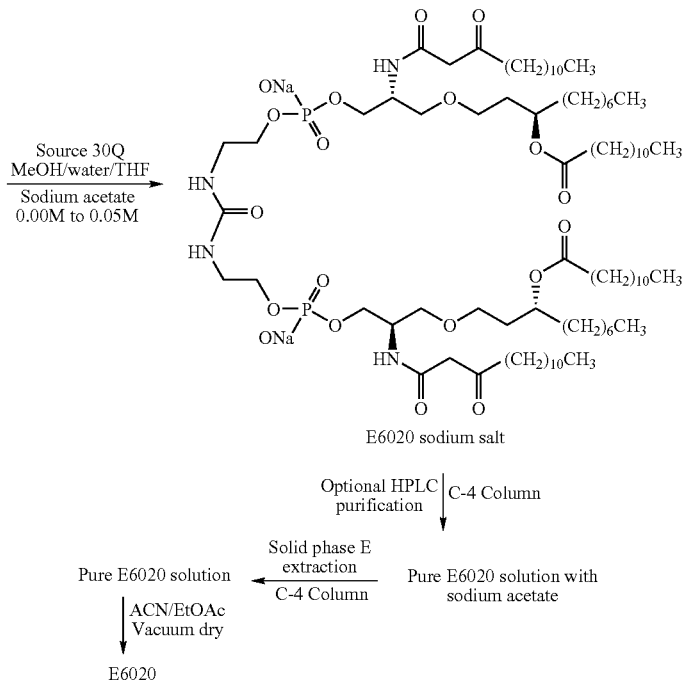

E6020 sodium salt

Source 30Q
MeOH/water/THF
Sodium acetate
0.00M to 0.05M

Optional HPLC purification | C-4 Column

Pure E6020 solution ← Solid phase E extraction C-4 Column ← Pure E6020 solution with sodium acetate ACN/EtOAc Vacuum dry

E6020

A crude reaction mixture of 804057 free acid containing tetrakis triphenylphosphine palladium (0), triphenylphosphine, and phenylsilane was loaded onto a Source 30Q ion-exchange column. Then, the non-binding reactants were eluted away from the 804057 using methanol/THF/water (77.5/15/5). The sodium salt of 804057 (i.e., E6020) eluted from the column by using an increasing linear gradient of sodium acetate that starts at 0 M and ends at 0.05 M. Impurities were removed during this chromatography.

An optional second purification may be desired This chromatography starts with the E6020/sodium acetate ion-exchange solution obtained from the previous chromatography. This was directly loaded onto a C-4 Kromasil column and eluted with the isocratic buffer system methanol/THF/water/sodium acetate (77.5/15/5/0.05 M). The fractions containing product were combined for solid phase extraction.

Pure E6020 solutions were then diluted 50/50 with water and loaded onto the C-4 Kromasil column. This was then eluted with water, a linear gradient from water to acetonitrile. This separated the salt and water from pure E6020. Then, the product was eluted from the column using methanol. A solution of pure E6020 in methanol was obtained. This was concentrated to dryness on a rotary evaporator at 25 to 30° C. and full house vacuum. The glassy product was lyophilized or treated with a solution of ethyl acetate/acetonitrile, which formed a white solid. This was vacuum dried to give E6020.

Example 15

Characterization of Crystalline ER-806158, (R)-1-(((R)-4,5-dihydro-2-phenyloxazol-4-yl)methoxy)decan-3-ol A portion of ER-806158 was re-dissolved in warm toluene until all the material dissolved, and was allowed to cool. This resulted in single crystals from which one was chosen to be used in this study. A colorless block crystal with dimensions 0.14×0.14×0.10 mm was mounted on a glass fiber using very small amount of paratone oil.

A. Single Crystal X-ray Diffraction

Data were collected using a Bruker SMART APEX CCD (charge coupled device) based diffractometer equipped with an Oxford Cryostream low-temperature apparatus operating at 193 K. Data were measured using omega scans of 0.3° per frame for 30 seconds, such that a hemisphere was collected. A total of 1271 frames were collected with a maximum resolution of 0.76 Å. The first 50 frames were recollected at the end of data collection to monitor for decay. Cell parameters were retrieved using SMART software (SMART V 5.625 (NT) *Software for the CCD Detector System*; Bruker Analytical X-ray Systems, Madison, Wis. (2001)) and refined using SAINT on all observed reflections. Data reduction was performed using the SAINT software (SAINT V 6.22 (NT) *Software for the CCD Detector System* Bruker Analytical X-ray Systems, Madison, Wis. (2001), which corrects for Lp and decay. The structures were solved by the direct method using the SHELXS-97 program (Sheldrick, G. M. SHELXS-90, *Program for the Solution of Crystal Structure*, University of Gottingen, Germany, 1990.) and refined by least squares method on $F^2$, SHELXL-97, (Sheldrick, G. M. SHELXL-97, *Program for the Refinement of Crystal Structure*, University of Gottingen, Germany, 1997.) incorporated in SHELXTL-PC V 6.10, (SHELXTL 6.1 (PC-Version), *Program library for Structure Solution and Molecular Graphics*; Bruker Analytical X-ray Systems, Madison, Wis. (2000)).

Figure 2:
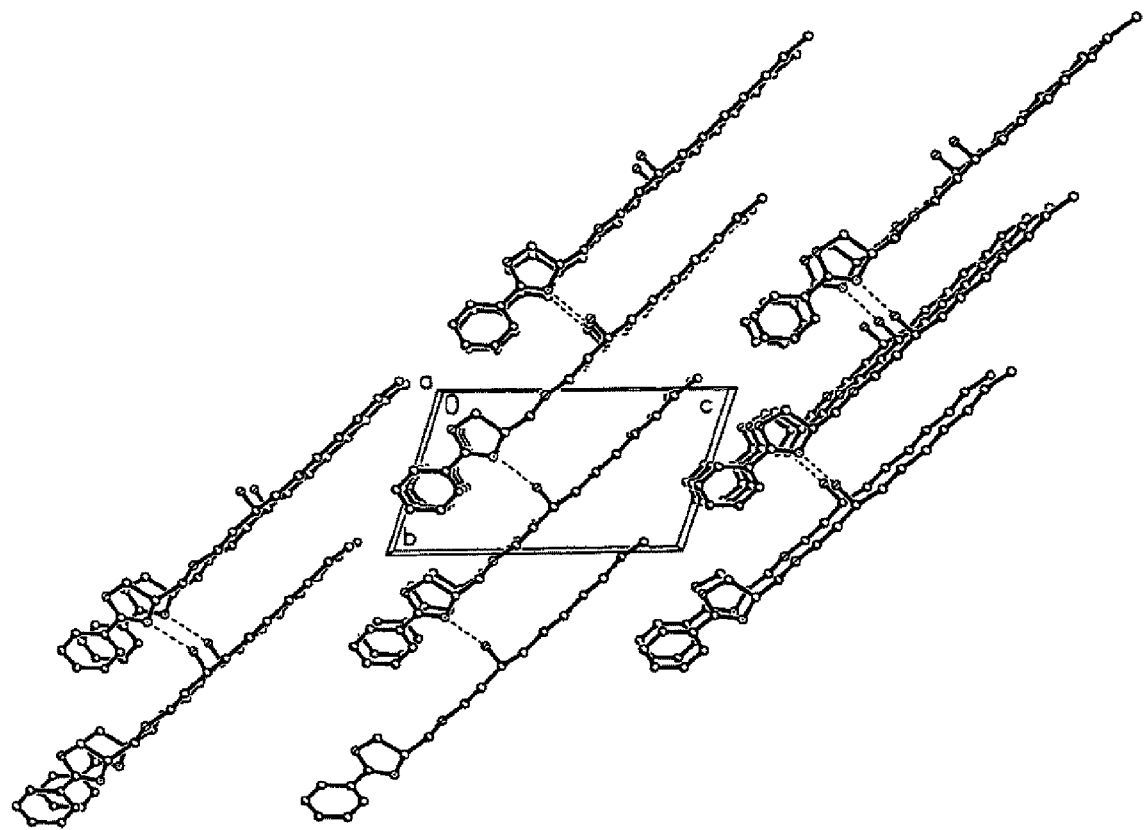
FIG. 2 is the packing diagram along the a-axis which shows the best diagram of the hydrogen bonding within the ER-806158 crystal, dotted lines.

The structure, shown in FIG. 1, was solved in the space group P1 (#1) by analysis of systematic absences. All non-hydrogen atoms are refined anisotropically. Hydrogens were found by difference Fouier methods and refined isotropically. The crystal used for the diffraction study showed no decomposition during data collection. All drawing are done at 50% ellipsoids. FIG. 2 is the packing diagram along the a-axis which shows the best diagram of the hydrogen bonding within the crystal, dotted lines.

TABLE 1

Crystal data and structure refinement.

| | |
|---|---|
| Wavelength | 0.71073 Å |
| Crystal system | Triclinic |
| Space group | P1 |
| Unit cell dimensions | a = 4.6047(11) Å  α = 106.008(4)°. |
| | b = 8.1161(19) Å  β = 95.604(4)°. |
| | c = 13.579(3) Å  γ = 98.696(4)°. |
| Volume | 477.0(2) Å$^3$ |
| Z | 1 |
| Density (calculated) | 1.161 Mg/m$^3$ |
| Absorption coefficient | 0.077 mm$^{-1}$ |
| F(000) | 182 |
| Crystal size | 0.14 × 0.14 × 0.10 mm$^3$ |
| Theta range for data collection | 1.58 to 27.93°. |
| Index ranges | −6 <= h <= 6, −10 <= k <= 7, −12 <= l <= 17 |
| Reflections collected | 3293 |
| Independent reflections | 2663 [R(int) = 0.0431] |
| Completeness to theta = 27.93° | 98.3% |
| Absorption correction | None |
| Max. and min. transmission | 0.9924 and 0.9893 |
| Refinement method | Full-matrix least-squares on F$^2$ |
| Data/restraints/parameters | 2663/3/342 |
| Goodness-of-fit on F$^2$ | 1.006 |
| Final R indices [I > 2sigma(I)] | R1 = 0.0474, wR2 = 0.1231 |
| R indices (all data) | R1 = 0.0527, wR2 = 0.1275 |
| Absolute structure parameter | 0.0(16) |
| Largest diff. peak and hole | 0.252 and −0.252 e · Å$^{-3}$ |

B. Powder X-ray Diffraction

Figure 3:
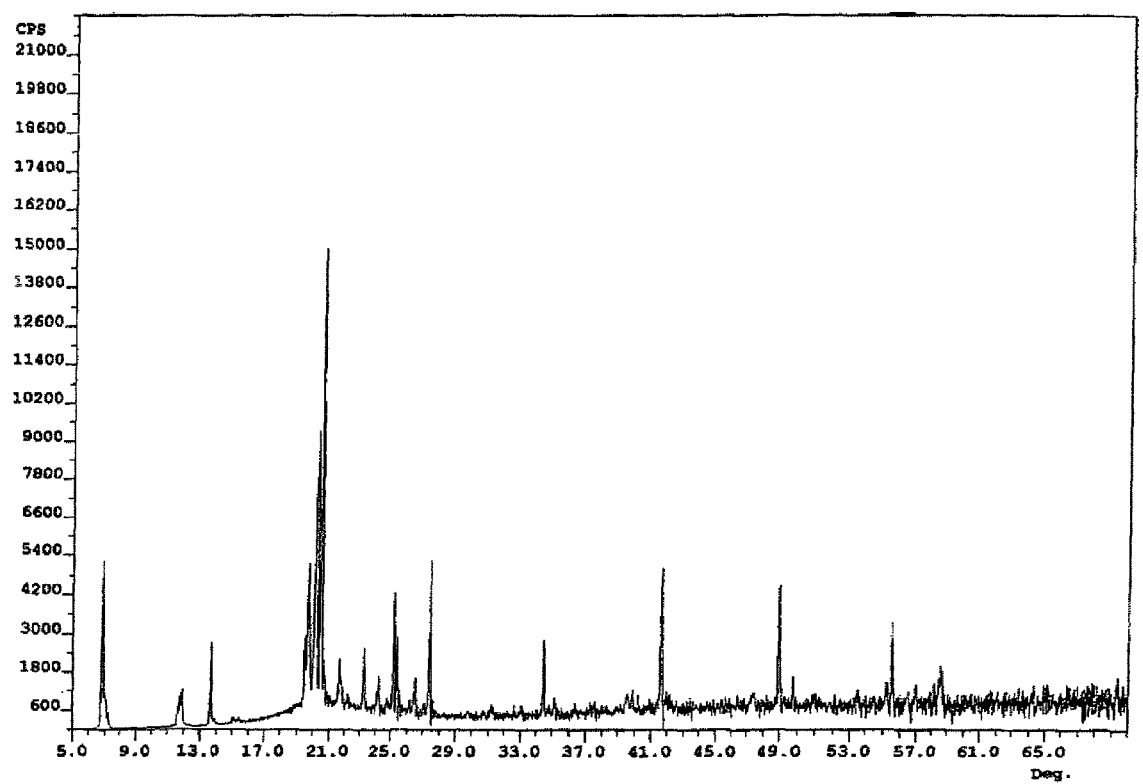
FIG. 3 depicts the Powder X-ray Diffraction (PXRD) pattern of crystalline ER-806158.

Using a quartz plate, on a Scintag Diffractometer, data was run under normal powder diffraction conditions, with 2-theta range of 5-70 degrees, using copper radiation and analyzed under the conditions shown in Table 2. No background correction was applied. FIG. 3 shows the PXRD pattern of crystalline ER-896158. Characteristic peaks for the PXRD pattern of crystalline ER-896158 are listed in Table 3.

TABLE 2

Measurement conditions

X-ray diffi-actometer: Scintag
Target: Cu
Detector: Lithium Drifted Diode
Tube voltage: 40 kV
Tube current: 30 mA
Slit: DS 1.0, RS 0.3 mm, SS 2 mm tube, 0.5 m detector
Scan speed: 1°/min
StepISampling: 0.02"
Scan range: 5 to 70"
Sample holder: Quartz holder (25 mm × 25 mm)
Goniometer: Theta-Theta, fixed horizontal mount, goniometer
Filter: Electronic
Monochromator: not used

TABLE 3

Characteristic Powder X-ray Diffraction Peaks (2Θ ± 0.2 2Θ)

6.9
11.9
13.6
19.5
19.7
20.2
20.5
21.7
23.3
24.2

TABLE 3-continued

Characteristic Powder X-ray Diffraction Peaks (2Θ ± 0.2 2Θ)

25.2
25.4
26.5
27.4
34.4
41.6
48.9
55.2
58.6

C. Characterization of Crystalline ER-806158 by DSC.

Figure 4:
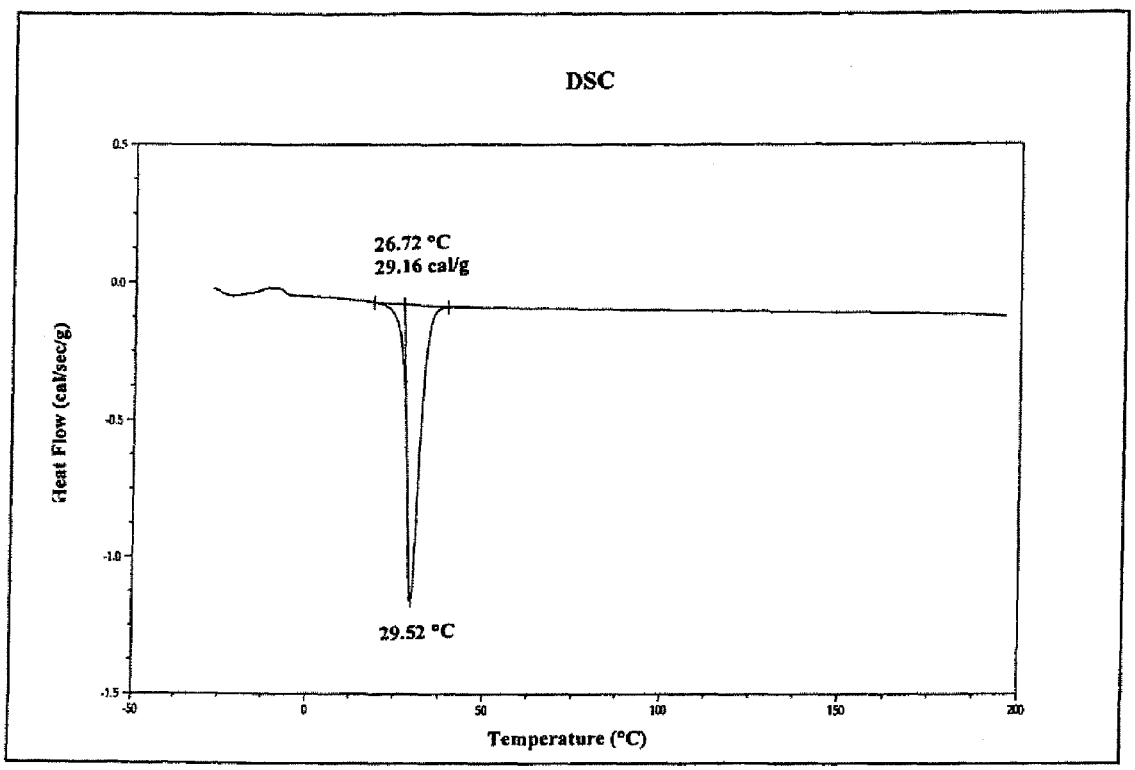
FIG. 4 shows the DSC thermograms of crystalline ER-806158.

Solid-state characterization of crystalline ER-806158 was determined by Differential Scanning Calorimetry (DSC, capillary technique). Using a 5.17000 mg sample of crystalline ER-806158, the DSC was run on a 2920 DSC V2.5F calorimeter heating to 200° C. at 10° C./min with an alumina pan under a nitrogen purge of 50 mL/min. FIG. 4 shows the thermograms of crystalline ER-806158 melted at 27° C. (onset temp.) absorbing +29.2 cal/g in the presence of nitrogen. A melt preceded by an exothermic event was observed during a reheat of the sample, which indicates this ER-806158 may be stable to 200° C. in the liquid phase.

D. Infrared Spectrum of Crystalline ER-806158

Figure 5:
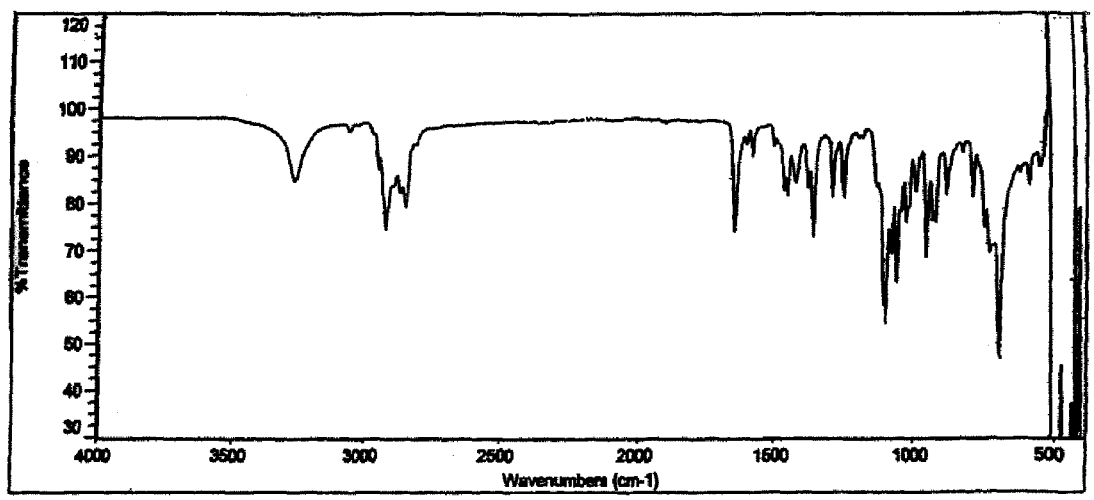
FIG. 5 shows the infrared spectrum of crystalline ER-806158.

The FTIR absorption spectrum of crystalline ER-806158 was recorded for the neat crystalline powder. The IR absorption spectrum of crystalline ER-806158 is shown in FIG. 5.

The claimed invention is:

1. A compound of formula (15):

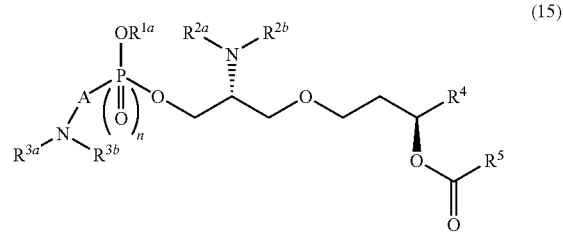

(15)

wherein:

A is —(CH$_2$)$_x$—O— or a covalent bond;

n is 0 or 1;

x is 1-6;

R$^{1a}$ is hydrogen, a C$_1$-C$_6$ alkyl group, a C$_3$-C$_6$ alkenyl group, a C$_3$-C$_6$ alkynyl group, or a phosphite oxygen protecting group or a phosphate oxygen protecting group;

one of R$^{2a}$ and R$^{2b}$ is H and the other is a monovalent nitrogen protecting group; or R$^{2a}$ and R$^{2b}$ taken together are a divalent nitrogen protecting group;

when A is —(CH$_2$)$_x$—O—, one of R$^{3a}$ and R$^{3b}$ is H and the other is a monovalent nitrogen protecting group, or R$^{3a}$ and R$^{3b}$ taken together are a divalent nitrogen protecting group;

when A is a covalent bond, R$^{3a}$ and R$^{3b}$ are a C$_1$-C$_6$ alkyl group, or R$^{3a}$ and R$^{3b}$ taken together are —(CH$_2$)$_4$—, —(CH$_2$)$_5$—, or —(CH$_2$)$_2$—O—(CH$_2$)$_2$—;

R$^4$ is a C$_5$-C$_{12}$ alkyl group or a C$_5$-C$_{12}$ alkenyl group; and

R$^5$ is a C$_5$-C$_{15}$ alkyl group or a C$_5$-C$_{15}$ alkenyl group;

or a salt thereof.

2. A compound of formula (15):

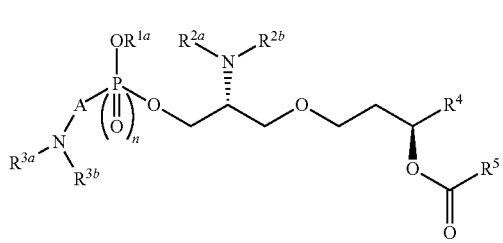

wherein:
- A is —(CH$_2$)$_x$—O— or a covalent bond;
- n is 0 or 1;
- x is 1-6;
- R$^{1a}$ is hydrogen, a C$_1$-C$_6$ alkyl group, a C$_3$-C$_6$ alkenyl group, a C$_3$-C$_6$ alkynyl group, or a phosphite oxygen protecting group or a phosphate oxygen protecting group;
- one of R$^{2a}$ and R$^{2b}$ is H and the other is a monovalent nitrogen protecting group; or R$^{2a}$ and R$^{2b}$ taken together are a divalent nitrogen protecting group;
- when A is —(CH$_2$)$_x$—O—, one of R$^{3a}$ and R$^{3b}$ is H and the other is a monovalent nitrogen protecting group, or R$^{3a}$ and R$^{3b}$ taken together are a divalent nitrogen protecting group;
- when A is a covalent bond, R$^{3a}$ and R$^{3b}$ are a C$_1$-C$_6$ alkyl group, or R$^{3a}$ and R$^{3b}$ taken together are —(CH$_2$)$_4$—, —(CH$_2$)$_5$—, or —(CH$_2$)$_2$O(CH$_2$)$_2$—;
- R$^4$ is a C$_5$-C$_{12}$ alkyl group or a C$_5$-C$_{12}$ alkenyl group;
- R$^5$ is a C$_5$-C$_{15}$ alkyl group or a C$_5$-C$_{15}$ alkenyl group; and
- wherein the nitrogen protecting group of R$^{2a}$ and R$^{2b}$ or R$^{3a}$ and R$^{3b}$ are independently selected from the group consisting of Boc, Fmoc, TROC, TMS-ethylcarbonyl, cyanoethylcarbonyl, allyloxycarbonyl, (C$_6$H$_5$)$_2$C=, tetrachlorophthalamide, or azide;

or a salt thereof.

3. The compound of claim 1, wherein the protecting group on the nitrogen linked to R$^{2a}$ and R$^{2b}$ can be removed under a first condition selected from acidic, basic, oxidative, and reductive conditions; and the protecting group on the nitrogen linked to R$^{3a}$ and R$^{3b}$ can be removed under a second condition selected from the remaining three conditions that are different from the first condition.

4. The compound of claim 1, wherein A is —(CH$_2$)$_2$—O—; n is 0; R$^4$ is a C$_7$ alkyl; and R$^5$ is a C$_{11}$ alkyl.

5. The compound of claim 4, having the formula ER-820842:

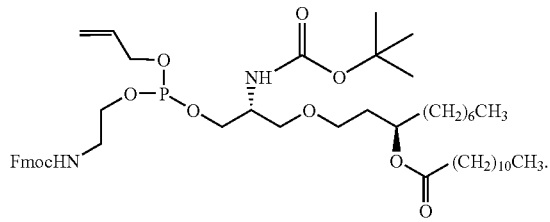

ER-820842

6. The compound of claim 1, wherein A is —(CH$_2$)$_2$—O—; n is 1; R$^4$ is a C$_7$ alkyl; and R$^5$ is a C$_{11}$ alkyl.

7. The compound of claim 6, having the formula ER-819344:

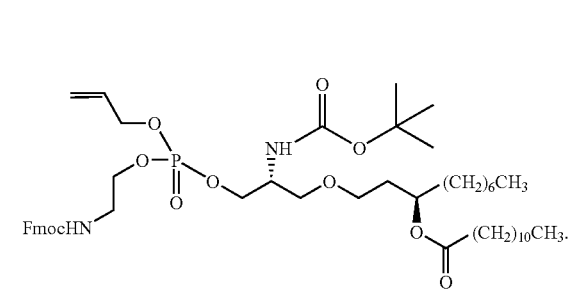

ER-819344

8. The compound of claim 1, wherein A is a covalent bond, n is 0; R$^4$ is a C$_7$ alkyl; and R$^5$ is a C$_{11}$ alkyl.

9. The compound of claim 8, having the formula ER-819385:

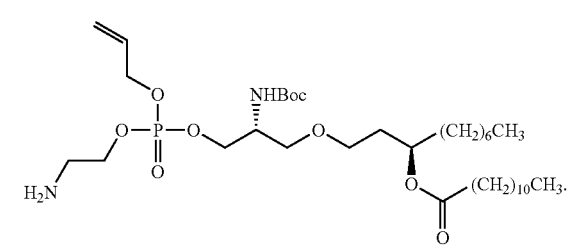

ER-819385-00

10. The compound of claim 1, wherein A is a covalent bond, n is 0; R$^{3a}$ and R$^{3b}$ are each isopropyl; R$^4$ is a C$_7$ alkyl; and R$^5$ is a C$_{11}$ alkyl.

11. The compound of claim 10, having the formula ER820116:

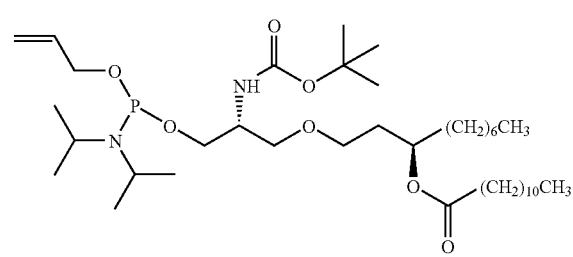

ER-820116

12. The compound of claim 2, wherein the protecting group on the nitrogen linked to R$^{2a}$ and R$^{2b}$ can be removed under a first condition selected from acidic, basic, oxidative, and reductive conditions; and the protecting group on the nitrogen linked to R$^{3a}$ and R$^{3b}$ can be removed under a second condition selected from the remaining three conditions that are different from the first condition.

13. The compound of claim 2, wherein A is —(CH$_2$)$_2$—O—; n is 0; R$^4$ is a C$_7$ alkyl; and R$^5$ is a C$_{11}$ alkyl.

14. The compound of claim 13, having the formula ER-820842:

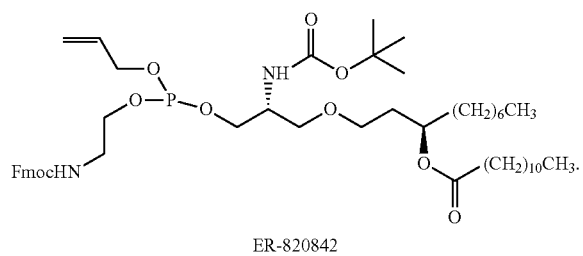

ER-820842

15. The compound of claim 2, wherein A is —(CH$_2$)$_2$—O—; n is 1; R$^4$ is a C$_7$ alkyl; and R$^5$ is a C$_{11}$ alkyl.

16. The compound of claim 15, having the formula ER-819344:

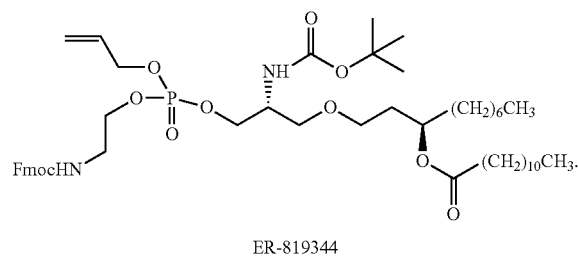

ER-819344

17. The compound of claim 2, wherein A is a covalent bond, n is 0; R$^4$ is a C$_7$ alkyl; and R$^5$ is a C$_{11}$ alkyl.

18. The compound of claim 17, having the formula ER-819385:

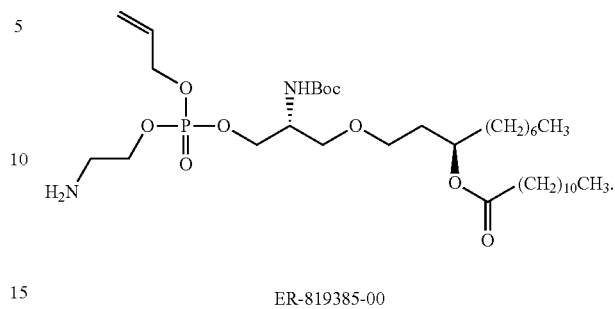

ER-819385-00

19. The compound of claim 2, wherein A is a covalent bond, n is 0; R$^{3a}$ and R$^{3b}$ are each isopropyl; R$^4$ is a C$_7$ alkyl; and R$^5$ is a C$_{11}$ alkyl.

20. The compound of claim 19, having the formula ER820116:

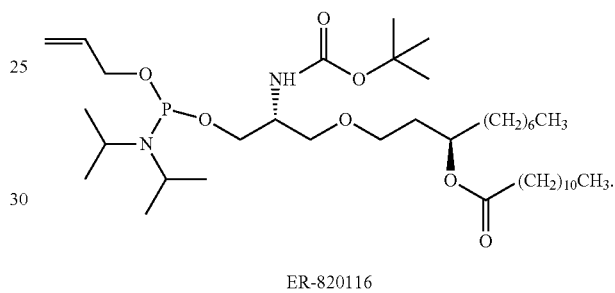

ER-820116

\* \* \* \* \*

UNITED STATES PATENT AND TRADEMARK OFFICE
CERTIFICATE OF CORRECTION

PATENT NO. : 8,198,474 B2
APPLICATION NO. : 12/698686
DATED : June 12, 2012
INVENTOR(S) : Fang et al.

It is certified that error appears in the above-identified patent and that said Letters Patent is hereby corrected as shown below:

Column 23, Formula (16): correct

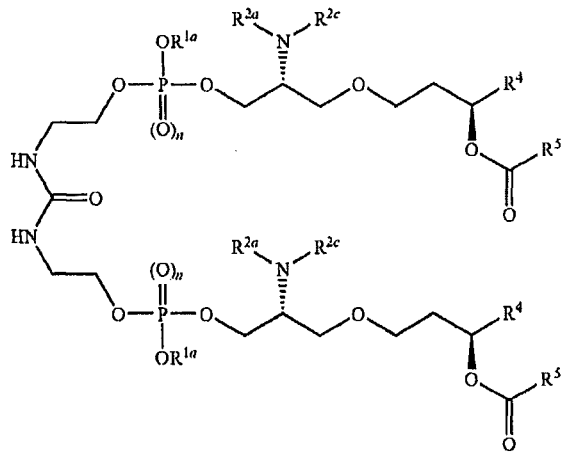

to read

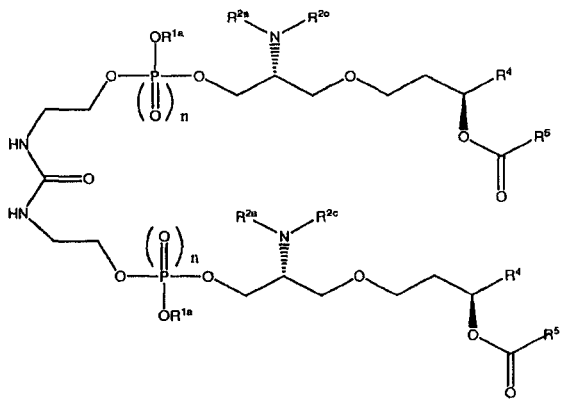

Column 66, Claim 1, Line 64: correct "or —$(CH_2)_2$—O—$(CH_2)_2$—;"
to read -- or —$(CH_2)_2O(CH_2)_2$—; --

Column 67, Claim 2, Line 31: correct "are —$(CH_7)_4$—,"
to read -- are —$(CH_2)_4$—, --

Signed and Sealed this
Twelfth Day of February, 2013

Teresa Stanek Rea
*Acting Director of the United States Patent and Trademark Office*